United States Patent
Colavito et al.

(10) Patent No.: US 12,004,946 B2
(45) Date of Patent: Jun. 11, 2024

(54) PROSTHETIC VALVE WITH IMPROVED WASHOUT

(71) Applicant: Edwards Lifesciences Corporation, Irvine, CA (US)

(72) Inventors: Kyle W Colavito, Flagstaff, AZ (US); Dustin V Dienno, Flagstaff, AZ (US); Logan R Hagaman, Flagstaff, AZ (US); Cody L Hartman, Flagstaff, AZ (US); Sudeep Sastry, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 311 days.

(21) Appl. No.: 17/178,802

(22) Filed: Feb. 18, 2021

(65) Prior Publication Data
US 2021/0177583 A1 Jun. 17, 2021

Related U.S. Application Data

(63) Continuation of application No. 16/001,886, filed on Jun. 6, 2018, now Pat. No. 10,952,842.

(60) Provisional application No. 62/516,568, filed on Jun. 7, 2017.

(51) Int. Cl.
*A61F 2/24* (2006.01)
*B01D 71/36* (2006.01)

(52) U.S. Cl.
CPC .......... *A61F 2/2412* (2013.01); *A61F 2/2418* (2013.01); *A61F 2/2475* (2013.01); *A61F 2220/0075* (2013.01); *A61F 2230/0095* (2013.01); *A61F 2250/0014* (2013.01); *B01D 71/36* (2013.01)

(58) Field of Classification Search
CPC .... A61F 2/2418; A61F 2/2412; A61F 2/2475; A61F 2/246
USPC .......................................................... 623/1.24
See application file for complete search history.

(56) References Cited

U.S. PATENT DOCUMENTS

| | | |
|---|---|---|
| 5,708,044 A | 1/1998 | Branca |
| 6,541,589 B1 | 4/2003 | Baillie |
| 7,261,732 B2 | 8/2007 | Justino |

(Continued)

FOREIGN PATENT DOCUMENTS

| | | |
|---|---|---|
| CN | 103458934 | 12/2013 |
| WO | WO-02/100297 | 12/2002 |

OTHER PUBLICATIONS

International Search Report for PCT/US2018/036520 dated Sep. 3, 2018, corresponding to U.S. Appl. No. 16/001,886, 4 pages.

*Primary Examiner* — Brian E Pellegrino
(74) *Attorney, Agent, or Firm* — Klarquist Sparkman, LLP; Sean Seung Kyu Kim

(57) ABSTRACT

Described embodiments are directed toward prosthetic valves having a support structure and at least one leaflet. The leaflet comprises means for allowing fluid that is behind the leaflet to pass through to the front of the leaflet when the leaflet is not in the closed position. The prosthetic valve includes a leaflet moveable between an open position that permits antegrade flow through the prosthetic valve and a closed position that prevents regurgitant flow through the prosthetic valve, the leaflet having an aperture or gap, or a separation of portions of the leaflet to allow a flow or exchange of fluid between a front and back of the leaflet, when the leaflet is not in the closed position.

26 Claims, 34 Drawing Sheets

(56) References Cited

U.S. PATENT DOCUMENTS

| | | |
|---|---|---|
| 7,306,729 B2 | 12/2007 | Bacino et al. |
| 7,361,189 B2 | 4/2008 | Case |
| 7,531,611 B2 | 5/2009 | Sabol et al. |
| 7,648,527 B2 | 1/2010 | Agnew |
| 7,811,316 B2 | 10/2010 | Kalmann |
| 8,021,417 B2 | 9/2011 | Osborne |
| 8,109,993 B2 | 2/2012 | Hinchliffe |
| 8,637,144 B2 | 1/2014 | Ford |
| 8,961,599 B2 | 2/2015 | Bruchman et al. |
| 9,139,669 B2 | 9/2015 | Xu et al. |
| 9,554,900 B2 | 1/2017 | Bruchman et al. |
| 9,737,398 B2 | 8/2017 | Bruchman et al. |
| 9,801,712 B2 | 10/2017 | Bruchman et al. |
| 2004/0059411 A1 | 3/2004 | Strecker |
| 2005/0228495 A1 | 10/2005 | Macoviak |
| 2008/0183279 A1 | 7/2008 | Bailey et al. |
| 2011/0118833 A1 | 5/2011 | Reichenbach |
| 2013/0123908 A1 | 5/2013 | Hinchliffe |
| 2013/0304196 A1 | 11/2013 | Kelly |
| 2013/0325117 A1* | 12/2013 | Bruchman ............ A61F 2/2412 156/60 |

* cited by examiner

PROSTHETIC VALVE WITH IMPROVED WASHOUT

FIELD

The present disclosure relates generally to prosthetic valves and more specifically flexible leaflet-type prosthetic heart valve devices.

BACKGROUND

Prosthetic valves are used to replace natural valves in a cardiovascular system when the natural valve no longer functions properly. A flexible leaflet prosthetic valve comprises one or more leaflets that move under the influence of fluid pressure.

Prosthetic leaflets are attached to a support structure to form a valve. In operation, the flexible leaflets open when the inflow fluid pressure exceeds the outflow fluid pressure and close when the inflow fluid pressure drops below the outflow fluid pressure. The free edges of the leaflets coapt under the influence of outflow fluid pressure closing the valve to prevent outflow blood from flowing retrograde through the valve. FIGS. 1A and 1B are perspective and axial views, respectively, of a closed prosthetic valve 10 that includes a frame 20 that supports leaflets 30, in accordance to what is known in the art. The closed prosthetic valve 10 represents when the outflow pressure downstream of the prosthetic valve 10 is greater than the inflow pressure upstream of the prosthetic valve 10, wherein the leaflets 30 close to prevent regurgitant flow through the prosthetic valve 10.

FIGS. 1C and 1D are a perspective view and axial view, respectively, of the prosthetic valve 10 where the leaflets 30 are open such as when the inflow pressure upstream of the prosthetic valve 10 is greater than the outflow pressure, wherein the leaflets 30 open to allow fluid to proceed in the forward flow direction 402 through the prosthetic valve 100.

FIGS. 1E and 1F are cross-sectional views of the closed prosthetic valve 10 of FIG. 1B along outline 1E-1E and the open prosthetic valve 10 of FIG. 1D along cut line 1F-1F, respectively. FIG. 1E shows the retrograde flow direction 404 where the outflow pressure of the prosthetic valve 10 is greater than the inflow pressure thus closing the leaflet 30. FIG. 1F shows the fluid moving in the forward flow direction 402 through the prosthetic valve 10 where the inflow pressure is greater than the outflow pressure thus opening the flexible leaflet 30 away from the valve axis X. Behind the leaflet 30 the fluid follows a recirculating direction, referred to as recirculating flow 406, including flow in the retrograde flow direction 404 between the leaflet 30 and a structure behind the leaflet 30, such as, but not limited to, the frame 20, a prosthetic conduit, and native tissue.

The lack of or insufficient fluid in the retrograde flow direction 404 or recirculating flow 406 can result in the fluid flow slowing or stagnating behind the leaflet 30 and in particular, at the leaflet base 308 where the leaflet 30 intersects the frame 20. The slowing or stagnation of fluid flow is known to cause the blood to clot and form thrombus. Thrombus is detrimental in that it can hinder the leaflet 30 opening and closing dynamics which in turn leads to increased pressure gradients that negatively affect valve performance. Thrombus may also flow downstream which can lead to stroke, heart attack or pulmonary embolism.

There remains a need for a prosthetic valve that reduces or eliminates the reduced or stagnated flow behind an open prosthetic valve leaflet.

SUMMARY

Described embodiments are directed to apparatus, system, and methods for valve replacement, such as cardiac valve replacement. More specifically, described embodiments are directed toward flexible leaflet valve devices having biological or synthetic leaflet material and a support structure, and methods of making and implanting the valve devices.

According to one example (Example 1), a valve having a leaflet moveable between an open position that permits antegrade flow through the prosthetic valve and a closed position that prevents regurgitant flow through the prosthetic valve, the leaflet comprising an aperture or gap, or a separation of portions of the leaflet to allow a flow or exchange of fluid between the front and back of the leaflet, when the leaflet is not in the closed position.

According to another example (Example 2), further to Example 1, the aperture, gap or separation is operable to close to prevent flow of exchange of fluid between the back and the front of the leaflet, when the leaflet is in the closed position.

According to another example (Example 3), further to Examples 1 or 2, comprising a support structure, wherein the leaflet is coupled to the support structure.

According to another example (Example 4), further to of Examples 1-3, the leaflet includes a first leaflet component and a second leaflet component.

According to another example (Example 5), further to Example 4, the first leaflet component is upstream of the second leaflet component, or wherein the first leaflet component is downstream of the second leaflet component.

According to another example (Example 6), further to Examples 4 or 5, said flow or exchange of fluid is via an aperture, gap or separation of the first and second components, when the leaflet is not in the closed position.

According to another example (Example 7), further to any one of Examples 4 to 6, and in accordance with Example 1, the second leaflet component comprises an inflow free edge; and defines a gap between the second leaflet component and the support structure.

According to another example (Example 8), further to any one of Examples 4 to 7, the first leaflet component or the second leaflet component defines an aperture therethrough; and wherein the other of the first leaflet component or the second leaflet component is operable to occlude the aperture.

According to another example (Example 9), further to any one of Examples 4 to 8, the first leaflet component and the second leaflet component partially overlap.

According to another example (Example 10), further to Example 9, the first leaflet component comprises a first overlap region and the second leaflet component comprises a second overlap region; wherein the first and second overlap regions are in sealing engagement with one another, when the leaflet is in the closed position.

According to another example (Example 11), further to Example 10, the first and second overlap regions each extend from a free edge of the respective first and second leaflet component.

According to another example (Example 12), further to Example 11, the first overlap region extends from an outflow free edge of the first leaflet component and the second overlap region extends from an inflow free edge of the second leaflet component.

According to another example (Example 13), further to any one of Examples 10 or 11, the first leaflet component comprises apertures in the first overlap region, or wherein the second leaflet component comprises apertures in the second overlap region.

According to another example (Example 14), further to any one of Examples 4 to 13, the first leaflet component is stationary relative to the second leaflet component, or vice versa.

According to another example (Example 15), further to any one of Examples 4 to 13, and in accordance with Example 3, the first leaflet component, or the second leaflet component is stationary relative to the support structure.

According to another example (Example 16), further to any one of Examples 4 to 13, the first leaflet component is configured to move more slowly than the second leaflet component.

According to another example (Example 17), further to Example 16, the first leaflet component has a higher bending stiffness than the second leaflet component.

According to another example (Example 18), further to any one of Examples 16 or 17, the first leaflet component is upstream of the second leaflet component.

According to another example (Example 19), further to any one of Examples 4 to 13, the second leaflet component is configured to move more slowly than the first leaflet component.

According to another example (Example 20), further to Example 19, the second leaflet component has a higher bending stiffness than the first leaflet component.

According to another example (Example 21), further to any one of Examples 19 or 20, the second leaflet component is upstream of the first leaflet component.

According to another example (Example 22), further to any one of Examples 9 to 21, and in accordance with Example 3, the first and second leaflet components overlap and define an overlap region which tapers in width towards the support structure.

According to another example (Example 23), further to Example 22, when the leaflet is in the closed position, there is a regurgitant gap or gaps of a predetermined size between the first and second leaflet components, extending away from the support structure.

According to another example (Example 24), further to any one of Examples 1-23, the leaflet comprises multiple apertures, gaps or separations of portions of the leaflet, to allow a flow or exchange of fluid between the front and back of the leaflet, when the leaflet is not in the closed position.

According to another example (Example 25), further to any one of Examples 4 to 23, the leaflet comprises multiple first leaflet components and/or wherein the leaflet comprises a first leaflet component comprising multiple outflow free edges.

According to another example (Example 26), further to Example 25, further includes a tether element which couples the multiple first leaflets or multiple outflow free edges to tether element may prevent prolapse.

According to another example (Example 27), further to any one of Examples 25 or 26, in further of example 3, the second leaflet component comprises multiple inflow free edges, defining multiple gaps between the second leaflet component and the support structure, corresponding to one of the said multiple first leaflet components or outflow free edges.

According to another example (Example 28), further to any one of Examples 24 to 26, the second leaflet component defines multiple apertures therethrough, wherein the first leaflet component is operable to occlude the apertures, or wherein one said multiple first leaflet components is operable to occlude each said aperture.

According to another example (Example 29), further to any one of Examples 1-28, wherein the shape of the shape of the leaflet, and, and in further of Example 3, the shape of a corresponding attachment region to a support structure, is generally that of a parabola or of an isosceles trapezoid.

According to another example (Example 30), further to any one of Examples 1-23, the leaflet comprises a porous polymer membrane and a material present in pores of the porous polymer membrane such that the or each leaflet is impermeable.

According to another example (Example 31), further to Examples 30, the porous polymer membrane is expanded polytetrafluoroethylene.

According to another example (Example 32), further to any one of Examples 30 or 31, the material present in the pores is an elastomer or an elastomeric material or a non-elastomeric material.

According to another example (Example 33), further to any one of Examples 30 to 32, the material present in the pores is a TFE/PMVE copolymer.

According to another example (Example 34), further to any one of Examples 1-33, the leaflet comprises a biological tissue.

According to another example (Example 35), further to any one of Examples 30 to 34, the leaflet comprises when in further of any one of Examples 4 to 13, wherein the or each first leaflet component and/or the second leaflet component comprises said porous polymer membrane and a material present in pores of the porous polymer membrane such that the or each first leaflet component and/or the second leaflet component is impermeable.

According to another example (Example 36), further to Example 35, wherein at least one of the first leaflet component and the second leaflet component comprises a biological tissue.

According to another example (Example 37), further to any one of Examples 1-36, the leaflet is coupled to a support structure in the form of a frame.

According to another example (Example 38), further to Example 38, the frame defines a generally open pattern of apertures operable to allow the frame to be compressed and expanded between different diameters.

According to another example (Example 39), further to any one of Examples 1 to 38, comprising a plurality of leaflets.

According to another example (Example 40), further to Example 39, comprising valve may comprise three leaflets.

According to another example (Example 41), further to any one of Examples 39 or 40, wherein each leaflet comprises a leaflet free edge, wherein leaflet free edges may coapt under the influence of retrograde fluid pressure; thereby closing the valve.

According to another example (Example 42), further to any one of Examples 1 to 41, wherein the valve is a prosthetic valve.

According to another example (Example 43), further to Examples 42, wherein the prosthetic valve is a prosthetic heart valve.

The foregoing Examples are just that, and should not be read to limit or otherwise narrow the scope of any of the inventive concepts otherwise provided by the instant disclosure.

According to another example (Example 44), a method of making a prosthetic valve, comprising: obtaining a support structure such as a leaflet frame or conduit, obtaining a leaflet including a first leaflet component and a second leaflet component; coupling the first leaflet component adjacent to an inlet portion of the support structure; and coupling the second leaflet component adjacent to an outlet portion of the support structure such that a second overlap region of a second inflow free edge of the second leaflet component overlaps a first overlap region of a first outflow free edge of the first leaflet component such that a portion of a second inflow side of the second leaflet component is in contact and in sealing engagement with a portion of a first outflow side of the first leaflet component when the leaflet is in a closed position defining a leaflet overlap region preventing fluid flow through a lumen in a retrograde direction, and wherein the first overlap region and the second overlap region are not in contact therewith wherein the first outflow free edge and the second inflow free edge define a gap therebetween when the leaflet is not in the closed position, wherein fluid adjacent a second outflow side can pass through the gap during fluid flow in a forward direction.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

DETAILED DESCRIPTION

Figure 1A:
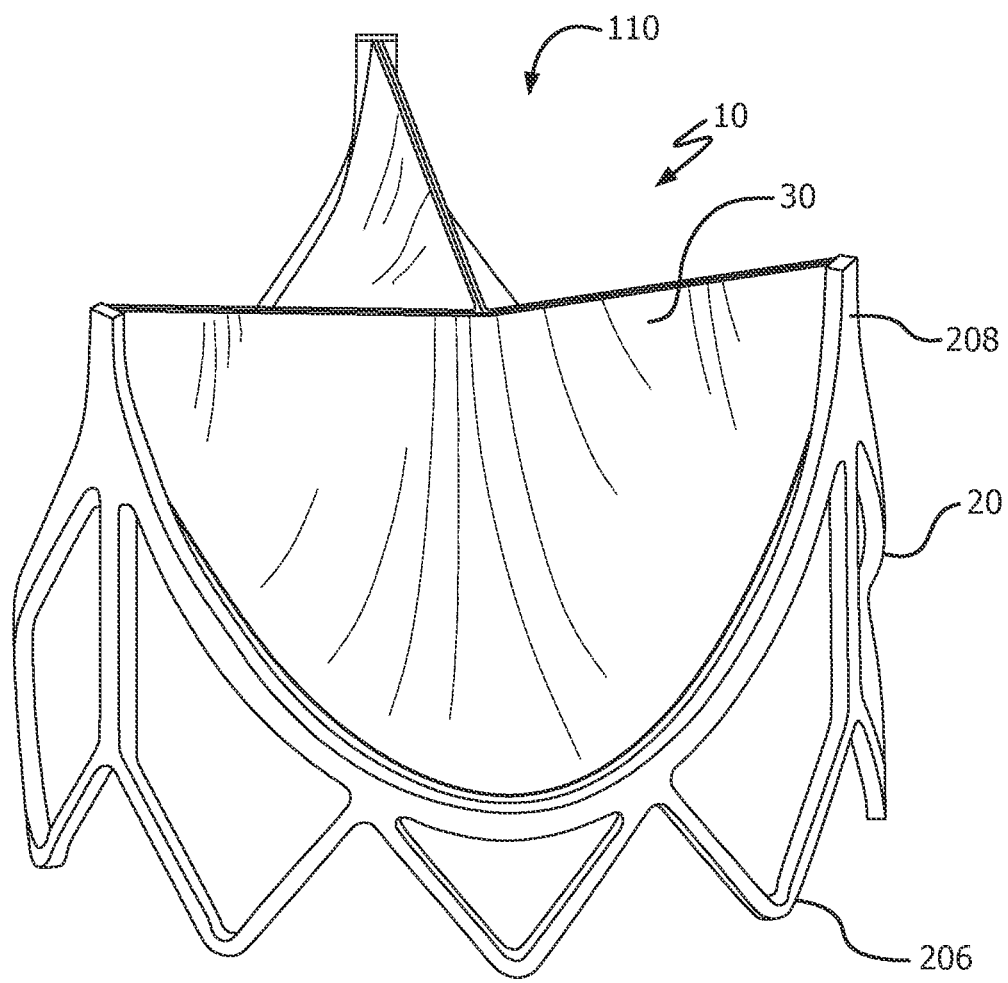
FIG. 1A is a perspective view of a closed prosthetic valve that includes a frame that supports leaflets, in accordance to what is known in the art.
Figure 1B:
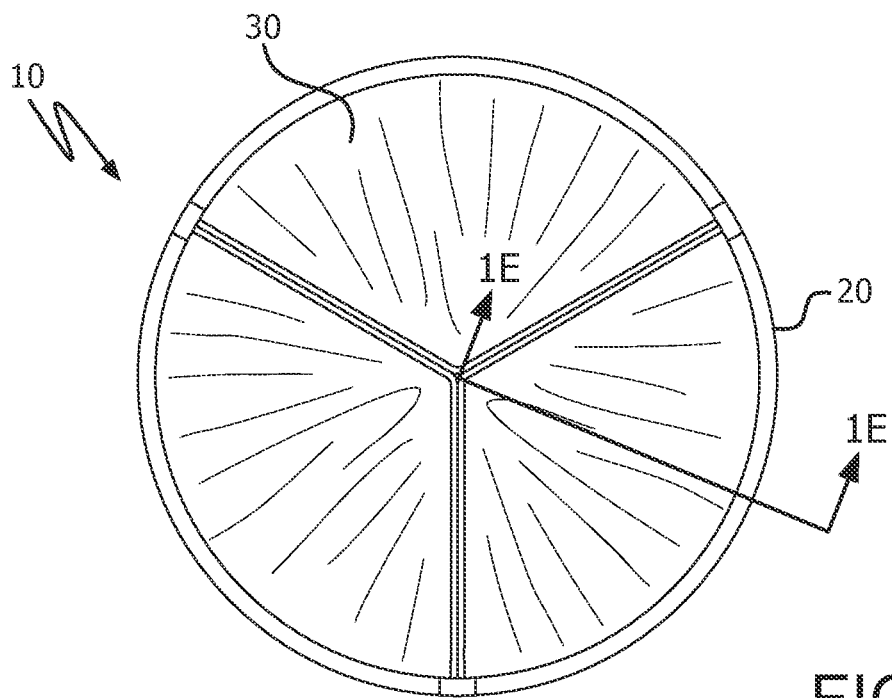
FIG. 1B is an axial view of the closed prosthetic valve of FIG. 1A that includes a frame that supports leaflets, in accordance to what is known in the art.
Figure 1D:
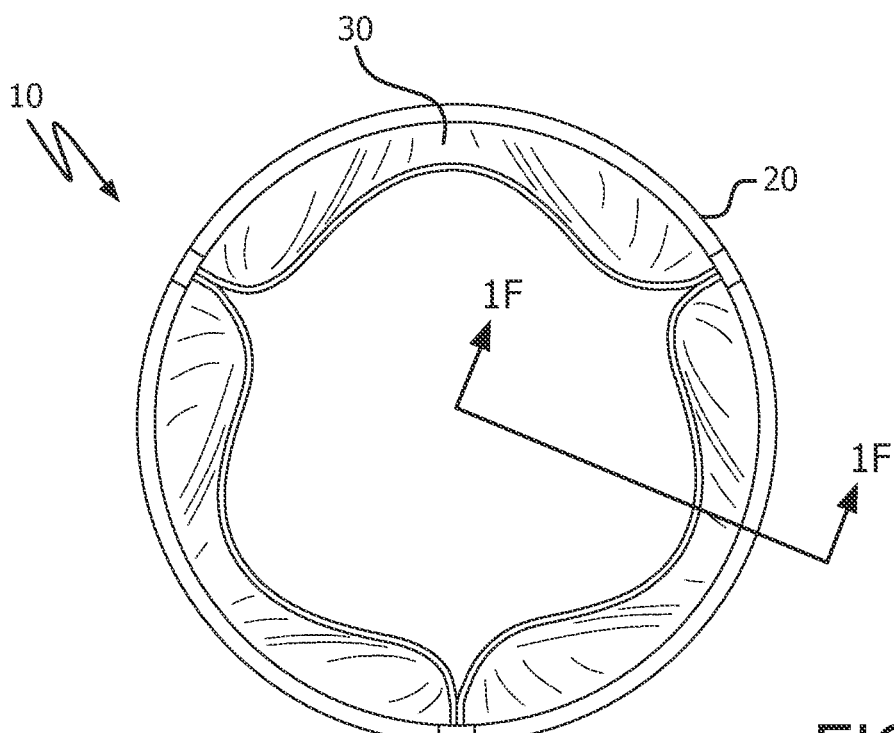
FIG. 1D is an axial view of the prosthetic valve of FIG. 1C where the leaflets are open such as when the outflow pressure upstream of the prosthetic valve is greater than the outflow pressure, wherein the leaflets open to allow forward flow through the prosthetic valve, in accordance to what is known in the art.
Figure 1C:
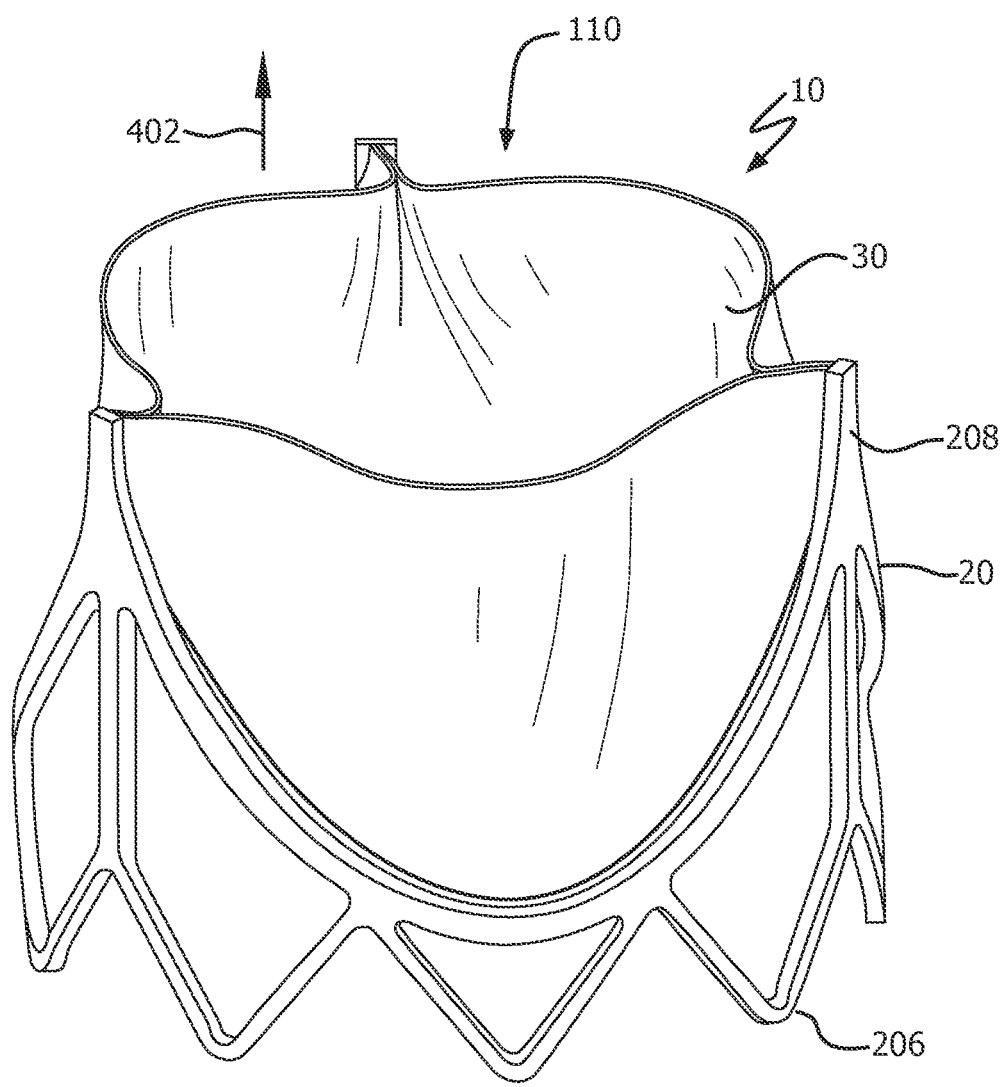
FIG. 1C is a perspective view of the prosthetic valve of FIG. 1A where the leaflets are open such as when the inflow pressure upstream of the prosthetic valve is greater than the outflow pressure, in accordance to what is known in the art.
Figure 1E:
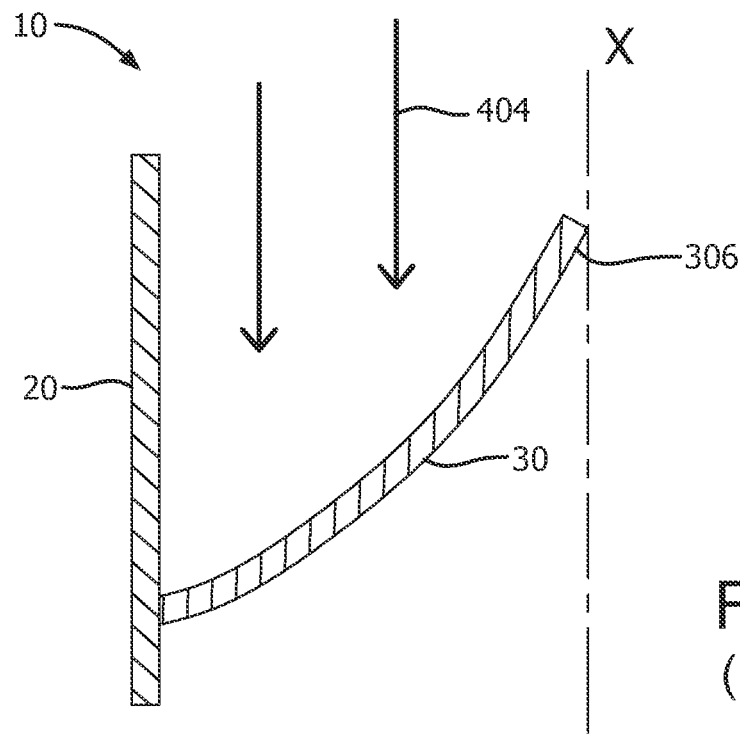
FIG. 1E is a cross-sectional view of the closed valve of FIG. 1B along cutline 1E-1E, in accordance to what is known in the art.
Figure 1F:
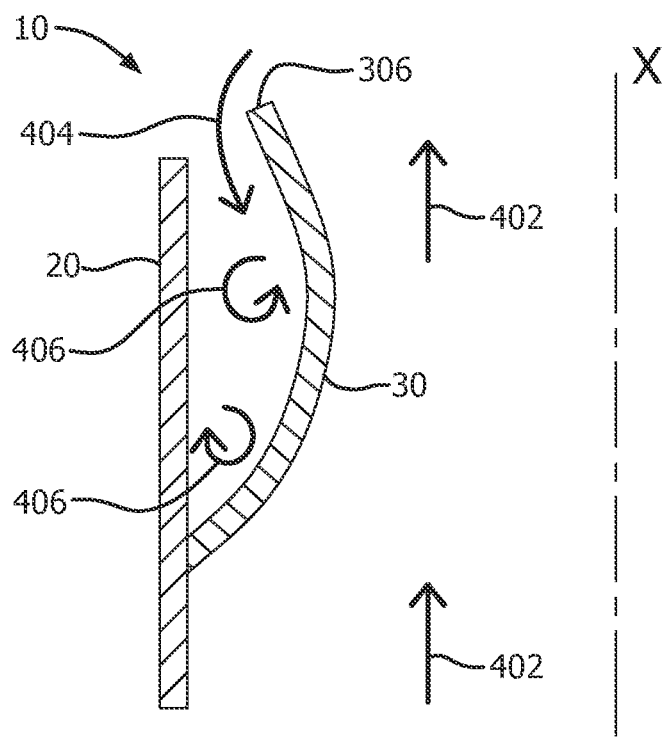
FIG. 1F is a cross-sectional view of the open valve of FIG. 1D along cutline 1F-1F, in accordance to what is known in the art.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term "leaflet" as used herein in the context of prosthetic valves is a flexible component of a one-way valve wherein the leaflet is operable to move between an open and closed position under the influence of a pressure differential. In an open position, the leaflet allows blood to flow through the valve. In a closed position, the leaflet substantially blocks retrograde flow from passing through the valve. In embodiments comprising multiple leaflets, each leaflet cooperates with at least one neighboring leaflet to block the retrograde flow from becoming regurgitant. The pressure differential in the blood is caused, for example, by the contraction of a ventricle or atrium of the heart, or the drainage of blood from the ventricle or atrium. As the pressure on the inflow side of the valve rises above the pressure on the outflow side of the valve, the leaflets are caused to open and blood flows therethrough. As blood flows through the valve into a neighboring chamber or blood vessel, the pressure on the inflow side equalizes with the pressure on the outflow side. As the pressure on the inflow side of the valve drops below the pressure on the outflow side of the valve, the leaflets are caused to return to the closed position generally preventing regurgitant flow of blood through the valve.

As used herein, "inflow fluid pressure" refers to a fluid pressure at an upstream location of the valve. "Outflow fluid pressure" refers to a fluid pressure at a downstream location of the valve.

As used herein, "retrograde" and "retrograde flow" refers to fluid flow at a downstream location of the valve that is moving toward the valve. Retrograde flow may be encountered, by way of example, but not limited to, in turbulent or recirculatory flow that is downstream of the valve, and during the pressure transition of the inflow fluid pressure dropping below the outflow fluid pressure tending to change the flow pattern away from a forward flow direction.

As used herein, "regurgitant", "regurgitation", and "regurgitant flow" refers to flow through a valve when the leaflets are in the close position. A valve that is exhibiting regurgitation is commonly said to be leaking. Regurgitant flow is differentiated from retrograde flow in that regurgitant flow is fluid flow that passes through the valve from a downstream location to an upstream location whereas retrograde flow is flow in a downstream location that does not necessarily pass through the valve.

The term "biocompatible material" as used herein generically refers to any material with biocompatible characteristics including synthetic, such as, but not limited to, a biocompatible polymer, or a biological material, such as, but not limited to, human, bovine, and pig tissue.

The terms "native valve" orifice and "tissue orifice" refer to an anatomical structure into which a prosthetic valve can be placed. Such anatomical structure includes, but is not limited to, a location wherein a cardiac valve may have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a valve.

As used herein, "couple" means to join, connect, attach, adhere, affix, or bond, whether directly or indirectly, and whether permanently or temporarily.

Embodiments herein include various apparatus, systems, and methods for a prosthetic valve, such as, but not limited to, cardiac valve replacement devices. The valve is operable as a one-way valve wherein the valve defines a valve orifice into which one or more flexible leaflets open to permit flow and close so as to occlude the valve orifice and prevent regurgitant flow in response to a differential fluid pressure. In accordance with embodiments, the leaflet is configured so as to increase the motion of fluid behind an open leaflet so as, but not limited to, reducing the likelihood of fluid stagnation and potential thrombus formation behind the open leaflet.

In accordance with embodiments, each of the one or more flexible leaflets comprise a means for allowing a flow or exchange of fluid between the front and back of the leaflet when the leaflet is not in the closed position through the leaflet via an aperture, gap or separation of portions of the leaflet. This flow or exchange of fluid may include fluid from in front of the leaflet passing through the leaflet to the back of the leaflet which displaces the existing fluid that is behind the leaflet and keeps that fluid in motion. This exchange of fluid may also include fluid from behind the leaflet passing through the leaflet to the front of the leaflet which displaces the existing fluid that is behind the leaflet and keeps it in motion.

In accordance with embodiments, a prosthetic valve includes at least one leaflet and a support structure supporting the leaflet so that it may operate as a one-way valve. As described in the embodiments presented below, the support structure is described as a frame and used herein as an example, and used interchangeably with support structure. It is understood that other support structures are anticipated, including, but not limited to, conduits, that are operable to support the leaflet for its intended function.

Figure 2A:
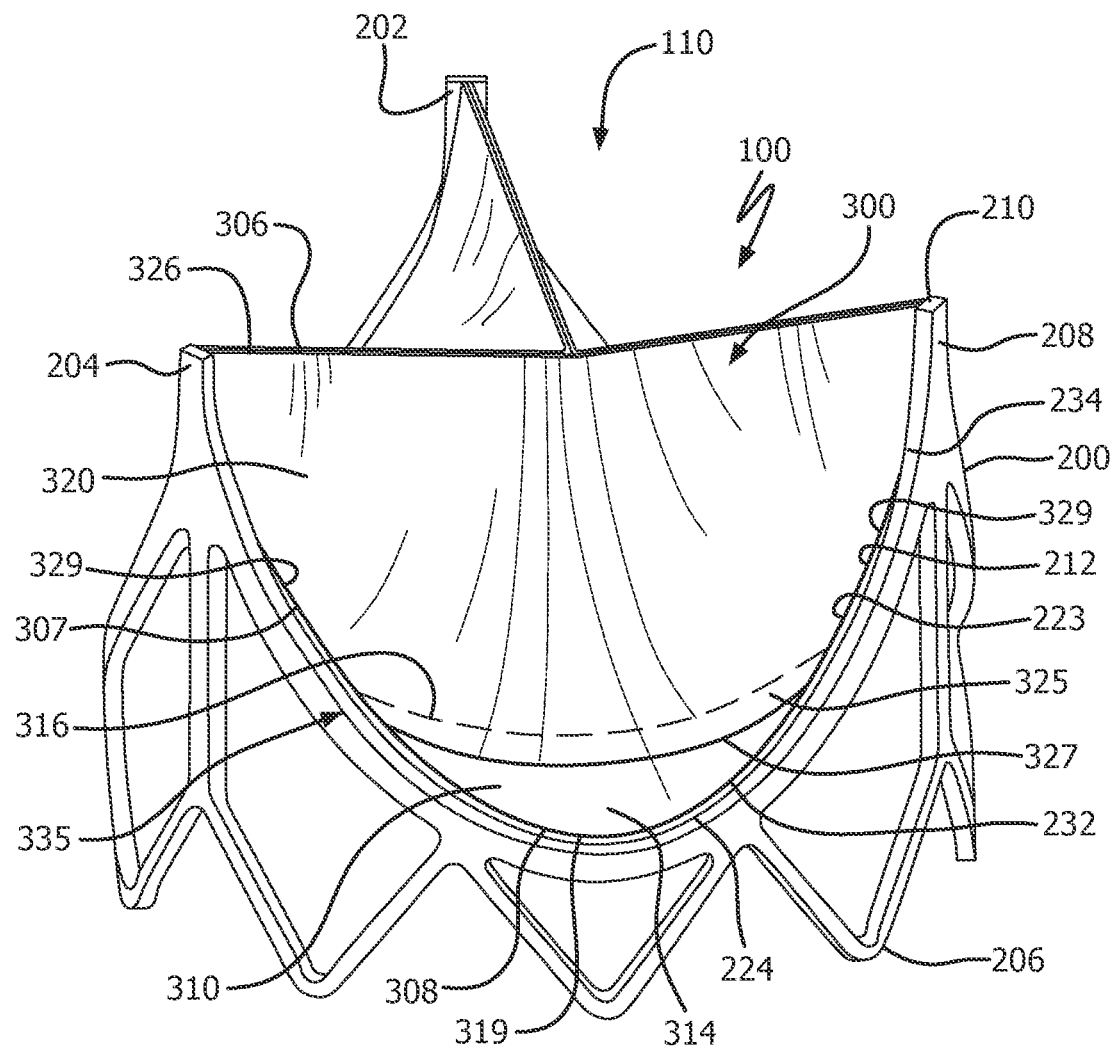
FIG. 2A is a perspective view of a prosthetic valve in a closed position, in accordance with an embodiment.
Figure 2B:
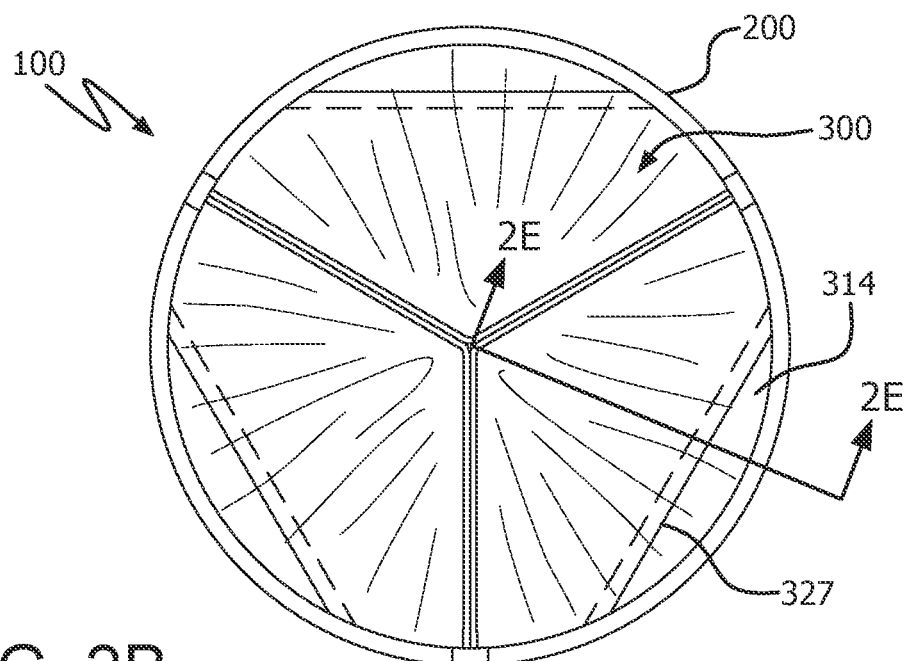
FIG. 2B is an axial view of the prosthetic valve of FIG. 2A in a closed position, in accordance with an embodiment.
Figure 2D:
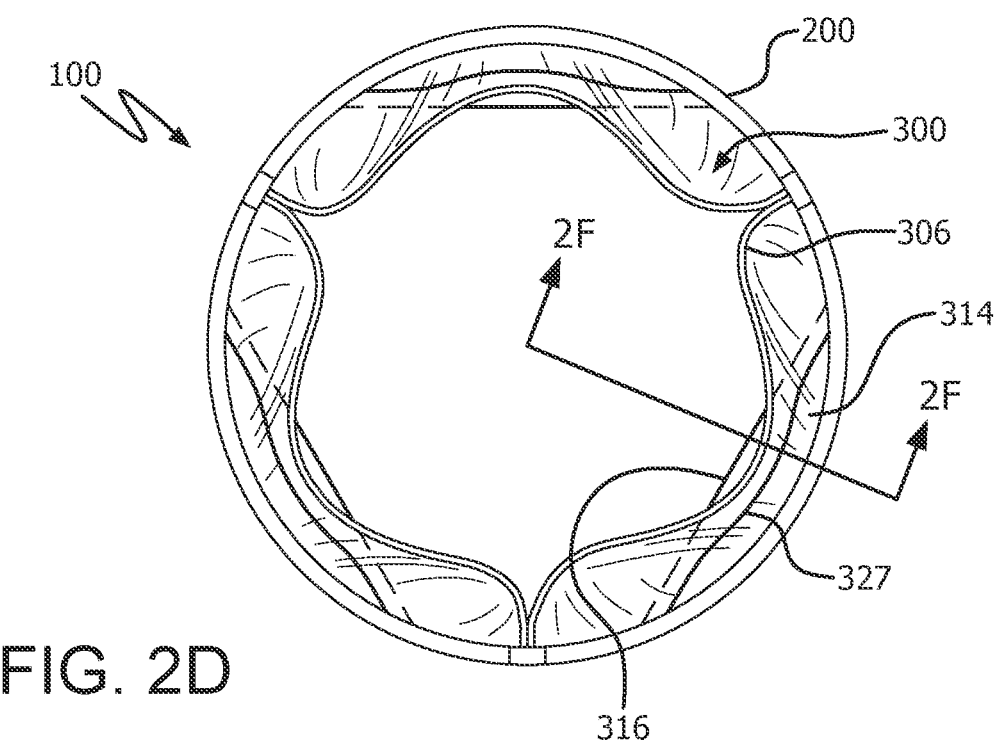
FIG. 2D is an axial view of the prosthetic valve FIG. 2C in an open position, in accordance with an embodiment.
Figure 2C:
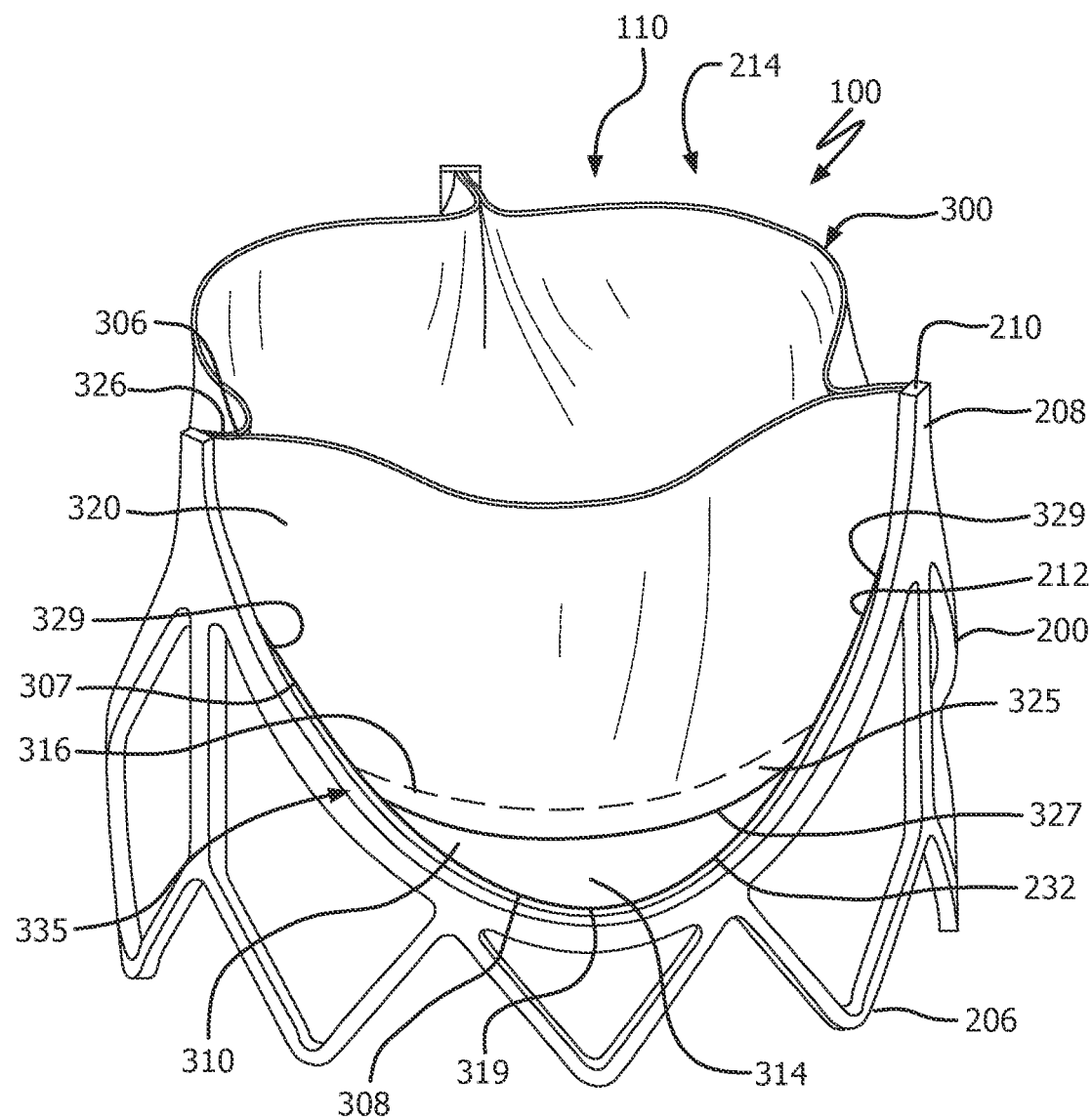
FIG. 2C is a perspective view of the prosthetic valve of FIG. 2A in an open position, in accordance with an embodiment.
Figure 2E:
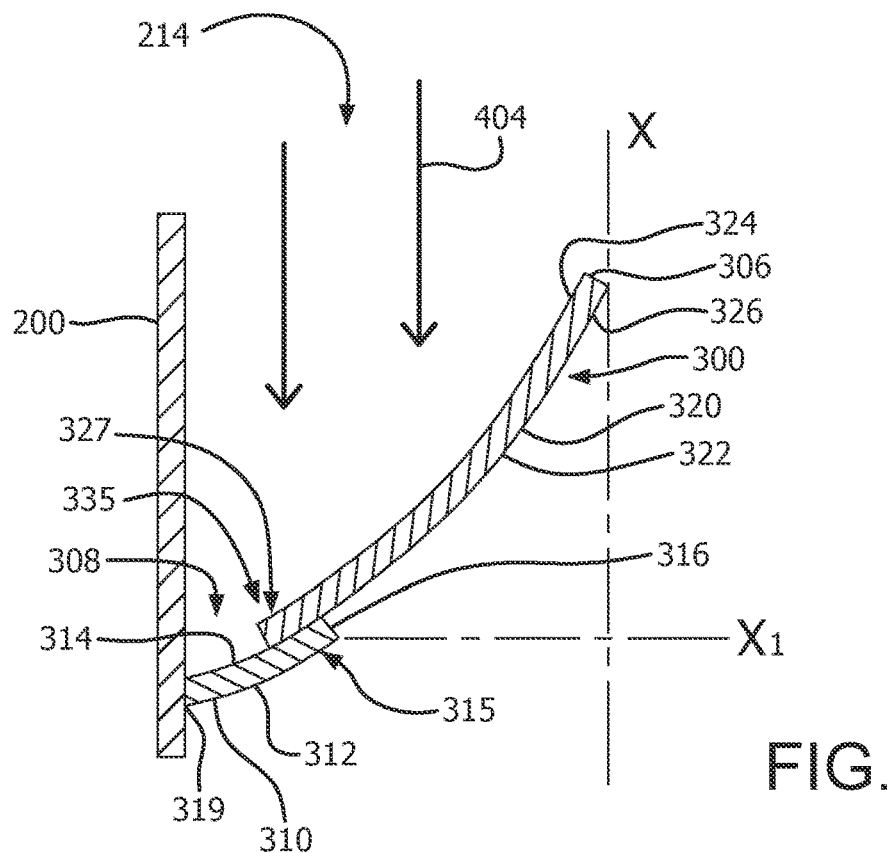
FIG. 2E is a cross-sectional view of the closed valve of FIG. 2B along cutline 2E-2E, in accordance with an embodiment.
Figure 2F:
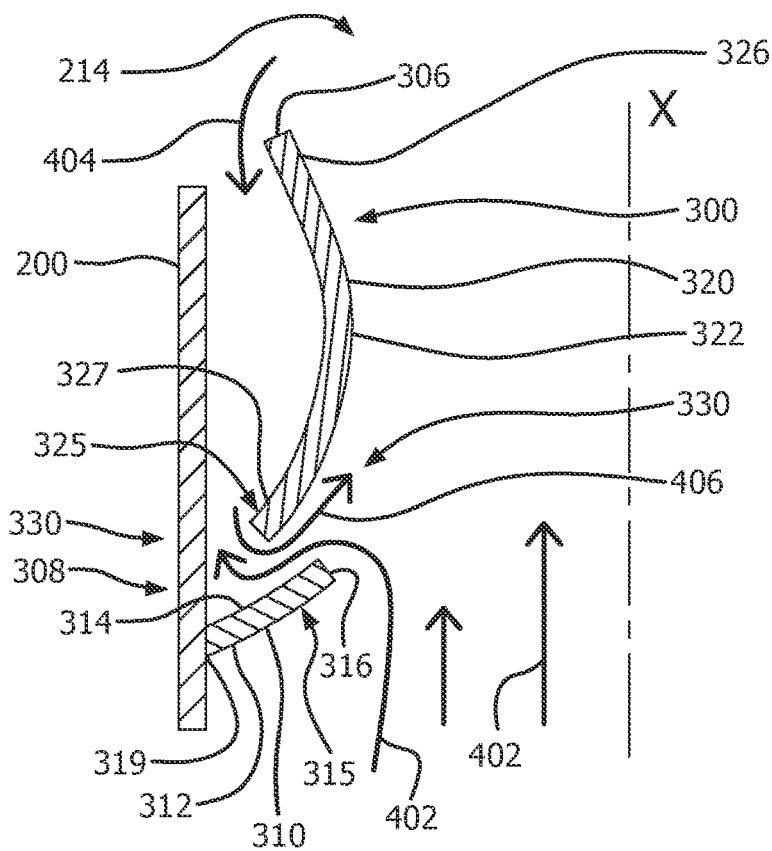
FIG. 2F is a cross-sectional view of the open valve of FIG. 2D along cutline 2F-2F, in accordance with an embodiment.

FIGS. 2A and 2B are perspective and axial views, respectively, of a prosthetic valve 100 in a closed position, in accordance with an embodiment. FIGS. 2C and 2D are perspective and axial views, respectively, of the prosthetic valve 100 in an open position, in accordance with an embodiment. FIGS. 2E and 2F are cross-sectional views of the closed prosthetic valve 100 of FIG. 2B along cutline 2E-2E and of the prosthetic valve 100 of FIG. 2D along cutline 2F-2F, respectively.

Frame

As shown in FIG. 2A, a frame 200 is operable to hold and support a plurality of leaflets 300. The frame 200 is annular, that is, it defines a cylinder having a lumen 214 having an axis X and a plurality of commissure posts 210 extending parallel to the axis X that are spaced from one another. Between the commissure posts 210 is a leaflet attachment region 212 that is operable to couple with and support the leaflet 300 about a perimeter of the leaflet 300 except for a leaflet free edge 306.

The frame 200 defines a cylinder having a frame inner side 202 and a frame outer side 204 opposite the frame inner side 202. The frame 200 further defines a plurality of commissure posts 210.

Although the frame 200 in the instant embodiment defines a cylinder of constant diameter along the axis X, it is understood that the diameter may vary along the axis X. Such variation may be advantageous, such as, but not limited to, to better fit the anatomy of the tissue orifice and adjacent upstream and downstream anatomy. Similarly, the frame 200 may not necessarily be circular along the axis X but, by way of example, but not limited thereto, may be oval and lobed. Such variation may be advantageous, such as, but not limited to, to better fit the anatomy of the tissue orifice and adjacent upstream and downstream anatomy, and/or to control the flow dynamics through the valve and around the leaflets.

In accordance with an embodiment, the frame 200 is annular about a central longitudinal axis X of the prosthetic valve 100 as shown in FIGS. 2A-2D. The frame 200 has an inflow end 206 and an outflow end 208 opposite the inflow end 206 and defines a lumen 110 therebetween along an axis X. The frame 200 has at least one leaflet attachment region 212 for each leaflet 300. The leaflet attachment region 212 has an inflow portion 232 and an outflow portion 234.

The frame 200 can be etched, cut, laser cut, stamped, three-dimensional printed, among other suitable processes, into an annular structure or a sheet of material, with the sheet then formed into an annular structure. Wires and strands may also be used to form into an annular structure.

The frame 200 can comprise, such as, but not limited to, any metallic or polymeric material that is generally biocompatible. The frame 200 can comprise a shape-memory material, such as Nitinol, a nickel-titanium alloy. Other materials suitable for the frame 200 include, but not limited to, other titanium alloys, stainless steel, cobalt-nickel alloy, polypropylene, acetyl homopolymer, acetyl copolymer, other alloys or polymers, elastomers and elastomeric materials, other shape memory and/or superelastic materials, polymers, and composite materials, or any other material that is generally biocompatible having adequate physical and mechanical properties to function as a leaflet frame 200 as described herein. Suitable frames can be made from a variety of materials and need only be biocompatible or able to be made biocompatible.

It is appreciated that FIG. 2A shows a frame 200 that is operable to be used in a surgical procedure, wherein the frame 200 has a fixed diameter both pre- and post-implant. It is appreciated that the frame 200 may be configured for use in a transcatheter procedure, wherein the frame 200 can be expanded from a smaller pre-deployment diameter to a larger deployed diameter.

A wide variety of frames are known in the medical technology arts, and any suitable frame can be utilized. One requirement is that the frame provide a surface to which the leaflet can be attached and function as described herein.

As described below, in accordance with an embodiment, the frame has radially compressed and radially expanded configurations. Such a frame can be implanted at a point of treatment within a body vessel by minimally invasive techniques, such as delivery and deployment with an intravascular catheter. The frame can optionally provide additional function to the medical device. For example, the frame can provide a stenting function, i.e., exert a radially outward force on the interior wall of a vessel in which the medical device is implanted. By including a frame that exerts such a force, a medical device according to the invention can provide both a stenting and a valving function at a point of treatment within a body vessel.

The stent art provides numerous frames acceptable for use in the present invention, and any suitable stent can be used as the frame. The specific frame chosen will depend on numerous factors, including the body vessel in which the medical device is being implanted, the axial length of the treatment site within the vessel, the number of valves desired in the medical device, the inner diameter of the vessel, the delivery method for placing the medical device, and other considerations. Those skilled in the art can determine an appropriate frame based on these and other considerations.

The frame can be self-expandable or balloon expandable. The structural characteristics of both of these types of frames are known in the art, and are not detailed herein. Each type of frame has advantages and for any given application, one type may be more desirable than the other based on a variety of considerations. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, medical devices according to the invention intended for implantation in the peripheral vasculature, such as prosthetic venous valves, advantageously include a self-expandable frame. These frames, as is known in the art, are generally more flexible than balloon-expandable frames following deployment.

Suitable frames can also have a variety of shapes and configurations, including being comprised of wire, strands, braided strands, helically wound strands, ring members, consecutively attached ring members, zig-zag members, tubular members, and frames cut from solid tubes and flat sheets. Frames may define a generally open pattern of apertures operable to allow the frame to be compressed and expanded between different diameters, in accordance with embodiments.

Leaflet

As shown in FIGS. 2A-2F, the leaflet 300 is coupled to each of the at least one leaflet attachment region 212 of the frame 200.

The leaflet 300 includes a first leaflet component 310 and a second leaflet component 320, in accordance with an embodiment. The first leaflet component 310 has a first inflow side 312 and a first outflow side 314 opposite the first inflow side 312 that defines a first thickness. The term "inflow side" is that side which is facing the inflow end 206 of the frame 200 when the leaflet 300 is in the closed position. The term "outflow side" is that side which is facing the outflow end 208 of the frame 200 when the leaflet 300 is in the closed position. The first leaflet component 310 has a first frame attachment edge 319 and a first outflow free edge 316.

The second leaflet component 320 has a second inflow side 322 and a second outflow side 324 opposite the second inflow side 322 defining a second thickness. The second leaflet component 320 has a plurality of second frame attachment edges 329, a second inflow free edge 327 and a second outflow free edge 326 opposite the second inflow free edge 327. The second leaflet component 320 is configured to be movable between an open position to allow fluid flow in a forward flow direction through the lumen 214 and a closed position in cooperative engagement with the first leaflet component 310 that prevents regurgitant flow.

The first frame attachment edge 319 of the first leaflet component 310 is coupled to the inflow portion 232 of the leaflet attachment region 212 with the first inflow side 312 facing the axis X. The inflow portion 232 is that portion adjacent to the inflow end 206 of the frame 200.

The second frame attachment edges 329 of the second leaflet component 320 is coupled to the outflow portion 234 of the leaflet attachment region 212 with the second inflow side 322 facing the axis X. The outflow portion 234 is that portion adjacent to the outflow end 208 of the frame 200.

The first leaflet component 310 and the second leaflet component are arranged on the frame 200 such that they at least partially overlap. A second overlap region 325 adjacent to the second inflow free edge 327 overlaps a first overlap region 315 adjacent to the first outflow free edge 316 such that a portion of the second inflow side 322 of the second leaflet component 320 is in contact and in sealing engagement with a portion of the first outflow side 314 of the first leaflet component 310 when the leaflet 300 is in the closed position defining a leaflet overlap region 335 operable to prevent regurgitant flow through the leaflet 300 at the leaflet overlap region 335, as shown in FIG. 2E.

During fluid flow in the forward flow direction 402 when the leaflet 300 is not in the closed position, as shown in FIG. 2F, when the inflow pressure is greater than the outflow pressure, the first overlap region 315 and the second overlap region 325 move away from each other wherein the first outflow free edge 316 and the second inflow free edge 327 define a gap 330 therebetween. The gap 330 formed between the first leaflet component 310 and the second leaflet component 320 when the leaflet 300 is not in the closed position allows fluid adjacent the first outflow side 314 and the second outflow side 324 to pass through the gap 330 when the fluid is moving in the forward flow direction 402 through the lumen 214. That is, recirculating flow 406 from behind the leaflet 300 may pass through the gap 330 preventing the recirculating flow 406 from stagnating behind the leaflet 300. Further, the gap 330 also allows fluid flow in the forward flow direction 402 to pass through the gap 330 from the first inflow side 312 and the second inflow side 322 further disrupting and displacing the recirculating flow 406 behind the leaflet 300 to downstream of the leaflet 300. Thus, blood behind the leaflet 300 is less likely to clot or form thrombus, particularly at the leaflet base 308 and where it attaches to the frame 200.

In accordance with an embodiment, the first leaflet component 310 is stationary relative to the second leaflet component 320 such that the gap 330 may be formed between the second leaflet component 320 moving away from the first leaflet component 310 under fluid pressure during fluid flow in the forward flow direction 402.

In accordance with another embodiment, the first leaflet component 310 has a bending stiffness that is greater than the second leaflet component 320 such that the second leaflet component 320 may move more quickly relative to the first leaflet component 310 such that the gap 330 may be formed between the second leaflet component 320 moving away from the first leaflet component 310 under fluid pressure during fluid flow in the forward flow direction 402. Examples of providing a predetermined bending stiffness include, but not limited to, using a material having a predetermined modulus and providing a component of predetermined thickness.

Figure 3A:
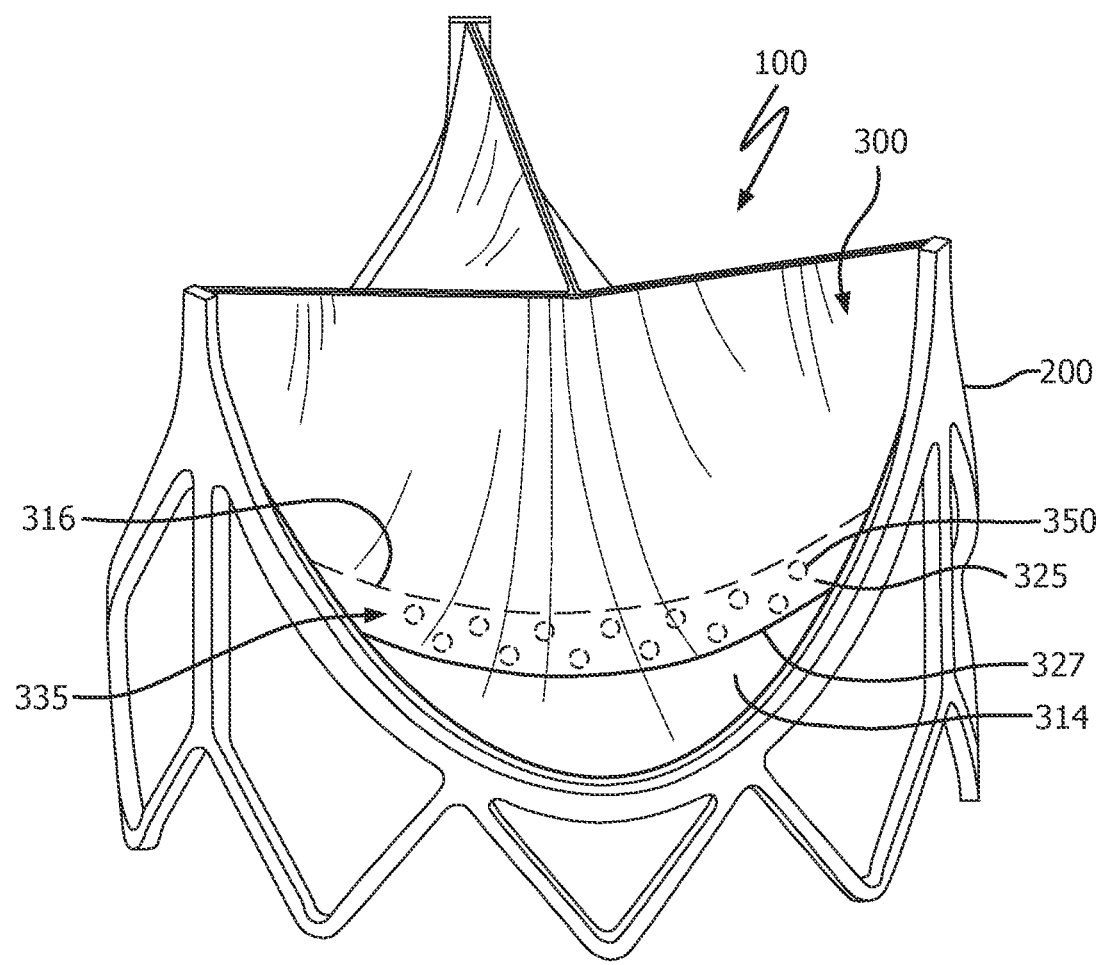
FIG. 3A is perspective view of a prosthetic valve, in accordance with another embodiment.
Figure 3B:
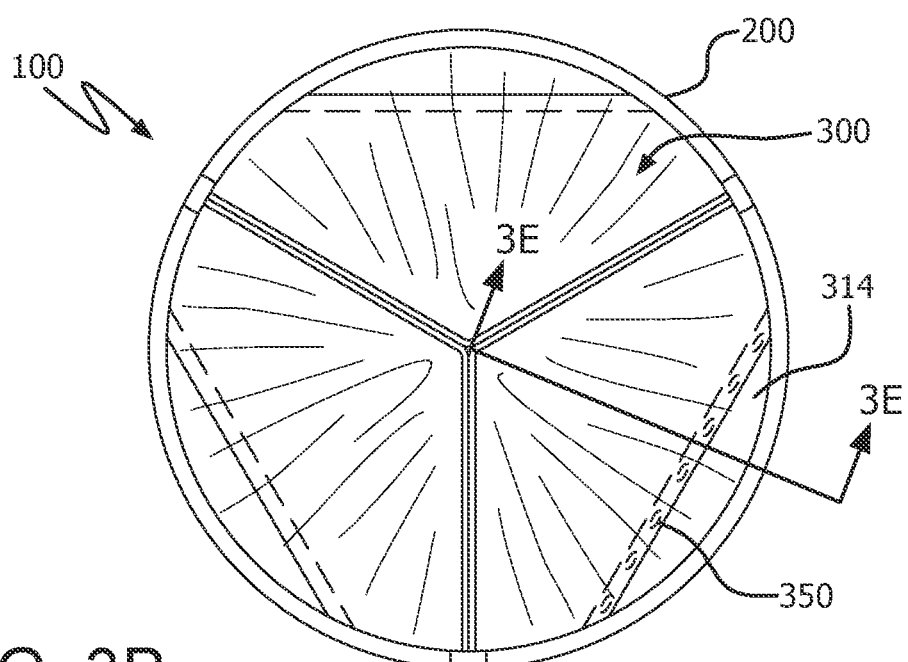
FIG. 3B is an axial view of the prosthetic valve of FIG. 3A in a closed position, in accordance with an embodiment.
Figure 3D:
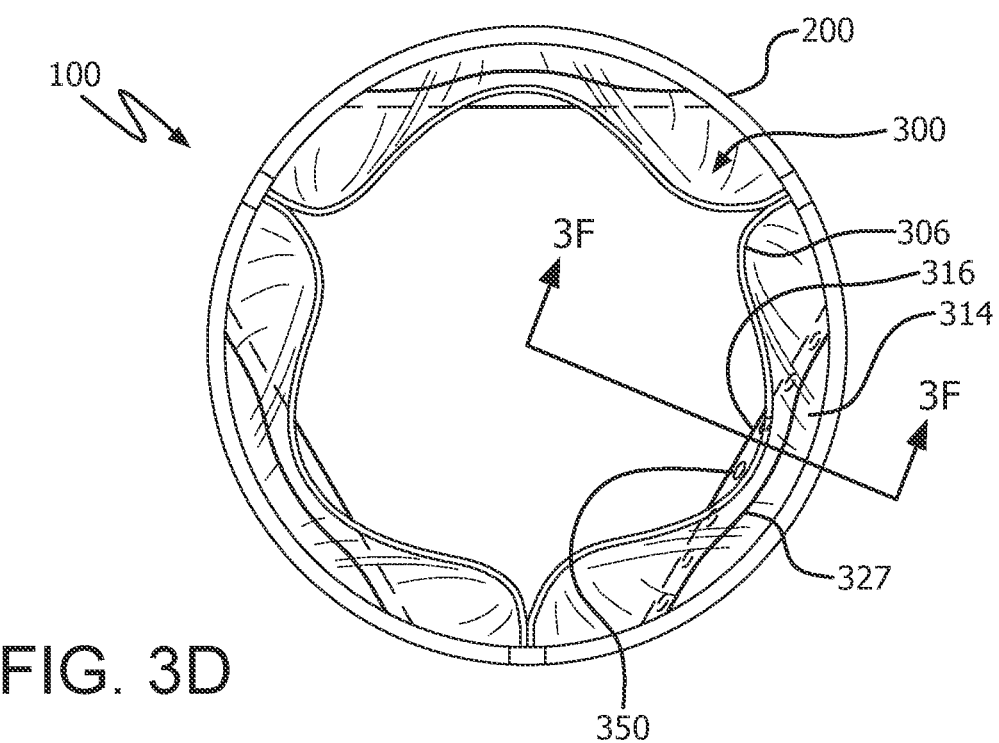
FIG. 3D is an axial view of the prosthetic valve FIG. 3C in an open position, in accordance with an embodiment.
Figure 3C:
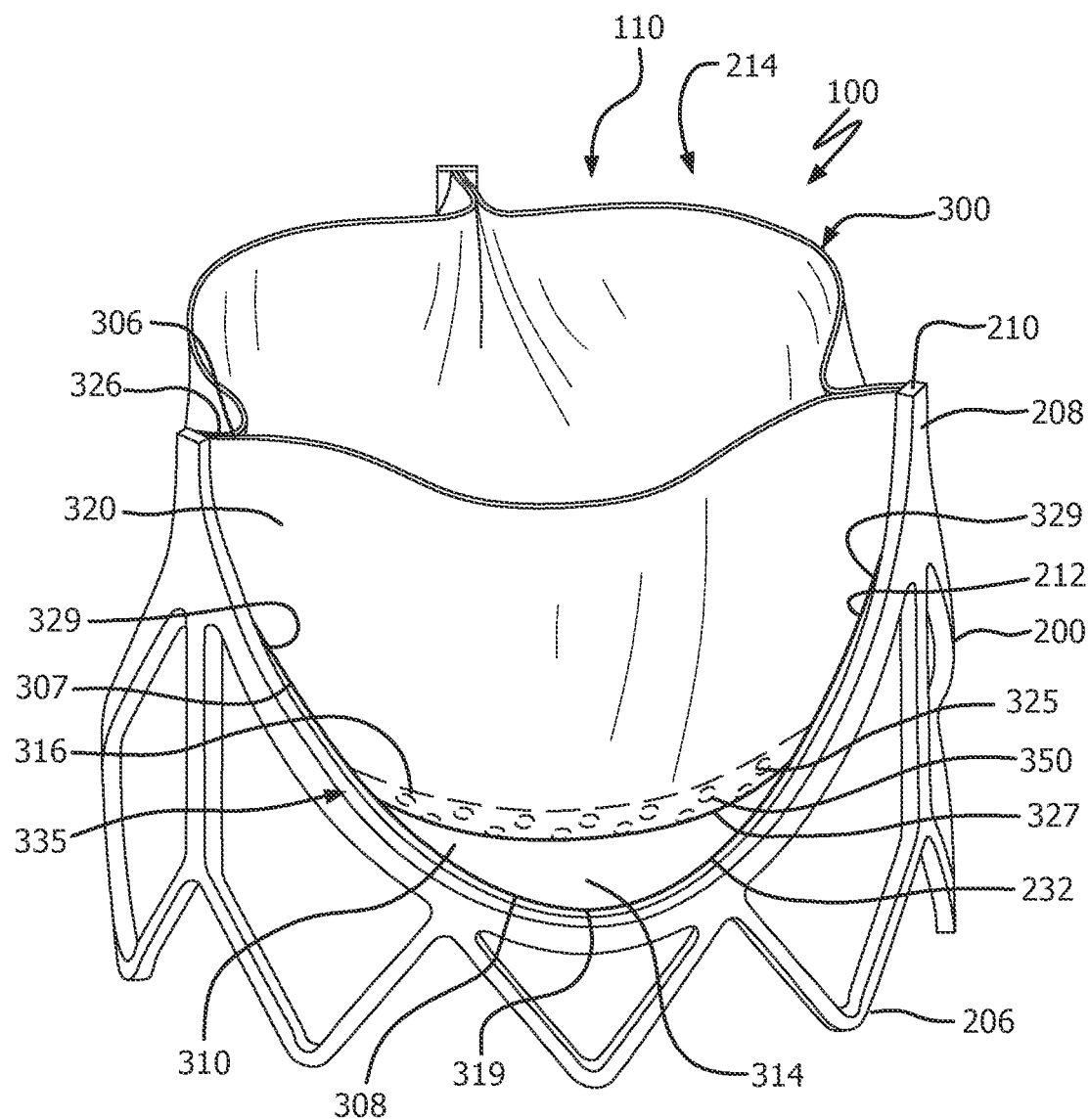
FIG. 3C is a perspective view of the prosthetic valve of FIG. 3A in an open position, in accordance with an embodiment.
Figure 3E:
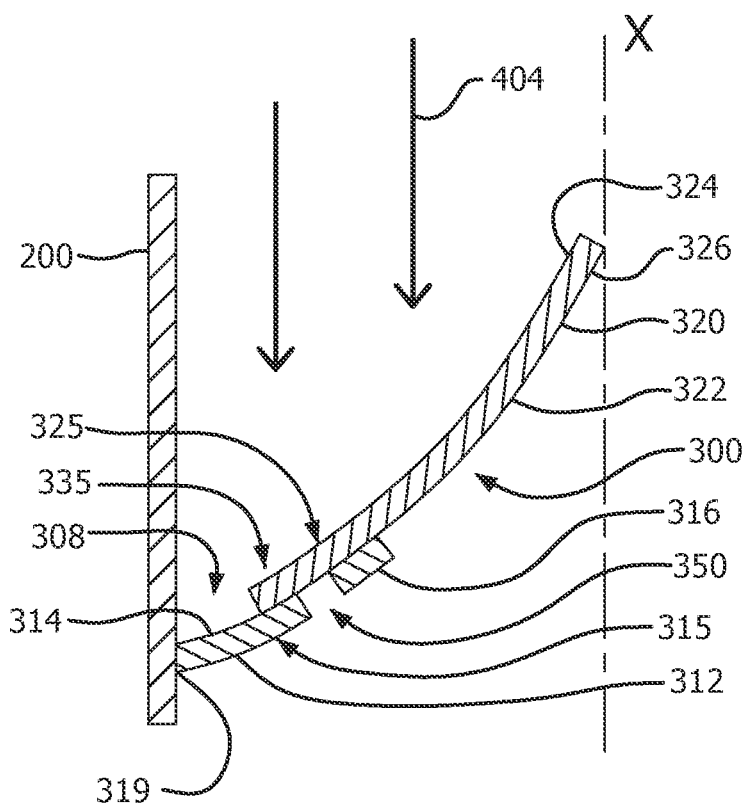
FIG. 3E is a cross-sectional view of the closed valve of FIG. 3B along cutline 3E-3E, in accordance with an embodiment.
Figure 3F:
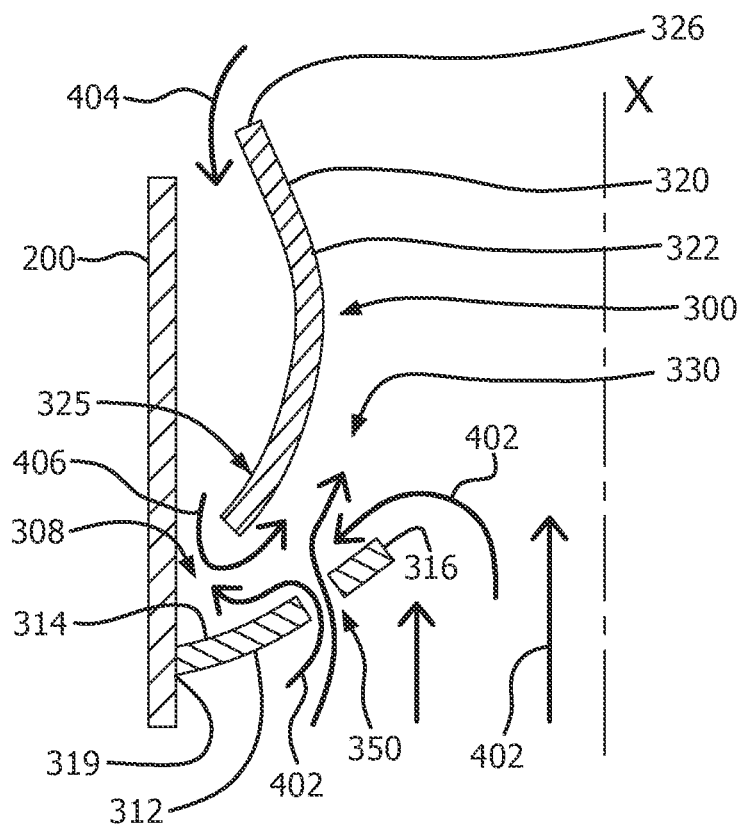
FIG. 3F is a cross-sectional view of the open valve of FIG. 3D along cutline 3F-3F, in accordance with an embodiment.

In accordance with another embodiment, FIGS. 3A and 3B are perspective and axial views, respectively, of a prosthetic valve 100 in a closed position. FIGS. 3C and 3D are perspective and axial views, respectively, of the prosthetic valve 100 in an open position, in accordance with the embodiment of FIGS. 3A and 3B. FIGS. 3E and 3F are cross-sectional views of the closed prosthetic valve 100 of FIG. 3B along cutline 3E-3E and of the prosthetic valve 100 of FIG. 3D along cutline 3F-3F, respectively. The first overlap region 315 comprises a plurality of apertures 350 extending from the first inflow side 312 to the first outflow side 314 operable to allow upstream flow to pass through the apertures 350 from the first inflow side 312 to the first outflow side 314 during fluid flow in the forward flow direction 402 when the leaflet 300 is not in the closed position. The apertures 350 in the first overlap region 315 provides, in part, that the first leaflet component 310 moves to the open position at a slower rate than the second leaflet component 320 ensuring that the gap 330 is formed therebetween. During retrograde flow, the second overlap region 325 is in sealing engagement with the apertures 350 when the leaflet 300 is in the closed position preventing fluid flow through the apertures 350 in the retrograde flow direction 404. Leakage of the fluid when the leaflet 300 is closed is known as regurgitation, or regurgitant flow.

Figure 4A:
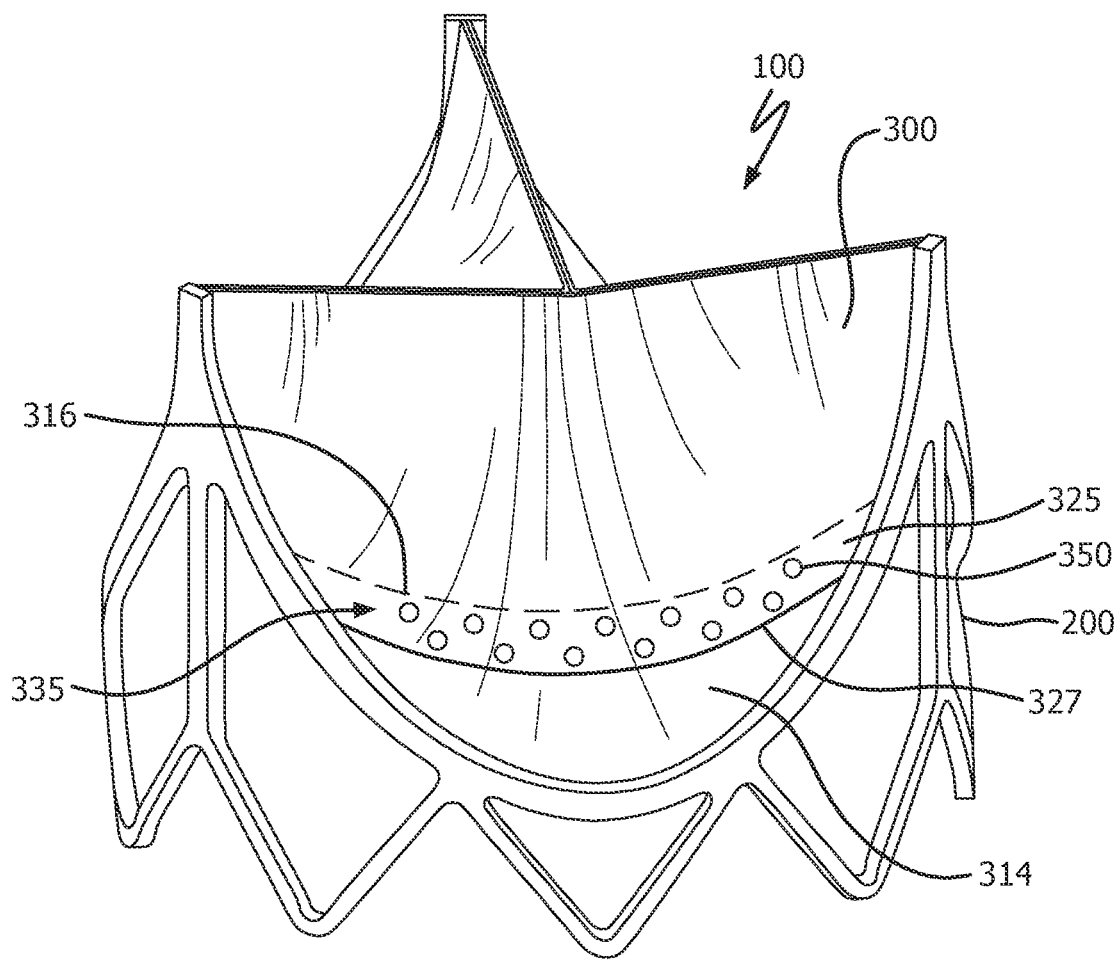
FIG. 4A is perspective view of a prosthetic valve, in accordance with another embodiment.
Figure 4B:
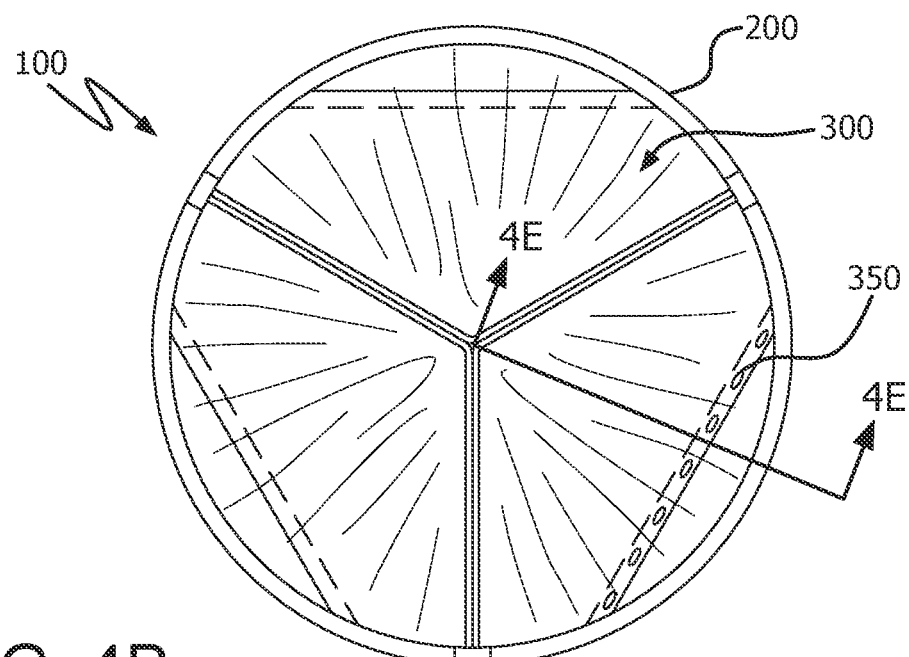
FIG. 4B is an axial view of the prosthetic valve of FIG. 4A in a closed position, in accordance with an embodiment.
Figure 4D:
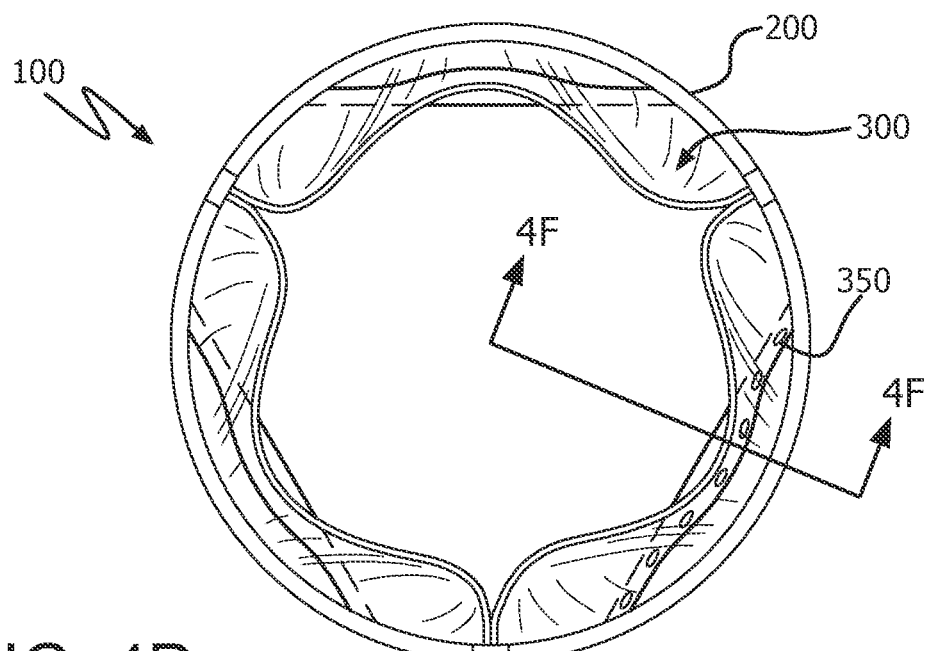
FIG. 4D is an axial view of the prosthetic valve FIG. 4C in an open position, in accordance with an embodiment.
Figure 4C:
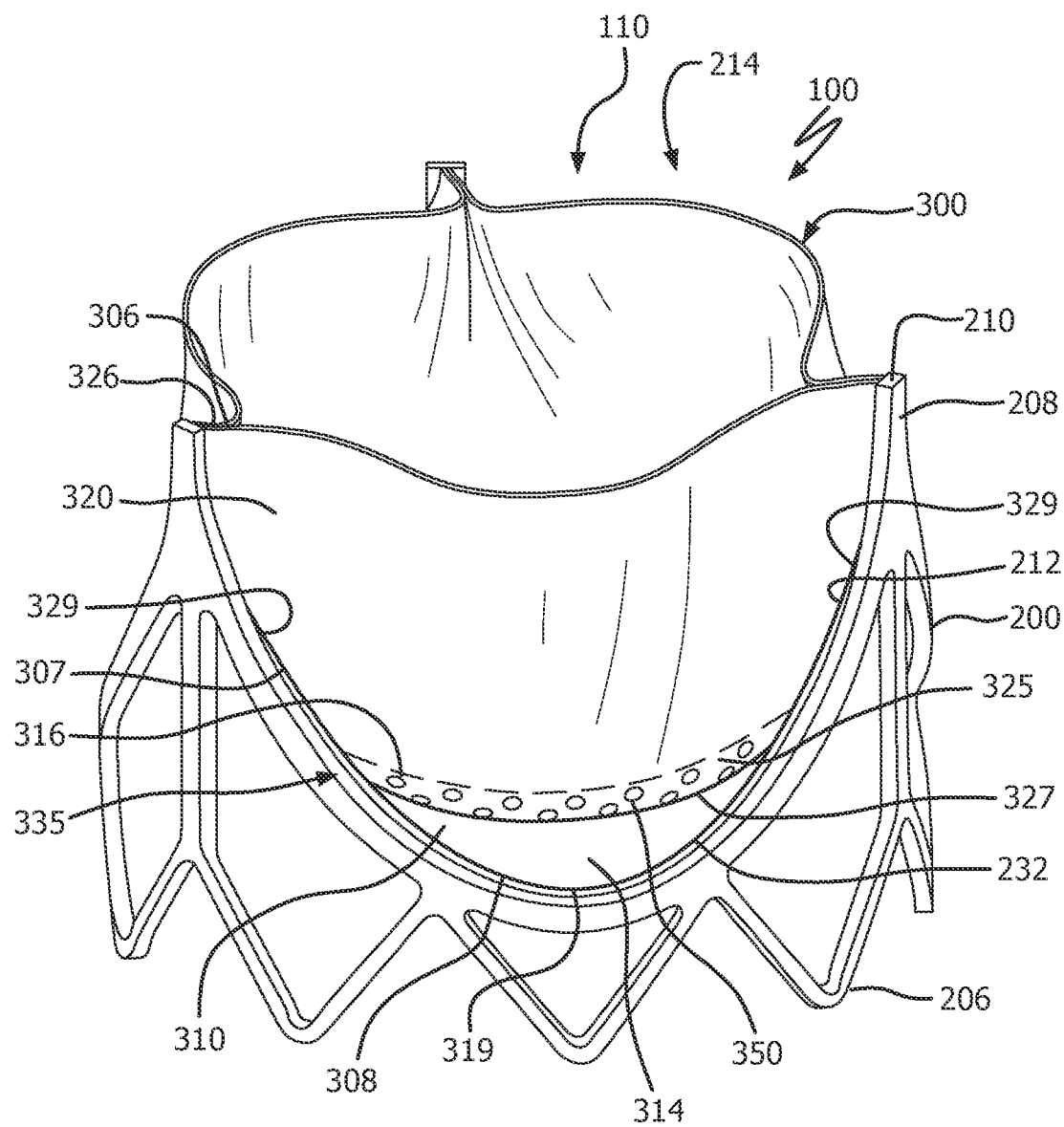
FIG. 4C is a perspective view of the prosthetic valve of FIG. 4A in an open position, in accordance with an embodiment.
Figure 4E:
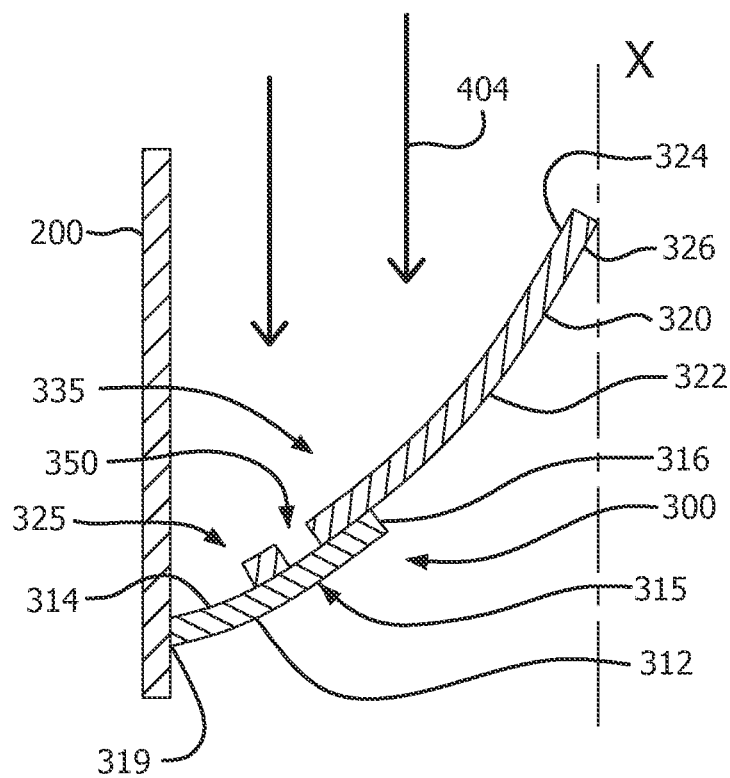
FIG. 4E is a cross-sectional view of the closed valve of FIG. 4B along cutline 4E-4E, in accordance with an embodiment.
Figure 4F:
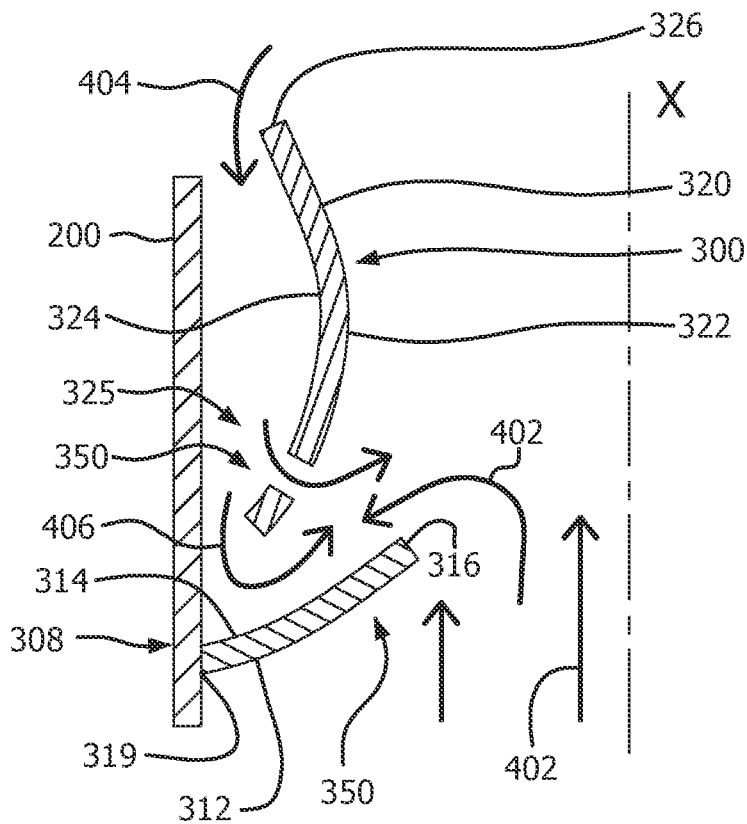
FIG. 4F is a cross-sectional view of the open valve of FIG. 4D along cutline 4F-4F, in accordance with an embodiment.

In accordance with another embodiment, FIGS. 4A and 4B are perspective and axial views, respectively, of a prosthetic valve 100 in a closed position. FIGS. 4C and 4D are perspective and axial views, respectively, of the prosthetic valve 100 in an open position, in accordance with the embodiment of FIGS. 4A and 4B. FIGS. 4E and 4F are cross-sectional views of the closed prosthetic valve 100 of FIG. 3B along cutline 4E-4E and of the prosthetic valve 100 of FIG. 4D along cutline 4F-4F, respectively. The second overlap region 325 comprises a plurality of apertures 350 extending from the second inflow side 322 to the second outflow side 324 operable to allow fluid adjacent the second outflow side 324 to pass through the apertures 350 from the second outflow side 324 to the second inflow side 322 during fluid flow when the leaflet 300 is not in the closed position.

The apertures 350 in the second overlap region 325, in part, augments the benefit of the gap 330 to further allow the flow of the fluid adjacent the second outflow side 324 to pass to the second inflow side 322. During reverse flow, the second overlap region 325 is in sealing engagement with the apertures 350 when the leaflet 300 is in the closed position preventing fluid flow through the apertures 350 in the retrograde flow direction 404, preventing regurgitation.

Figure 5:
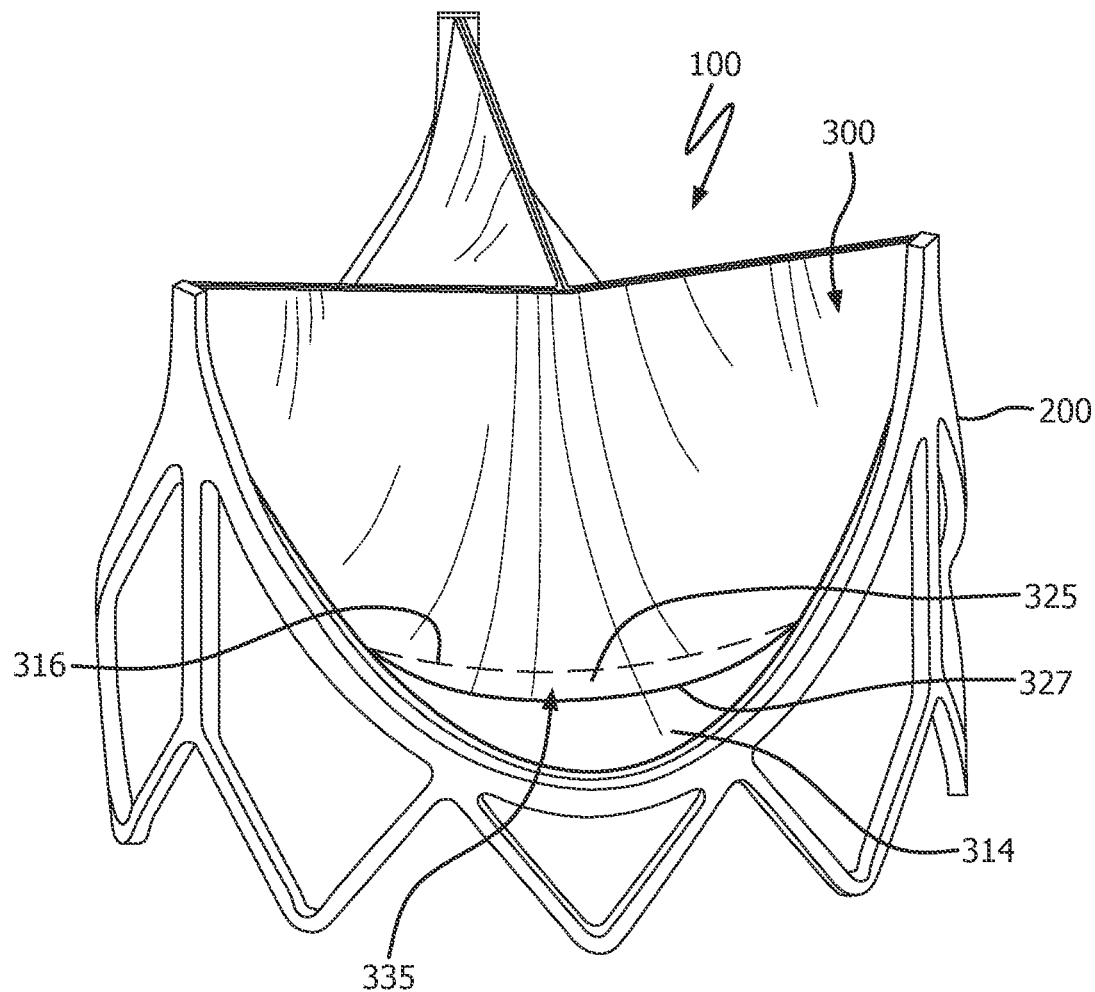
FIG. 5 is a perspective view of a prosthetic valve wherein the leaflet overlap region has a non-uniform width, in accordance with an embodiment.

In the embodiments of FIGS. 2A, 3A, and 4A, the leaflet overlap region 335 has a relatively uniform width. The first overlap region 315 and the second overlap region 325 defines a leaflet overlap region 335 that is relatively consistent in width from adjacent the frame 200 to away from the frame 200. FIG. 5 is a perspective view of a prosthetic valve 100 wherein the leaflet overlap region 335 has a non-uniform width, in accordance with an embodiment. In the embodiment of FIG. 5, the first overlap region 315 and the second overlap region 325 defines a leaflet overlap region 335 that tapers in width from a minimum adjacent the frame 200 to a maximum farthest away from the frame 200. As shown in FIG. 5, the leaflet overlap region 335 defines a width and a length, wherein the width has a non-uniform dimension along the width as defined by the first outflow free edge 316 having a concave profile. It is understood that the width of the overlap region 335, as defined by the degree of overlap between first overlap region 315 and the second overlap region 325 is predetermined for, among other things, to prevent prolapse of the second inflow free edge 327 and to ensure a sufficient sealing engagement between the first overlap region 315 and the second overlap region 325 when the leaflet 300 is in the closed position to prevent regurgitant flow due to downstream fluid pressure. Under certain downstream fluid pressure conditions, the first overlap region 315 and the second overlap region 325 may slip relative to each other with the potential of slipping out of engagement, or prolapsing, if the overlap region 335 is not sufficiently wide. It is understood that the frame 200 and/or the leaflet 300 will elastically deform under fluid pressure. Further, it is understood that the elastic deformation at the first outflow free edge 316 and the second inflow free edge 327 may be greater away from the attachment point to the frame 200. Therefore, the width of the overlap region 325 is predetermined to accommodate for the increase in deformation further away from the support provided by the frame 200.

As will be described later in reference to the embodiment of FIG. 6B, the first overlap region 315 and the second overlap region 325 define a leaflet overlap region 335 that tapers in width such that there is no overlap between the first leaflet component 310 and the second leaflet component 320 adjacent to and a predetermined distance away from the frame 200 which defines a regurgitant gap 331 of a predetermined size.

It is also understood that the degree of overlap between first overlap region 315 and the second overlap region 325 will also affect the size of the gap 330 and the degree of separation between the first outflow free edge 316 and the second inflow free edge 327 when the leaflet 300 is not in the closed position.

The relative size of the first leaflet component 310 and the second leaflet component 320 is predetermined for a particular purpose. In accordance with an embodiment, the first leaflet component 310 is made relatively small so as to not excessively extend into the lumen 214 of the frame 200, particularly if the first leaflet component 310 is relatively inflexible, so as to minimize the impediment to flow in the forward flow direction 402 through the prosthetic valve 100 when in the open position. It is understood that the relative size of the first leaflet component 310 and the second leaflet component 320 will determine, in part, the characteristics of the pattern of flow in the forward flow direction 402 and the pattern of flow in the recirculating direction, that is, recirculating flow 406, which will also, in part, determine the dynamics of the first leaflet component 310 and the second leaflet component 320. It has been found in some embodiments that as the first leaflet component 310 extends further into the lumen 214, the second leaflet component 320 may begin to flutter when in the open position during forward flow conditions.

Related to the relative size of the first leaflet component 310 and the second leaflet component 320 is the axial location X1 of the overlap region 335 relative to the upstream-most location of the leaflet base 308. In general, wherein the axial location X1 increases away from the inflow end 206 and closer to the outflow end 208, the first leaflet component 310 will extend further into the lumen 214 of the frame 200 and thus affect the characteristics of the flow in the forward flow direction 402.

Figure 6A:
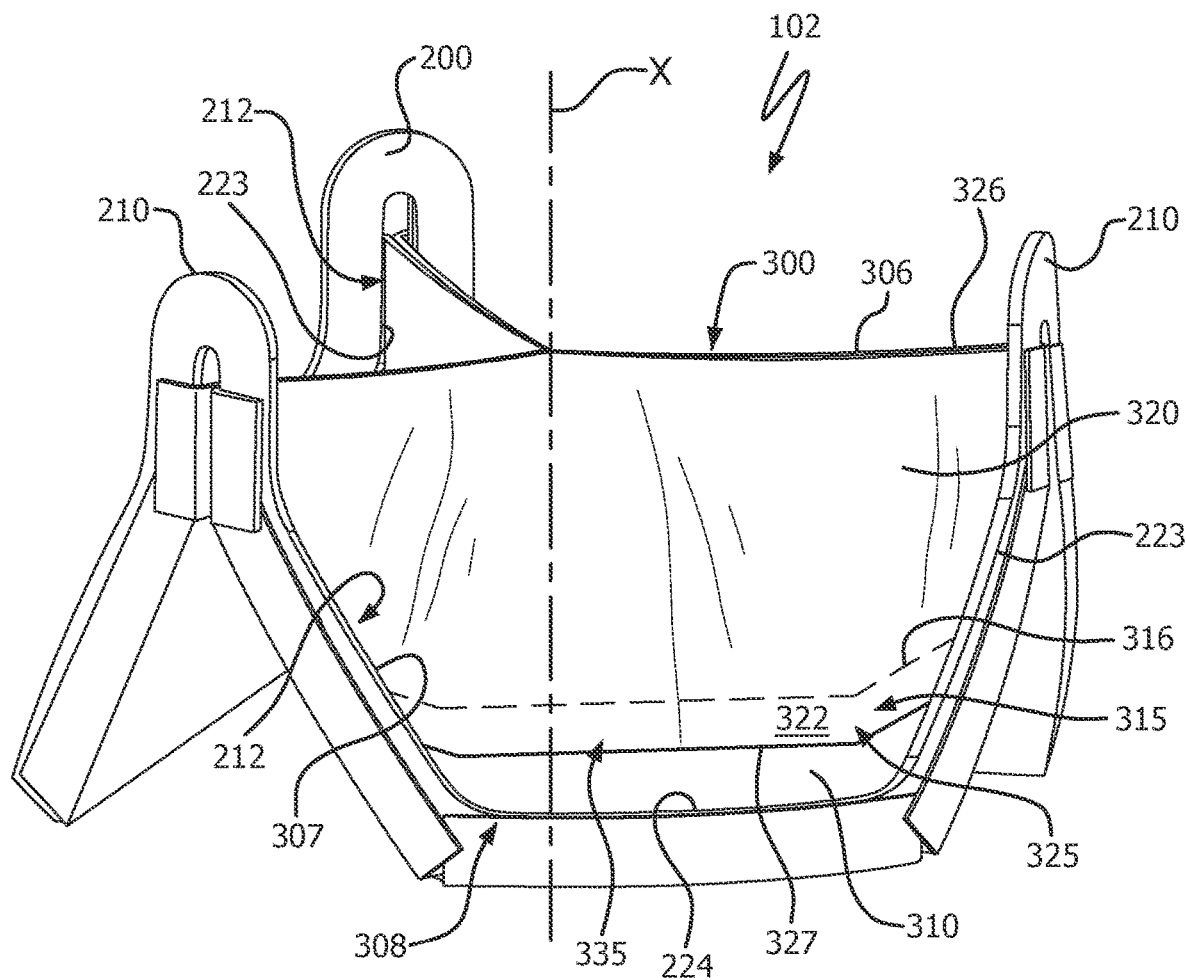
FIG. 6A is a perspective view of a prosthetic valve having a frame and a plurality of leaflets each having a first leaflet component and a second leaflet component defining a shape substantially that of an isosceles trapezoid, in accordance with an embodiment.

The shape of the leaflets 300 are defined, at least in part, by the shape of the frame 200 at the leaflet attachment region 212 and the leaflet free edge 306, as shown in FIG. 2A. In the embodiments of the prosthetic valve 100 shown in FIGS. 2A-2F, 3A-3F, 4A-4F, and 5, the shape of the leaflet 300, and corresponding leaflet attachment region 212 of the frame 200, is substantially that of a parabola. The leaflet 300 may define a shape that is predetermined for a particular purpose. FIG. 6A is a perspective view of a prosthetic valve 102 having a frame 200 and a plurality of leaflets 300 each having a first leaflet component 310 and a second leaflet component 320 defining a shape substantially that of an isosceles trapezoid, in accordance with an embodiment. It has been found that leaflets 300 defining a shape substantially that of an isosceles trapezoid has improved bending dynamics as compared to that of a parabola. Improved bending dynamics of thin, flexible leaflets may include, but are not limited to, reduced creasing and wrinkling and faster opening and closing response to fluid pressure changes.

Figure 6B:
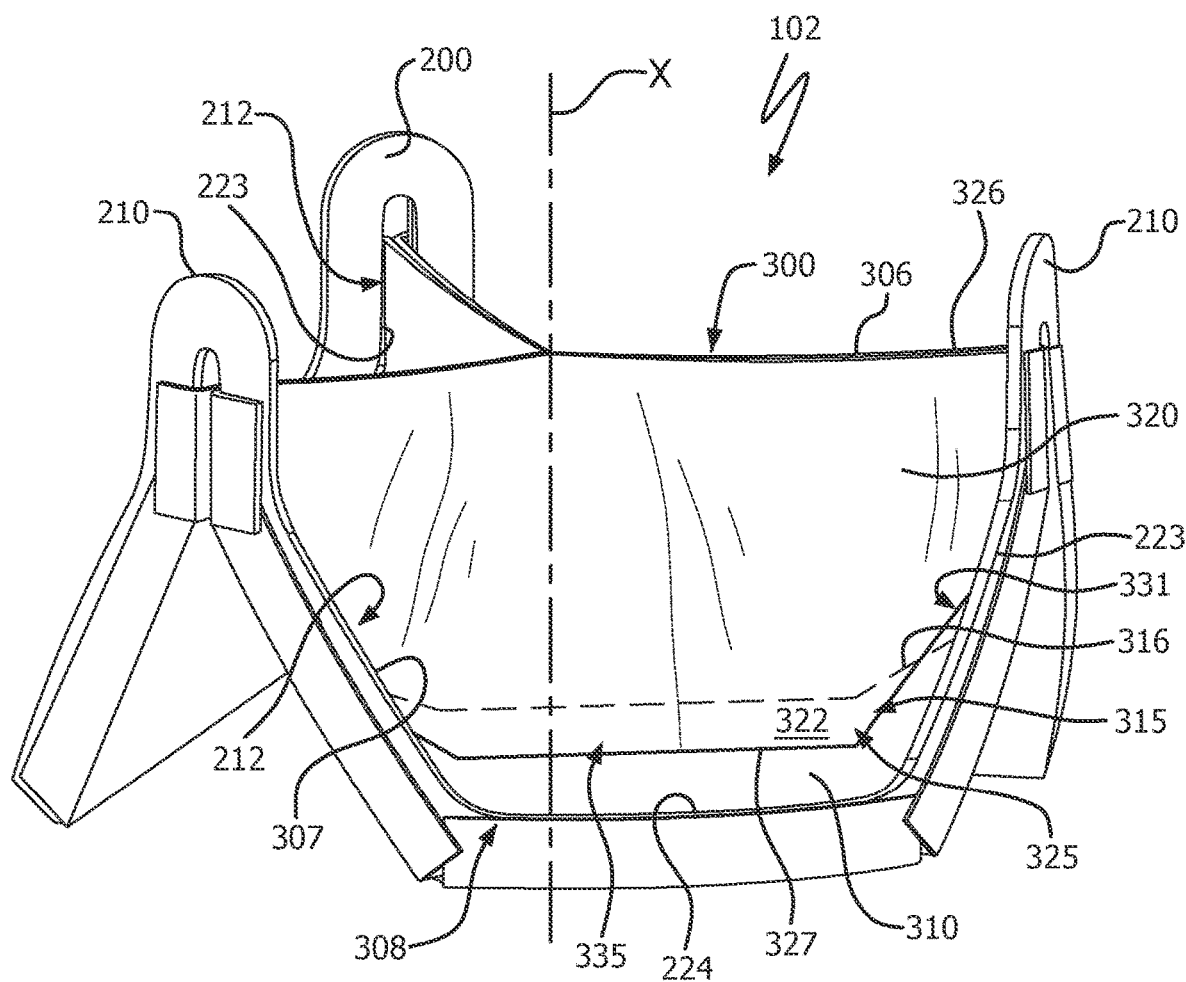
FIG. 6B is a perspective view of a prosthetic valve having a frame and a plurality of leaflets each having a first leaflet component and a second leaflet component defining a shape substantially that of an isosceles trapezoid, in accordance with an embodiment.

FIG. 6B is a perspective view of a prosthetic valve 102 having a frame 200 and a plurality of leaflets 300 each having a first leaflet component 310 and a second leaflet component 320 defining a shape substantially that of an isosceles trapezoid, in accordance with an embodiment. The first overlap region 315 and the second overlap region 325 define a leaflet overlap region 335 that tapers in width such that there is no overlap adjacent to and a predetermined distance away from the frame 200 defining a regurgitant gap 331 of a predetermined size. The regurgitant gap 331 allows a predetermined amount of retrograde flow to pass through the regurgitant gap 331 when the prosthetic valve 102 is closed. The regurgitant gap 331 is operable to prevent pinching or creasing of the first outflow free edge 316 and the second inflow free edge 327 at the frame attachment location adjacent the regurgitant gap when the leaflet 300 is in the closed position. Additionally, the regurgitant gap 331 may assist in preventing fluid stagnation at the location of the regurgitant gap 331 so at to prevent thrombus formation.

Figure 7:
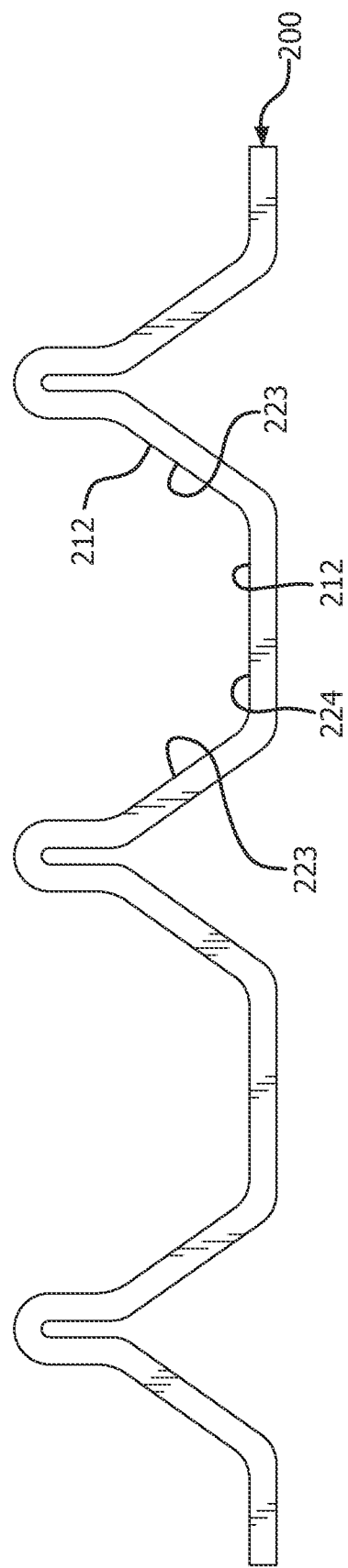
FIG. 7 is a plan view of the frame of the embodiment of FIGS. 6A and 6B unrolled to a flat profile.

FIG. 7 is a plan view of a frame 200 unrolled to a flat profile to better visualize the shape of the frame components, in accordance with the embodiment of FIG. 6. The frame 200 comprises a leaflet attachment region 212 that has substantially the shape of three sides of an isosceles trapezoid having two leaflet attachment sides 223, and a leaflet attachment base 224.

Figure 8:
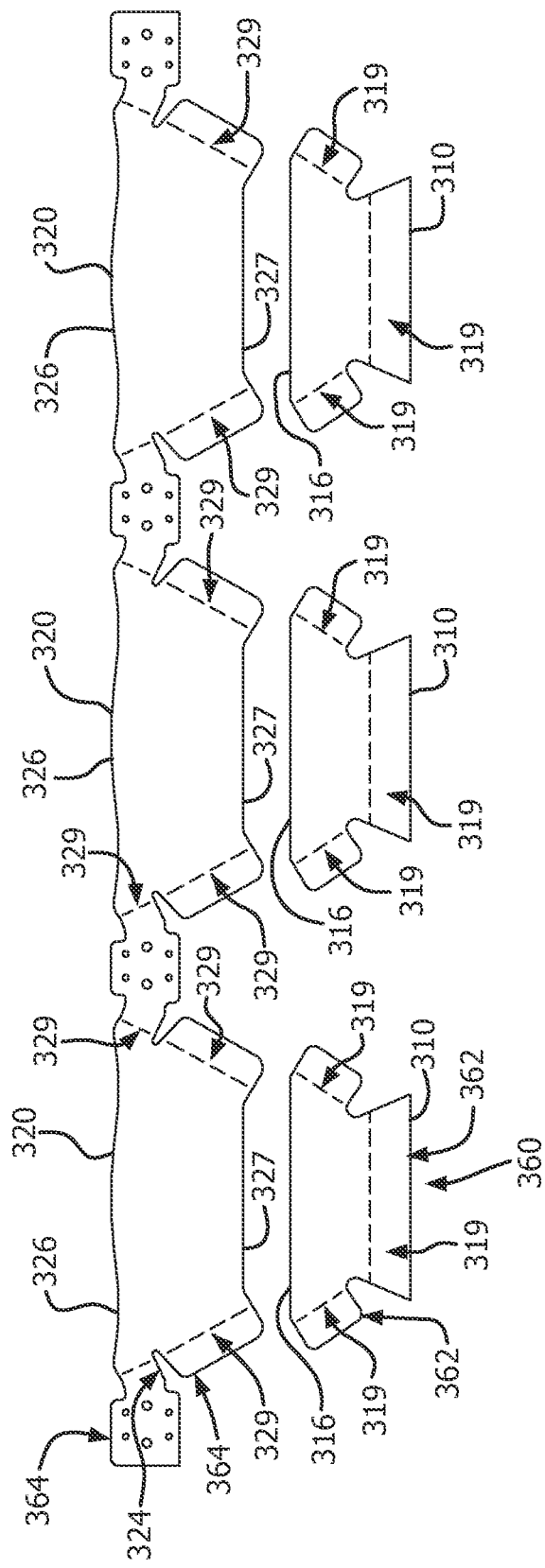
FIG. 8 is a plan view of a leaflet pattern comprising a plurality of first leaflet components and second leaflet components, in accordance with an embodiment.

The leaflets 300 comprising the first leaflet component 310 and the second leaflet component 320 may be made in a number of different ways. In accordance with an embodiment, each leaflet 300 is made as a single pair including a first leaflet component 310 and a second leaflet component 320. In accordance with another embodiment, as shown in FIG. 8, a plurality of leaflets 300, and in particular, a plurality of second leaflet components 320, may be made from a single leaflet pattern. By way of example, a leaflet pattern comprising a plurality of leaflets can be made by starting with a cylinder of biological or synthetic material and cutting the cylinder into a pattern that defines the leaflets.

FIG. 8 is a plan view of a leaflet pattern 360 comprising a plurality of first leaflet components 310 and second leaflet components 320, in accordance with an embodiment. The leaflet pattern 360 may be made from a flat sheet of material cut into a leaflet pattern 360 and subsequently rolled into a cylindrical shape or cut from a cylindrical component to correspond to the cylindrical shape of the frame 200. In accordance with another embodiment, the leaflet pattern 360 may be formed is by compression or injection molding. The second leaflet components 320 may be linked together via second tabs 364.

Referring to FIG. 8, the first leaflet component 310 comprises a first frame attachment edge 319 and a first outflow free edge 316. The first frame attachment edge 319 includes a plurality of first tabs 362 that couple to components of the frame 200 in a wrap-around fashion in accordance with an embodiment, as shown by way of example in FIG. 6. The second leaflet component 320 comprises a second inflow free edge 327, a second outflow free edge 326, and second frame attachment edges 329. The second frame attachment edge 329 includes a plurality of second tabs 364 that couple to components of the frame 200 in a wrap-around fashion.

Although some of the embodiments described herein provide, by way of example, attachment edges including tabs that couple to the frame, it is understood and appreciated that the leaflets may be coupled to the frame in many ways known in the art. By way of example, but not limited thereto, the leaflets may be coupled to the frame using mechanical elements, such as, but not limited to, those associated with posts, hooks, and suture, and using other means such as, but not limited to, heat bonding, gluing, molding and crimping. Embodiments presented herein are not limited by the particular coupling means used to couple the leaflet, and corresponding leaflet components, to the frame or other support structure.

As provided above, the shape of the leaflets 300 are defined, at least in part, by the shape of the frame 200 at the leaflet attachment region 212 and the leaflet free edge 306. The shape of the leaflets 300 can also be defined by the processes used to manufacture the prosthetic valve 100, such as, but not limited, those described below. For example, in accordance with an embodiment, the shape of the leaflets 300 depends in part on making the leaflets 300 using molding and trimming processes to impart a predetermined shape to the leaflets 300.

Figure 9:
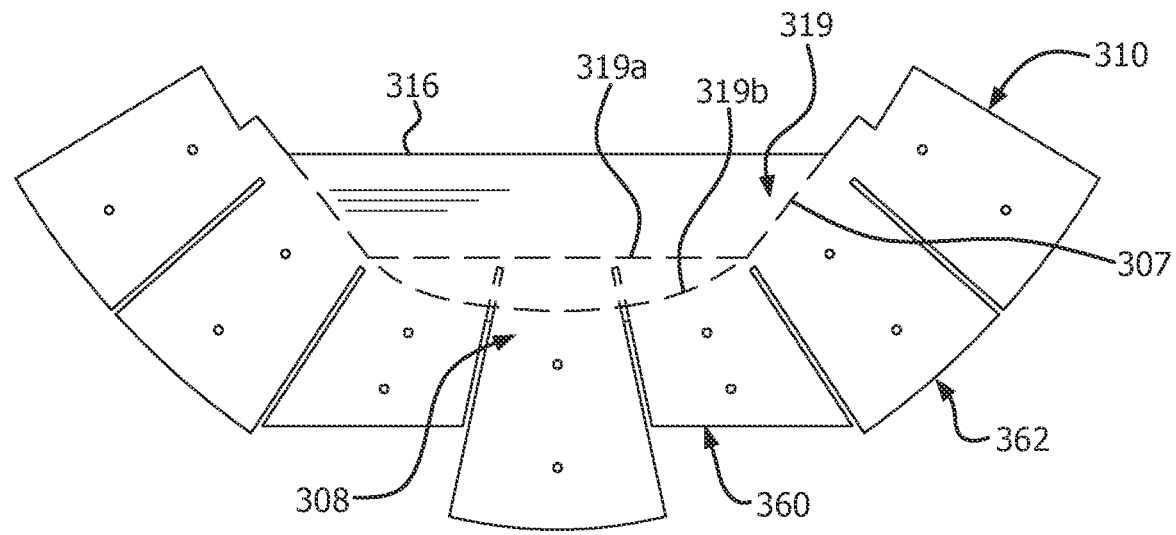
FIG. 9 is a plan view of a leaflet pattern comprising a plurality of first leaflet components, in accordance with an embodiment.
Figure 10:
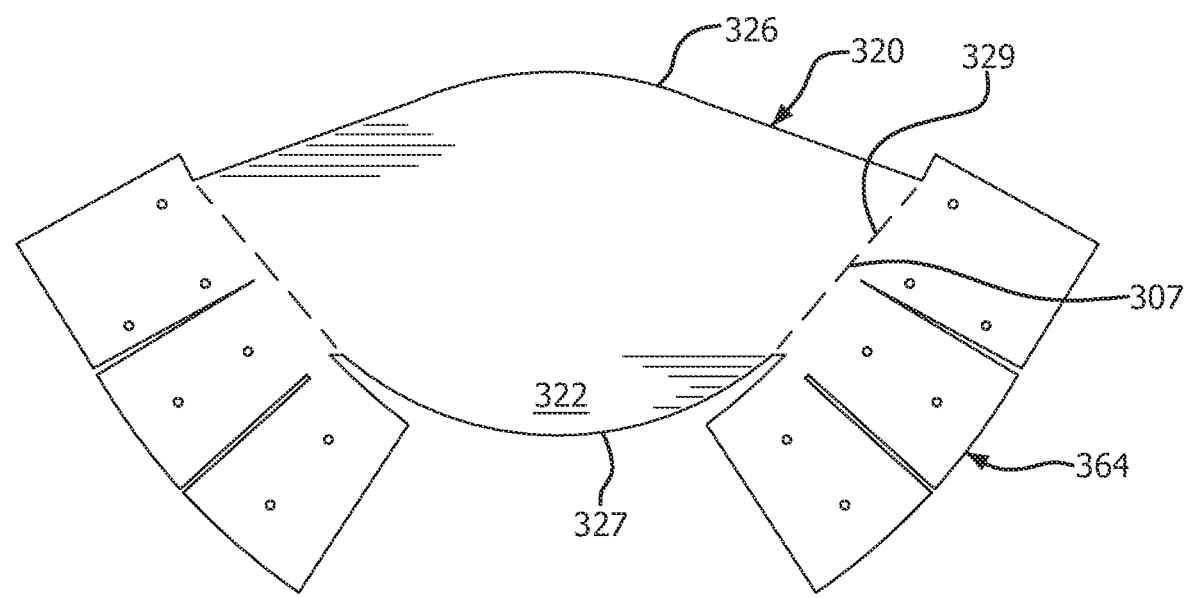
FIG. 10 is a plan view of a leaflet pattern comprising a plurality of second leaflet components, in accordance with an embodiment.

FIGS. 9 and 10 are plan views of a leaflet pattern 360 comprising a first leaflet component 310 and a second leaflet component 320, respectively, in accordance with an embodiment. The first leaflet component 310 comprises a first frame attachment edge 319 and a first outflow free edge 316. The first frame attachment edge 319 includes a plurality of first tabs 362 that are operable to couple to components of the frame 200 adjacent the leaflet attachment base 224 and at least a portion of the two leaflet attachment sides 223, as shown in FIGS. 2A, 6 and 7. The first frame attachment edge 319 defines a shape of a portion of the leaflet sides 307 and the leaflet base 308, in that the two leaflet sides 307 diverge from the leaflet base 308. FIG. 9 shows two alternative embodiments for the leaflet base 308 in dashed lines, a straight first frame attachment edge 319a, corresponding to the frame 200 of FIG. 7, and a parabolic first frame attachment edge 319b, suitable for a parabolic leaflet attachment base 224 corresponding to the frame 200 of FIG. 2A. During the opening and closing of the leaflet 300, the first leaflet component 310 will bend about the leaflet base 308. Bending about the straight first frame attachment edge 319a may be in a more controlled manner that may reduce wrinkling and/or fluttering of the first leaflet component 310 as compared with bending about the parabolic first frame attachment edge 319b.

The second leaflet component 320 comprises a second inflow free edge 327, a second outflow free edge 326, and two second frame attachment edges 329 that diverge from the second inflow free edge 327. The second frame attachment edges 329 include a plurality of second tabs 364 that couple to components of the frame 200 adjacent each of the two leaflet attachment sides 223. The first outflow free edge 316 of the first leaflet component 310 is operable to overlap the second inflow side 322 of the second inflow free edge 327 of the second leaflet component 320 to define an overlap region 315, as shown in the embodiment of FIG. 6, and similarly for the embodiment of FIG. 2A. The shape of the second inflow free edge 327 is predetermined by the shape of the first outflow free edge 316 and the desired width of the overlap region 315, suitable for a particular purpose.

In accordance with embodiments, as exemplified in FIGS. 2A, 3A, 4A, 5, 6A, wherein the second leaflet component 320 has a second inflow free edge 327 being not coupled to the leaflet attachment base 224 of the frame 200, it has been found that the second leaflet component 320 has improved bending dynamics as compared to that of a parabolic leaflet 30 such as shown in FIG. 1A. The benefits of improved bending dynamics of the leaflet second component 320 may include, but are not limited to, reduced creasing and wrinkling, reduced fluttering, faster opening and closing response to fluid pressure changes, and an increase in durability.

In the previous embodiments, the first leaflet component 310 and the second leaflet component 320 are generally located upstream and downstream on the frame 200, respectively, defining a single gap 330 generally extending across the leaflet 300 perpendicular to the axis X of the prosthetic valve 100, as shown in FIG. 2F. It may be advantageous to provide a leaflet with more than one gap 330 for a predetermined flow dynamic behind the leaflet.

Figure 11A:
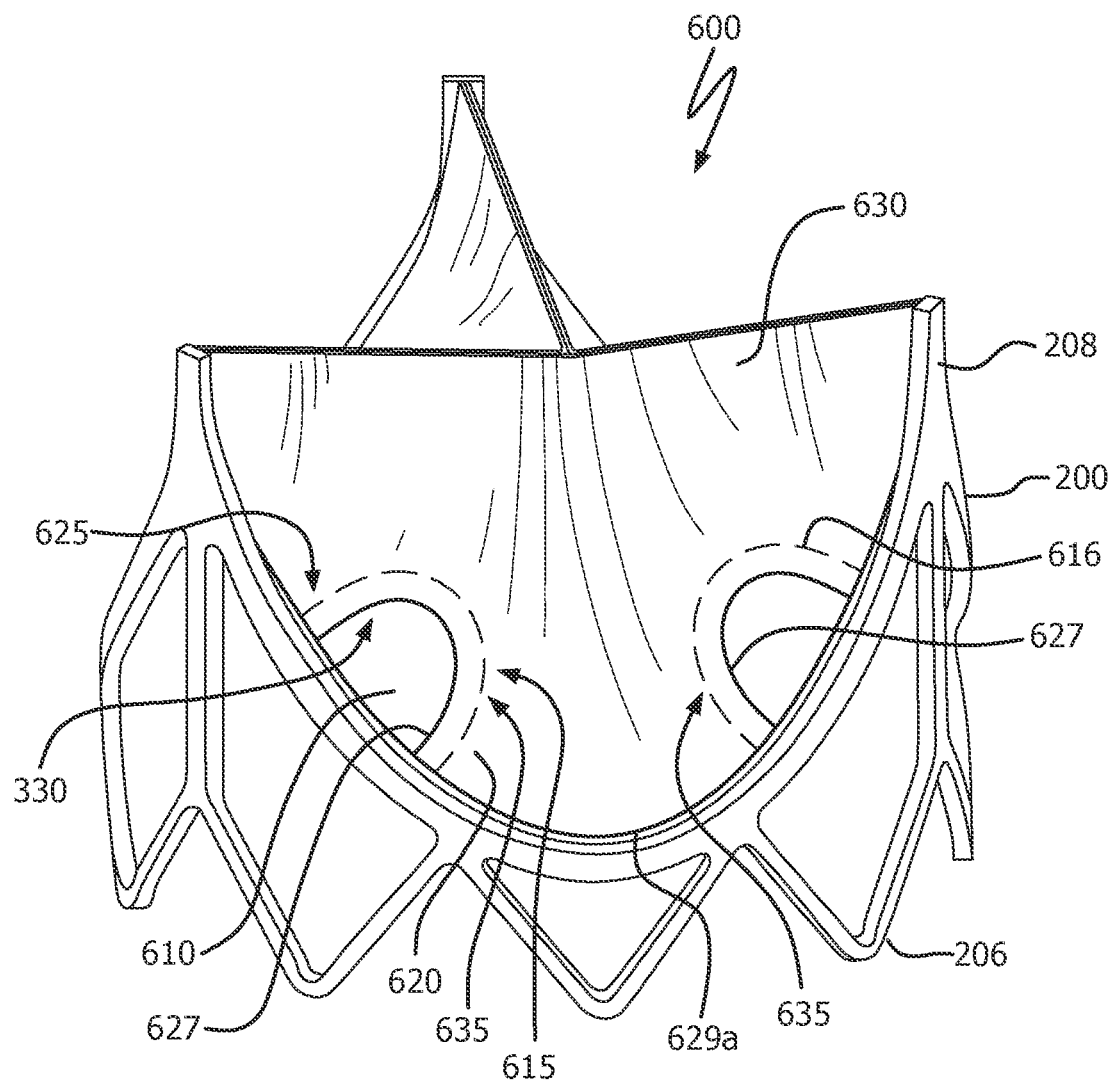
FIG. 11A is a perspective view a prosthetic valve having a frame and a plurality of leaflets each having a plurality of first leaflet components that overlap the second inflow side of a second leaflet component, in accordance with an embodiment.

FIG. 11A is a perspective view a prosthetic valve 600 having a frame 200 and a plurality of leaflets 630 each having a plurality of first leaflet components 610 that overlap a second inflow side 622 of a second leaflet component 620, in accordance with an embodiment. Similarly to the embodiment of FIGS. 2E and 2F, a gap 330 formed between the first leaflet component 610 and the second leaflet component 620 when the leaflet 630 is not in the closed position allows fluid adjacent the first outflow side 614 and the second outflow side 624 to pass through the gap 330 during fluid flow in the forward flow direction 402 through the lumen 214. That is, the recirculating flow 406 behind the leaflet 630 may pass through the gap 330 preventing the recirculating flow 406 from slowing down or stagnating behind the leaflet 300. Further, the gap 330 also allows fluid flow in the forward flow direction 402 to pass through the gap 330 from the first inflow side 612 and the second inflow side 622 further disrupting and displacing the recirculating flow 406 behind the leaflet 630 to downstream of the leaflet 630. Thus, fluid behind the leaflet 630 is less likely to clot or form thrombus, particularly at the leaflet base 608 and where it attaches to the frame 200. In this embodiment, the first leaflet component 610 comprises a material with a high modulus such that it resists bending under the anticipated flow conditions. Since the first leaflet component 610 is not supported by the second leaflet component 320 at the overlap region 625 when in the closed position, the first leaflet component 610 must resist the back pressure of the fluid when in the closed position to prevent prolapse.

Figure 12A:
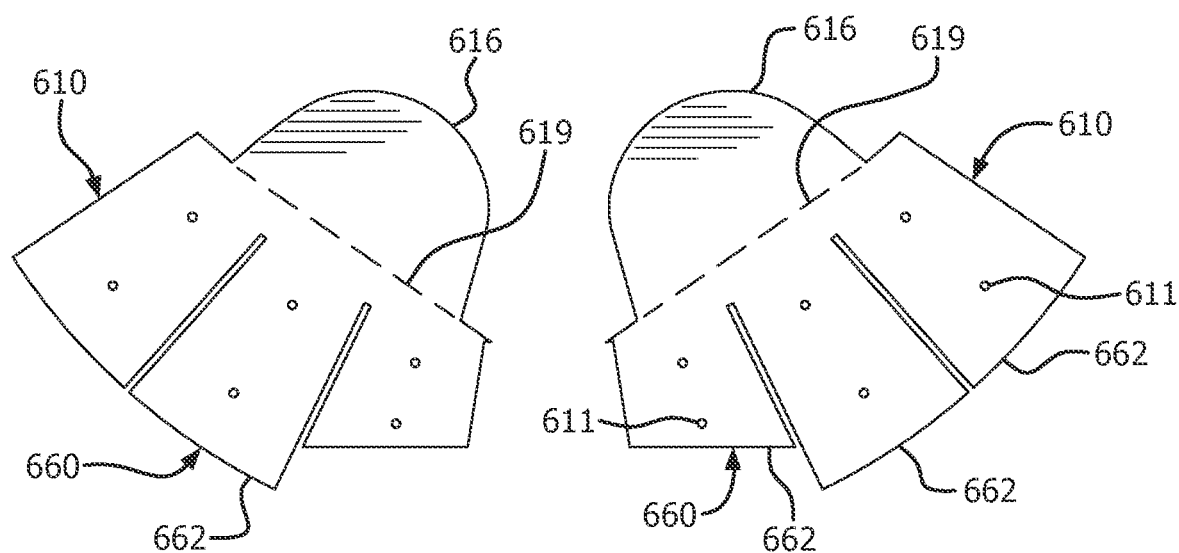
FIG. 12A is a plan view of a leaflet pattern comprising a plurality of first leaflet components, in accordance with an embodiment.
Figure 13:
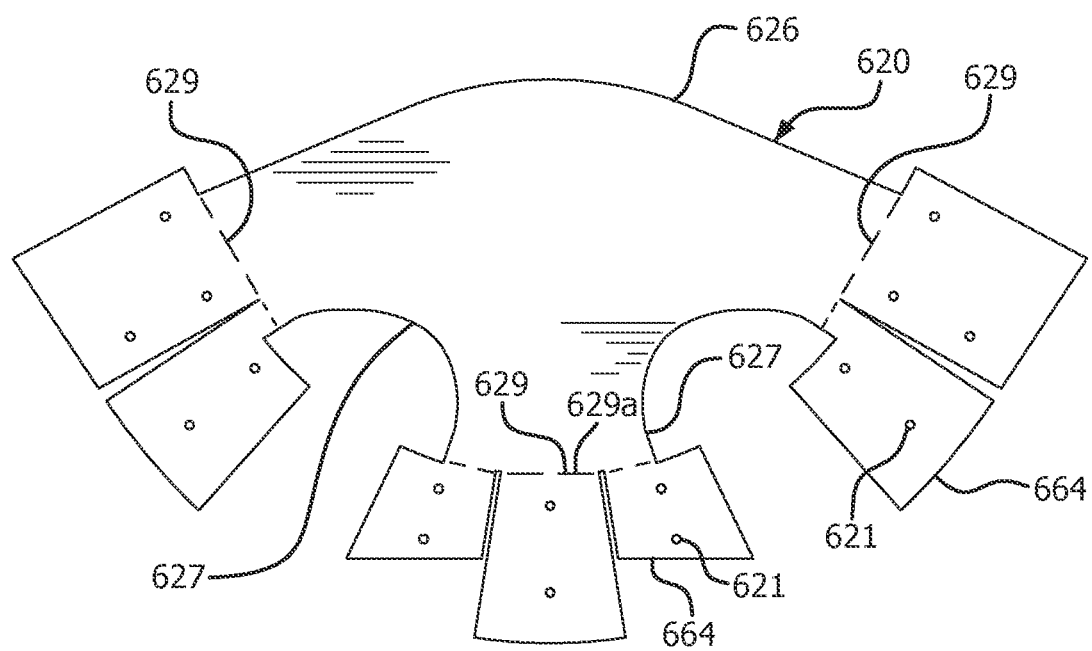
FIG. 13 is a plan view of a leaflet pattern comprising a plurality of second leaflet components, in accordance with an embodiment.

FIGS. 12A and 13 are plan views of a leaflet pattern 660 comprising a plurality of first leaflet components 610 and second leaflet components 620, respectively, in accordance with an embodiment. Referring to FIG. 12A, each of the first leaflet components 610 comprise a first frame attachment edge 619 and a first outflow free edge 616. The first frame attachment edge 619 includes a plurality of first tabs 662 that couple to components of the frame 200.

The second leaflet component 620 comprises a plurality of second inflow free edges 627, a second outflow free edge 626, and three second frame attachment edges 629. The second frame attachment edges 629 include a plurality of first tabs 662 that couple to components of the frame 200. Alignment of each of the first leaflet components 610 relative to the second leaflet component 620 is provided by locating first tab apertures 611 on first tabs 662 with second tab apertures 621 on second tabs 664.

The leaflets 630 comprise multiple first leaflet components 610, in this embodiment, two first leaflet components 610, and a second leaflet component 620 defining two second inflow free edges 627. The second leaflet component 620 is coupled to the frame 200 along second frame attachment edges 629. A first leaflet component 610 is coupled to the frame 200 along the first frame attachment edge 619 adjacent each of the second inflow free edges 627 so as to define a gap 330 therebetween when the leaflet 630 is open. In accordance with an embodiment, the first outflow free edge 616 of the first leaflet component 610 is located adjacent to and overlaps the second inflow side 622 of the second inflow free edge 627 to define the overlap region 625. Because of the specific location of the gap 330, the gap 330 will close in sealing engagement at the overlap region 625, shown in FIG. 11B, to prevent regurgitent flow when the leaflet 630 is in the closed position.

In accordance with the embodiment of FIG. 11A, the upstream-most second frame attachment edge 629a provides additional support to the second inflow free edges 627 such that they do not prolapse when in the closed position resisting downstream flow pressure. The length of the upstream-most second frame attachment edge 629a is sized for a particular purpose.

Figure 11B:
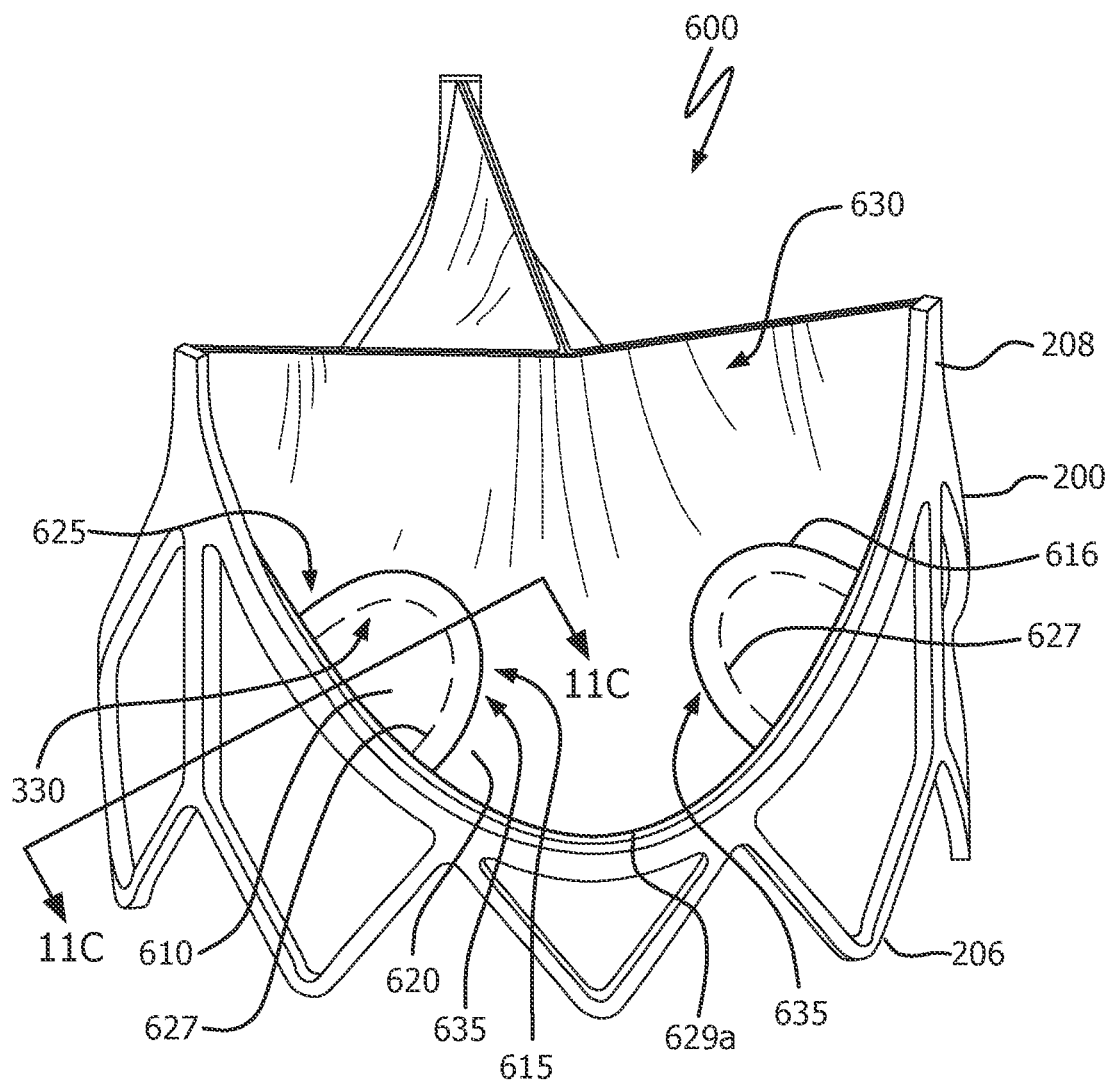
FIG. 11B is a perspective view a prosthetic valve having a frame and a plurality of leaflets each having a plurality of first leaflet components that overlap the second outflow side of a second leaflet component, in accordance with another embodiment.
Figure 11C:
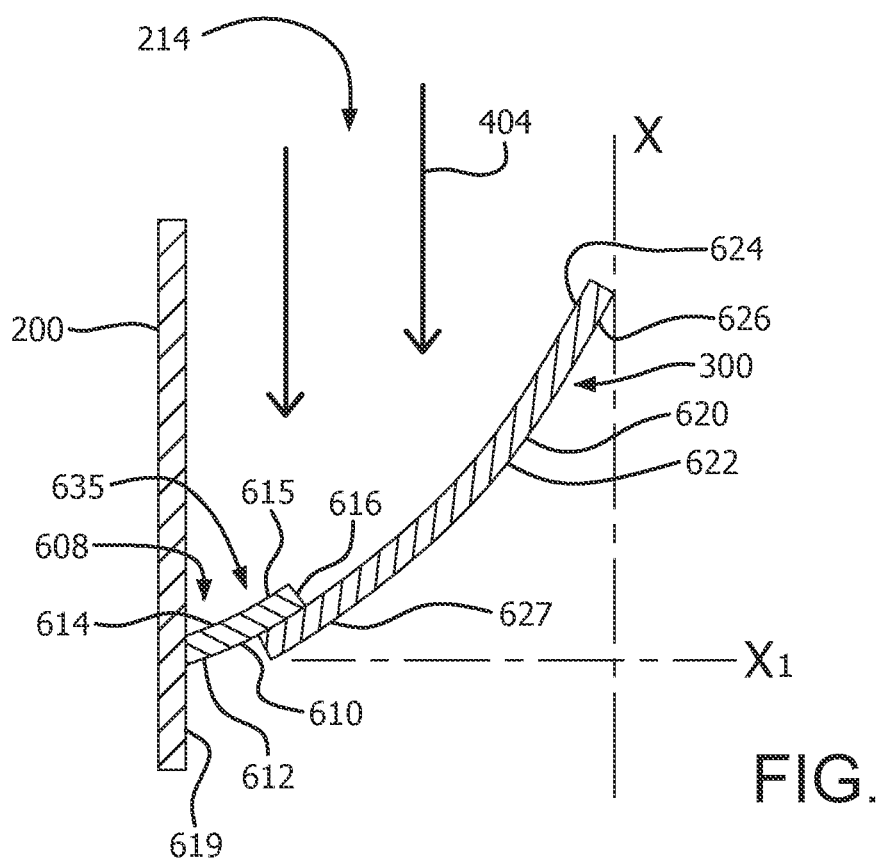
FIG. 11C is a cross-sectional view along cut-line 110 of the embodiment of FIG. 11B when the leaflet is in the closed position.
Figure 11D:
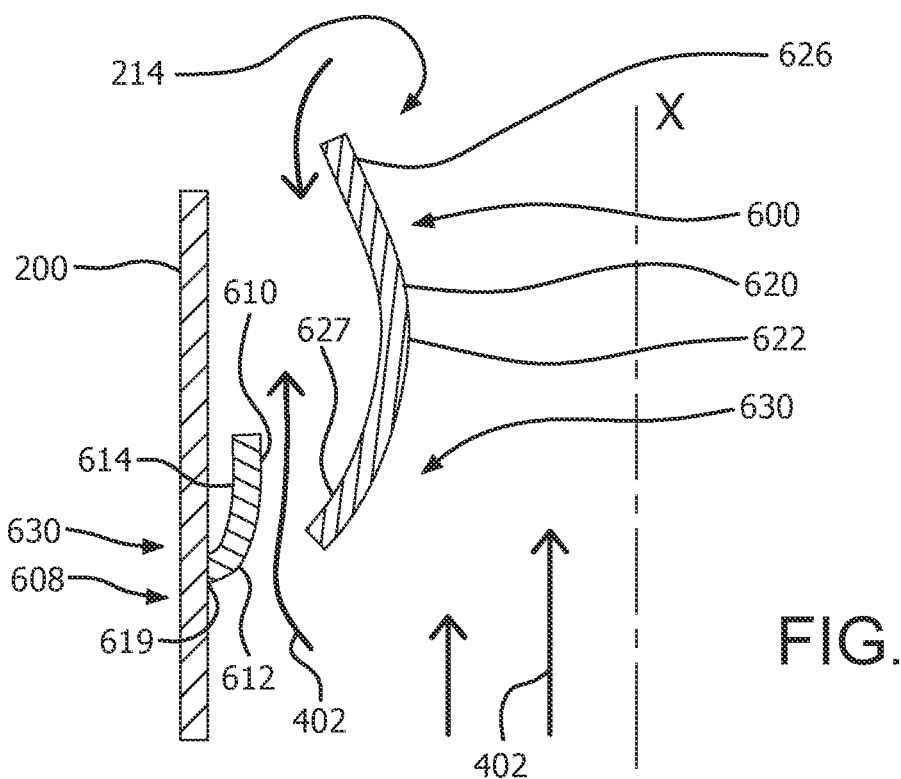
FIG. 11D is a cross-sectional view along cut-line 110 of the embodiment of FIG. 11B when the leaflet is in the open position.

FIG. 11B is a perspective view a prosthetic valve 600 having a frame 200 and a plurality of leaflets 630 each having a plurality of first leaflet components 610 that overlap a second outflow side 624 of a second leaflet component 620, in accordance with an embodiment. The first outflow free edge 616 of the first leaflet component 610 is located adjacent to and overlaps with the second outflow side 624 of the second inflow free edge 627 to define the overlap region 625. The gap 633 will close in sealing engagement at the overlap region 625 to prevent regurgitent flow when the leaflet 630 is in the closed position. FIG. 11C is a cross-sectional view along cut-line 110 of the embodiment of FIG. 11B when the leaflet 630 is in the closed position. FIG. 11D is a cross-sectional view along cut-line 110 of the embodiment of FIG. 11B when the leaflet 630 is in the open position. A gap 330 formed between the first leaflet component 610 and the second leaflet component 620 when the leaflet 630 is not in the closed position allows fluid flow in the forward flow direction 402 to pass through the gap 330 from the first inflow side 612 and the second inflow side 622 disrupting and displacing the recirculating flow 406 behind the leaflet 630. Thus, blood behind the leaflet 630 is less likely to clot or form thrombus, particularly at the leaflet base 608 and where it attaches to the frame 200. Under certain flow conditions, the gap 330 also allows fluid adjacent the first outflow side 614 and the second outflow side 624 to pass through the gap 330 during fluid flow in the forward flow direction 402 through the lumen 214. That is, the recirculating flow 406 behind the leaflet 630 may pass through the gap 330 preventing the recirculating flow 406 from slowing down or stagnating behind the leaflet 630.

Figure 12B:
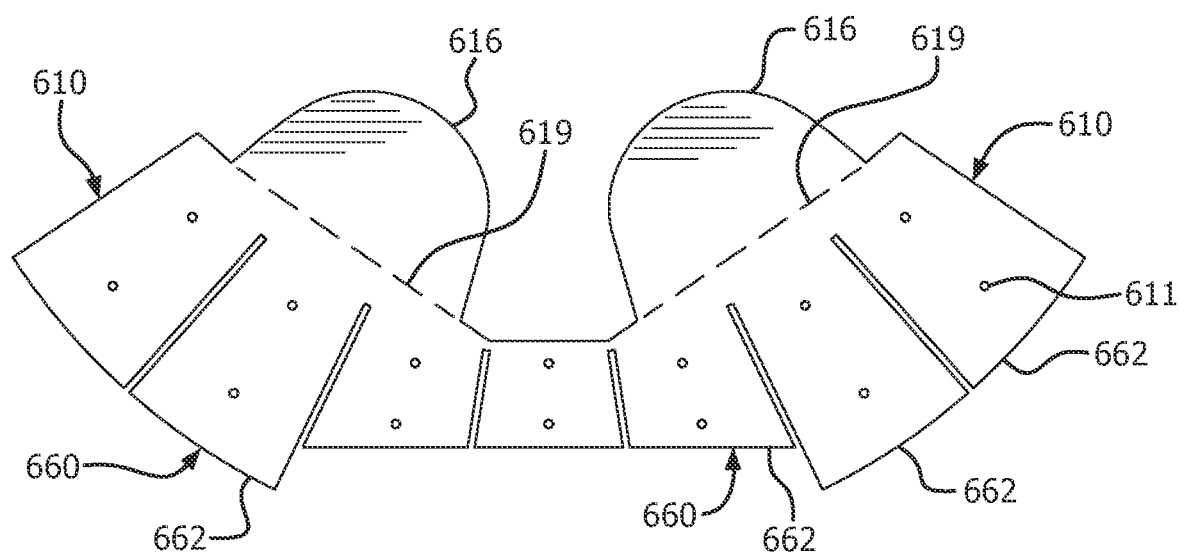
FIG. 12B is a plan view of a leaflet pattern comprising a plurality of first leaflet components, in accordance with an embodiment.

FIG. 12B is another embodiment of a first leaflet component 610 that may be used in cooperation with the second leaflet component 620 of FIG. 13. The first leaflet component 610 comprises two a first frame attachment edges 619 and two first outflow free edges 616. The first frame attachment edges 619 includes a plurality of first tabs 662 that couple to components of the frame 200. This embodiment is similar to the embodiment of FIG. 12A wherein the two first leaflet components 610 are coupled together as one component.

Figure 12C:
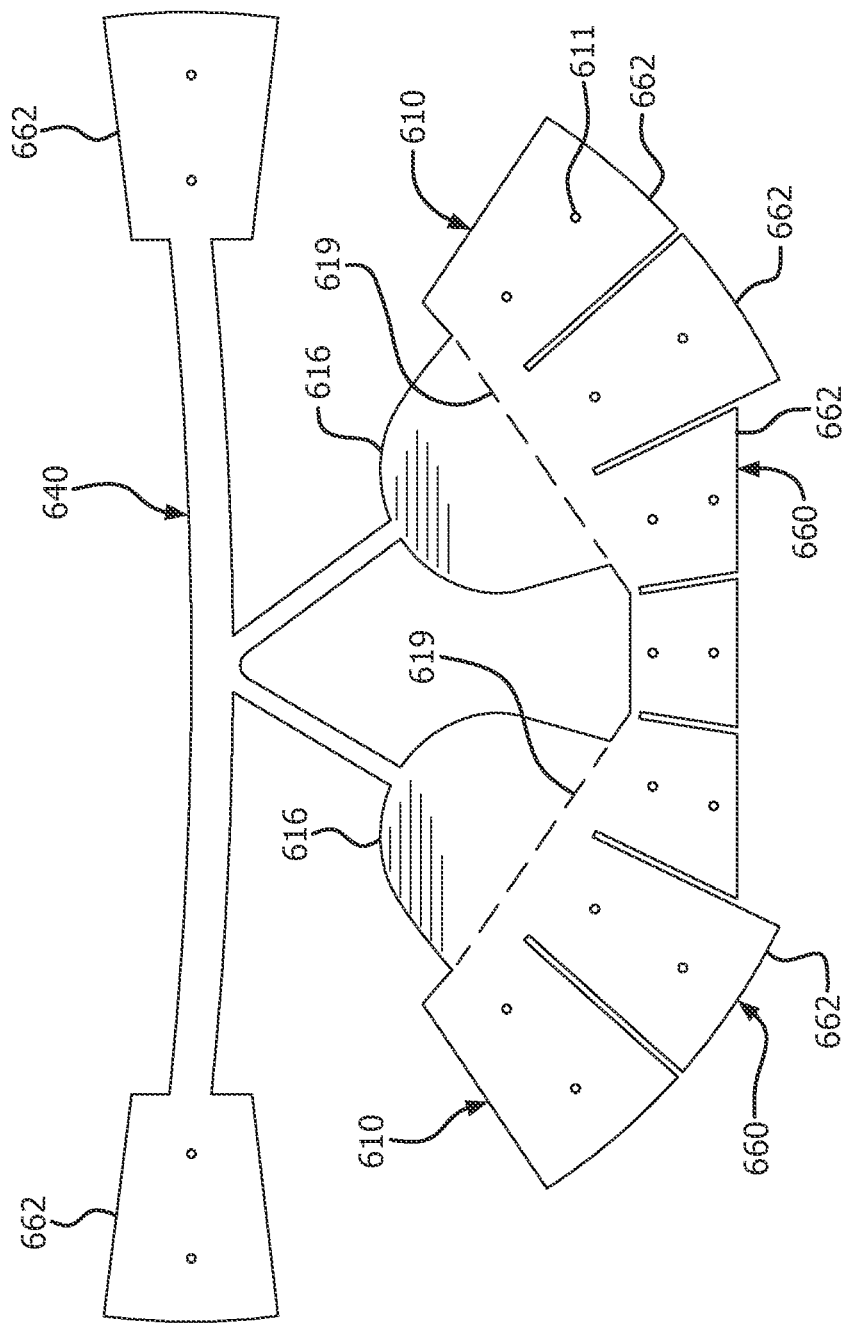
FIG. 12C is a plan view of a leaflet pattern comprising a plurality of first leaflet components, in accordance with an embodiment.

FIG. 12C is another embodiment of a first leaflet component 610 that may be used in cooperation with the second leaflet component 620 of FIG. 13. This embodiment is similar to the embodiment of FIG. 12B wherein the two first leaflet components 610 are coupled together as one component. The first leaflet component 610 comprises two a first frame attachment edges 619 and two first outflow free edges 616. The first frame attachment edges 619 includes a plurality of first tabs 662 that couple to components of the frame 200. The first leaflet component 610 further comprises a tether element 640 that couples the two first outflow free edges 616 to the frame via a plurality of first tabs 662. The tether element 640 is operable to prevent prolapse of the two first outflow free edges 616 when the leaflets are in the closed position.

Figure 14:
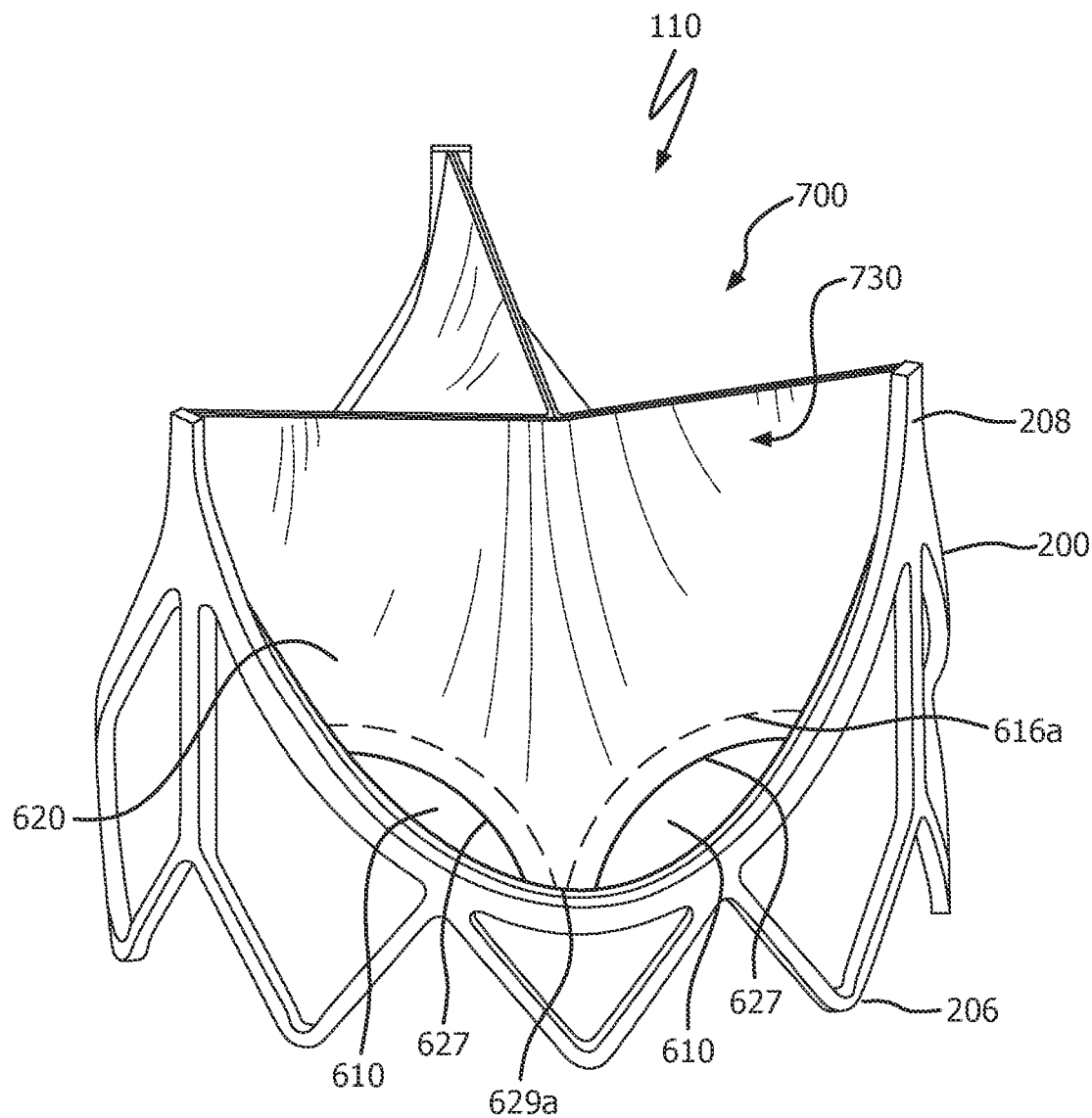
FIG. 14 is a prosthetic valve with a second leaflet component with a relatively narrow strip that attaches as the base of the frame, in accordance with an embodiment.

FIG. 14 is a perspective view a prosthetic valve 700 having a frame 200 and a plurality of leaflets 730 each having a plurality of first leaflet components 610 that overlap a second leaflet component 620, in accordance with an embodiment. The second leaflet component 620 has a relatively narrow upstream-most second frame attachment edge 629a providing the benefit of providing relatively large gaps between the two first leaflet components 610 and the second leaflet component 620 when the leaflet is not in the closed position while providing tethered support of the second inflow free edges 627 that prevents prolapse when in the closed position resisting downstream flow pressure.

Figure 15:
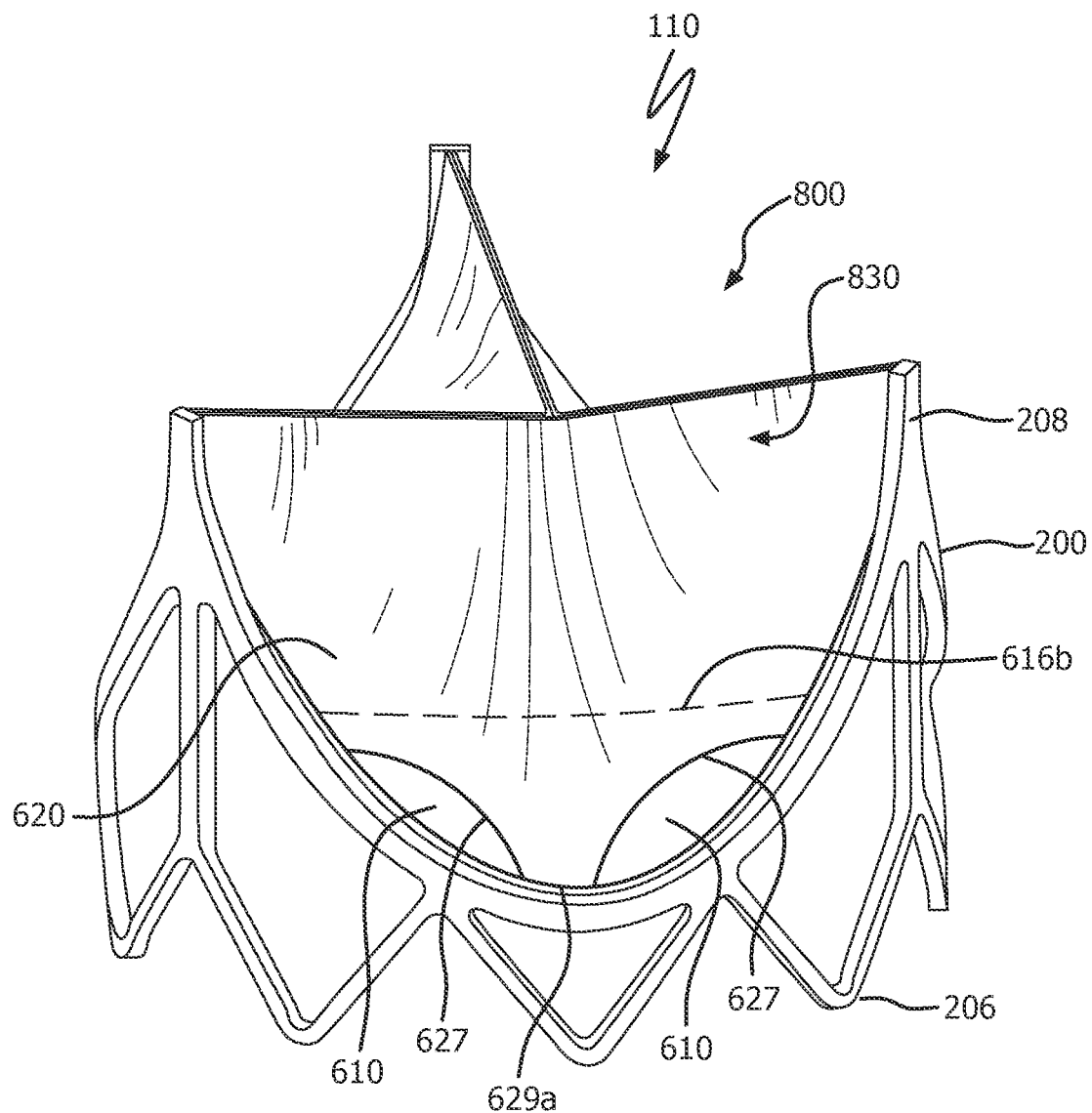
FIG. 15 is another prosthetic valve similar to the embodiment of FIG. 14 that includes one first leaflet component that overlaps both second inflow free edges, in accordance with another embodiment.

FIG. 15 is a perspective view a prosthetic valve 800 having a frame 200 and a plurality of leaflets 830 each having one first leaflet component 610 that overlaps a second leaflet component 620 that defines two second inflow free edges 627, in accordance with another embodiment. The second leaflet component 620 is similar to the embodiment of FIG. 14 in that the second leaflet component 620 has a relatively narrow upstream-most second frame attachment edge 629*a* providing the benefit of providing relatively large gaps between the first leaflet component 610 and the second leaflet component 620 when the leaflet is not in the closed position while providing tethered support of the second inflow free edges 627 that prevents prolapse when in the closed position resisting downstream flow pressure.

It is appreciated that embodiments of the prosthetic valve having one or more first leaflet components and one or more second leaflet components, and where the overlap region is on the inflow side or outflow side of the second leaflet component, are predetermined for a particular purpose to provide flow through the gap therebetween when the leaflet is in the open position and to prevent regurgitent flow through the gap therebetween when the leaflet is in the closed position. The gap formed between the first leaflet component and the second leaflet component when the leaflet is not in the closed position allows fluid adjacent the first outflow side and the second outflow side to pass through the gap during fluid flow in the forward direction through the lumen. That is, the recirculating flow behind the leaflet may pass through the gap 330 preventing the recirculating flow from slowing down or stagnating behind the leaflet. Further, the gap also allows forward flow to pass through the gap from the first inflow side and the second inflow side further disrupting and displacing the recirculating flow behind the leaflet to downstream of the leaflet. Thus, blood behind the leaflet is less likely to clot or form thrombus, particularly where the leaflet attaches to the frame.

Figure 16A:
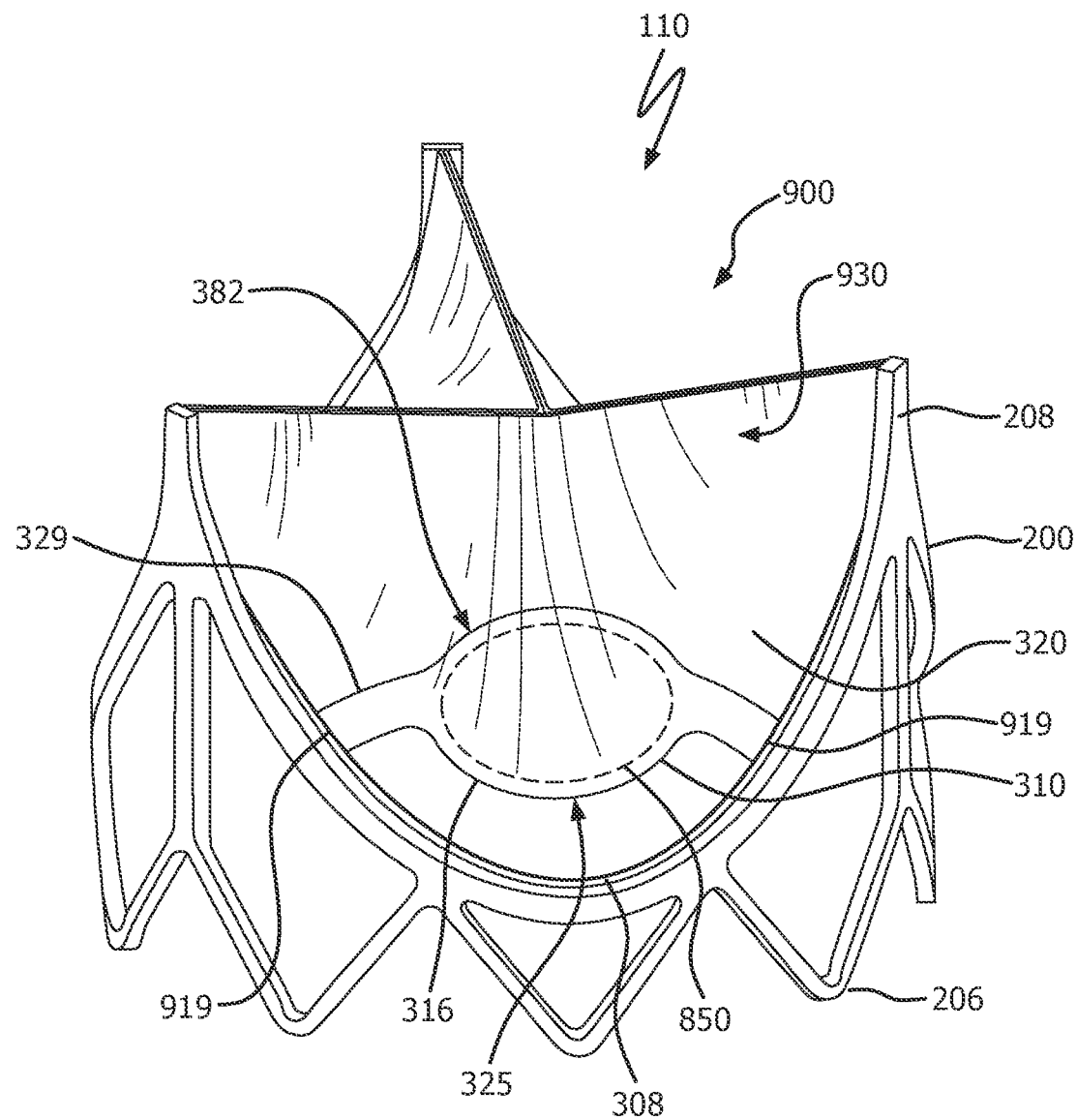
FIG. 16A is perspective view of a prosthetic valve, in accordance with another embodiment.
Figure 16B:
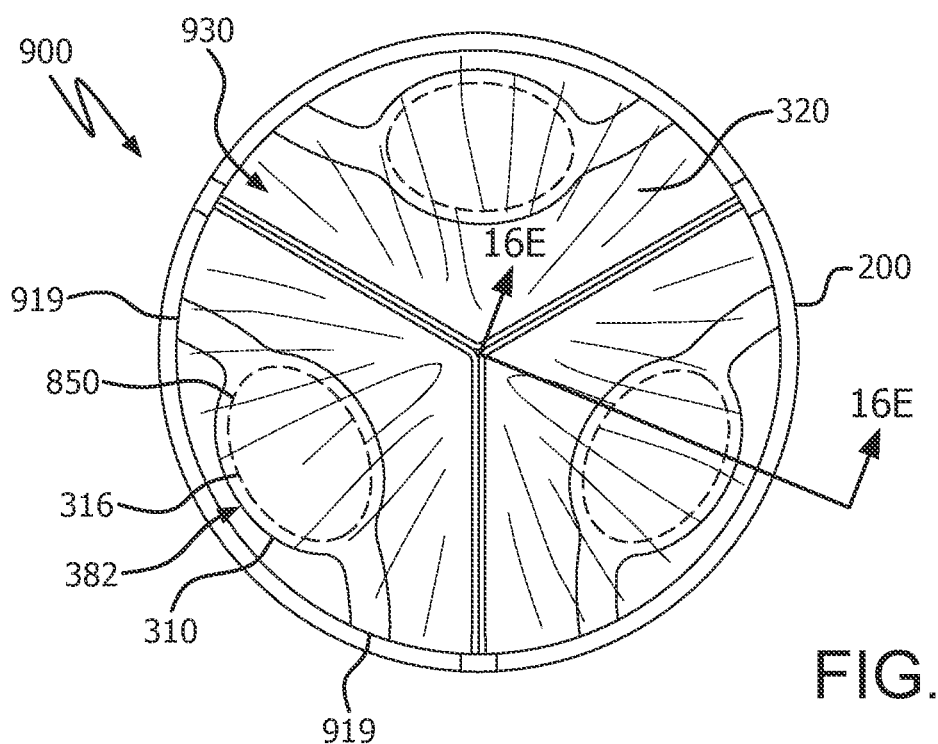
FIG. 16B is an axial view of the prosthetic valve of FIG. 16A in a closed position, in accordance with an embodiment.
Figure 16D:
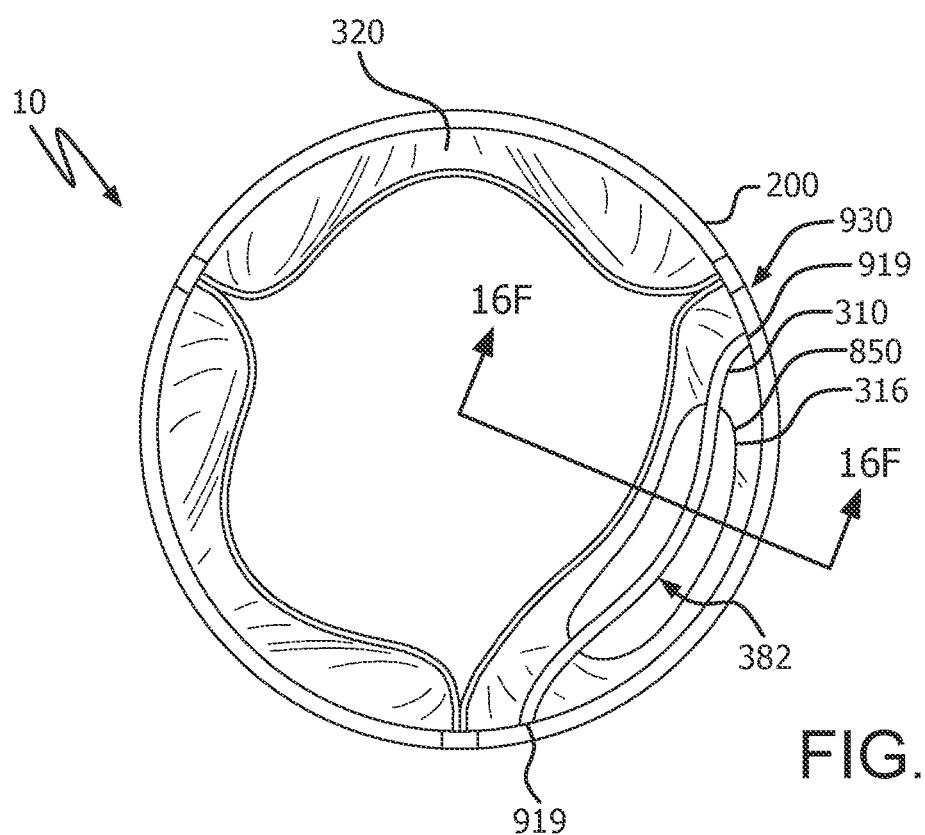
FIG. 16D is an axial view of the prosthetic valve FIG. 16C in an open position, in accordance with an embodiment.
Figure 16C:
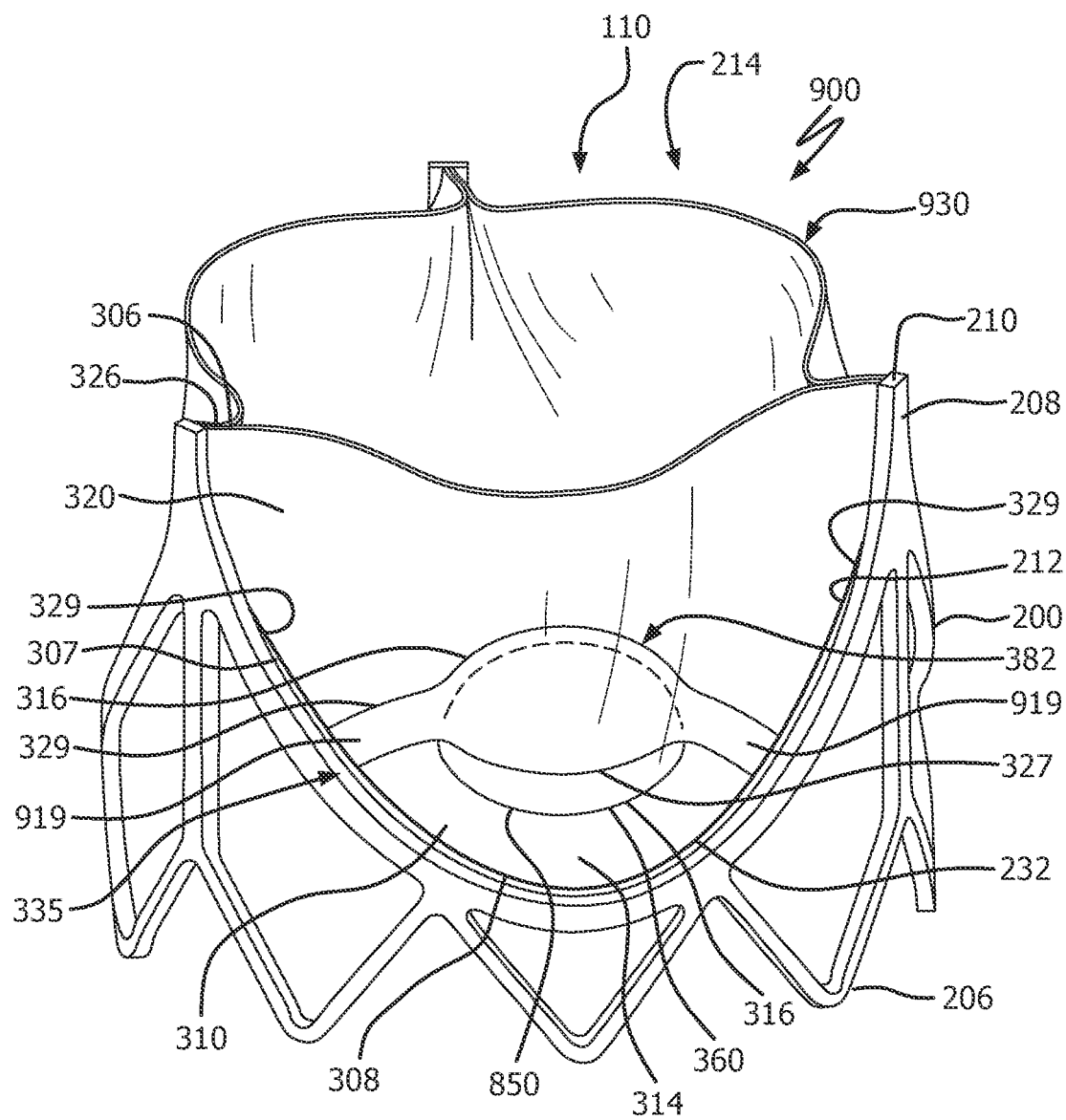
FIG. 16C is a perspective view of the prosthetic valve of FIG. 16A in an open position, in accordance with an embodiment.
Figure 16E:
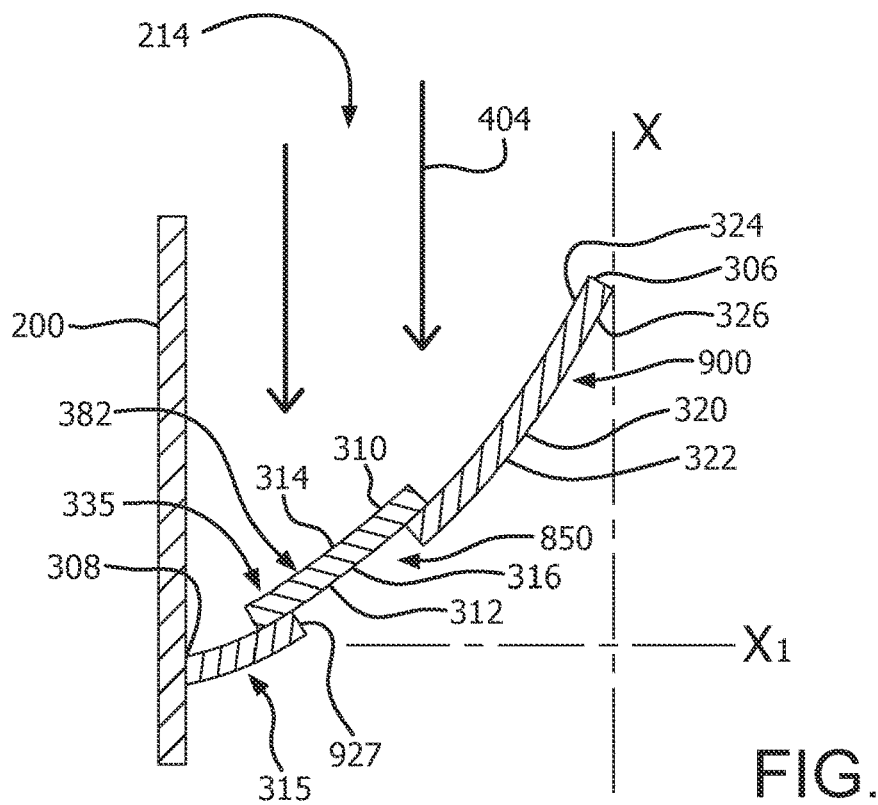
FIG. 16E is a cross-sectional view of the closed valve of FIG. 16B along cutline 16E-16E, in accordance with an embodiment.
Figure 16F:
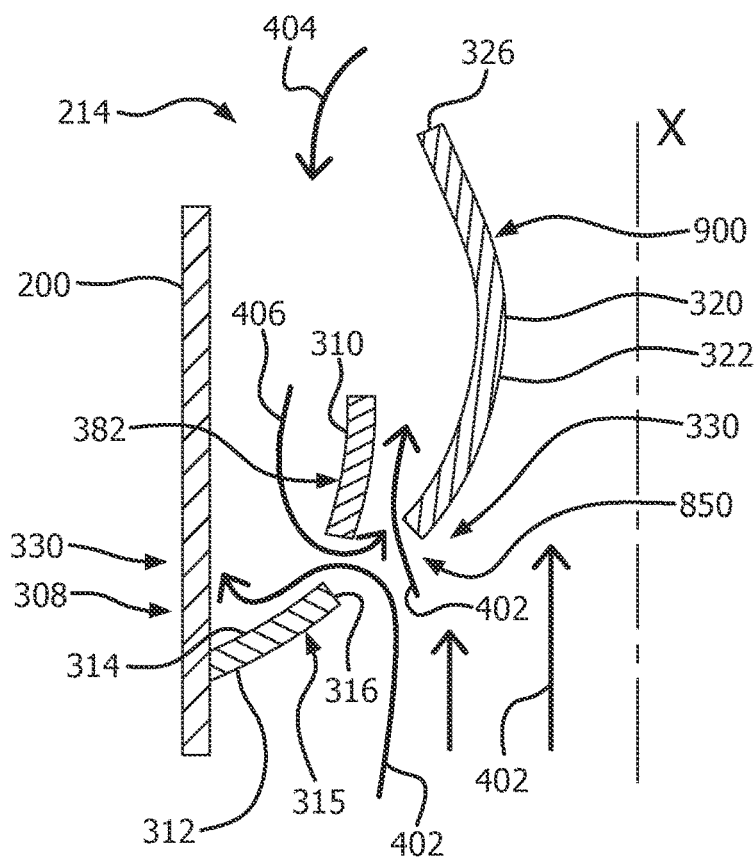
FIG. 16F is a cross-sectional view of the open valve of FIG. 16D along cutline 16F-16F, in accordance with an embodiment.

In accordance with another embodiment, as shown in FIGS. 16A-16F, a prosthetic valve 900 comprises a leaflet 930 having a second leaflet component 320 defining a second leaflet aperture 850 therethrough and a first leaflet component 310 operable to close the second leaflet aperture 850 when the leaflet 930 is in the closed position. FIGS. 16A and 16B are perspective and axial views, respectively, of a prosthetic valve 900 in a closed position, in accordance with an embodiment. FIGS. 16C and 16D are perspective and axial views, respectively, of the prosthetic valve 900 in an open position, in accordance with an embodiment. FIGS. 16E and 16F are cross-sectional views of the closed prosthetic valve 900 of FIG. 16B along cutline 16E-16E and of the prosthetic valve 900 of FIG. 16D along cutline 16F-16F, respectively.

As shown in FIG. 16A, a frame 200 is operable to hold and support a plurality of leaflets 930. The frame 200 is annular, that is, it defines a cylinder having a lumen 214 having an axis X and a plurality of commissure posts 210 extending parallel to the axis X that are spaced from one another. Between the commissure posts 210 is a leaflet attachment region 212 that is operable to couple with and support the leaflet 930 about a perimeter of the leaflet 930.

The leaflet 930 includes a first leaflet component 310 and a second leaflet component 320, in accordance with an embodiment. The first leaflet component 310 has a first inflow side 312 and a first outflow side 314 opposite the first inflow side 312 that defines a first thickness. The first leaflet component 310 has a first frame attachment edge 319 and a first outflow free edge 316. The first leaflet component 310 defines a second leaflet aperture 850 adjacent the leaflet base 308.

The second leaflet component 320 has a second inflow side 322 and a second outflow side 324 opposite the second inflow side 322 defining a second thickness. The second leaflet component 320 has a plurality of second frame attachment edges 329 and an aperture occluder 382 therebetween that is operable to occlude the second leaflet aperture 850 when the leaflet 930 is in the closed position. The first leaflet component 310 and the second leaflet component 320 are configured to be movable between an open position to allow fluid flow in a forward flow direction through the lumen 214 and a closed position in cooperative engagement that prevents regurgitant flow.

The first leaflet component 310 and the second leaflet component are arranged on the frame 200 such that they at least partially overlap. A second overlap region 325 adjacent to the second inflow free edge 327 overlaps a first overlap region 315 adjacent to the first outflow free edge 316 such that a portion of the second inflow side 322 of the second leaflet component 320 is in contact and in sealing engagement with a portion of the first outflow side 314 of the first leaflet component 310 when the leaflet 300 is in the closed position defining a leaflet overlap region 335 operable to prevent regurgitant flow through the leaflet 300 at the leaflet overlap region 335, as shown in FIG. 16E.

During fluid flow in the forward flow direction 402 when the leaflet 930 is not in the closed position, as shown in FIG. 16F, when the inflow pressure is greater than the outflow pressure, the first overlap region 315 and the second overlap region 325 move away from each other wherein the first leaflet component 310 uncovers the second leaflet aperture 850 allowing fluid to flow therethrough. The second leaflet aperture 850 in the second leaflet component 320 when the leaflet 300 is not in the closed position allows fluid adjacent the second inflow side 322 to pass through the second leaflet aperture 850 when the fluid is moving in the forward flow direction 402 through the lumen 214. The aperture occluder 382 to move downstream from the second leaflet aperture 850. Recirculating flow 406 from behind the leaflet 930, including the first leaflet component 310 may pass in front of the aperture occluder 382 so as to prevent the recirculating flow 406 from stagnating behind the leaflet 930. Thus, blood behind the leaflet 930 is less likely to clot or form thrombus, particularly at the leaflet base 308 and where it attaches to the frame 200.

Leaflet Material

In accordance with some embodiments herein, the leaflet 300 can comprise a biocompatible material that is not of a biological source and that is sufficiently compliant and strong for the particular purpose, such as a biocompatible polymer. In accordance with some embodiments, the first leaflet component 310 and the second leaflet component 320 comprise the same material and exhibit the same material properties. In accordance with other embodiments, the first leaflet component 310 has a bending stiffness that is greater than the second leaflet component 320. Examples of providing a predetermined bending stiffness include, but not limited to, using a material having a predetermined modulus and providing a component of predetermined thickness.

In an embodiment, the leaflet 300 comprises a membrane that is combined with an elastomer or elastomeric material to form a composite material. In accordance with other embodiments, the biocompatible material that makes up the leaflet 300 comprises a biological material, such as, but not limited to, human, bovine, and pig tissue.

The leaflet 300 can comprise any biocompatible material sufficiently compliant and flexible, such as a biocompatible polymer. Either one or both of the first leaflet component 310 and the second leaflet component 320 can comprise a membrane that is combined with an elastomer or elastomeric material to form a composite material. The leaflet 300 can comprise, according to an embodiment, a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a composite material while remaining within the scope of the present disclosure. It should also be appreciated that the elastomeric material can include multiple elastomers, multiple types of non-elastomeric components, and include such things as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure, such as pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

In accordance with embodiments, the first leaflet component and the second leaflet component may be formed of at least one of Polyether ether ketone (PEEK), expanded Polytetrafluoroethylene (ePTFE), Fluorinated ethylene propylene (FEP), copolymers of tetrafluoroethylene (TFE) and perfluoromethyl vinyl ether (PMVE) (TFE-PMVE copolymer), urethanes, polyimides, thermoplastics, thermosets, 3D printable metals and polymers (stainless steel, titanium, etc.) nylon, or any other biocompatible material suitable for long term blood contact that is dimensionally stable, and does not leech contaminates.

Further examples of leaflet construct materials include: wherein the leaflet construct comprises at least one fluoropolymer membrane layer; wherein the leaflet construct comprises a laminate having more than one fluoropolymer membrane layer; wherein the at least one fluoropolymer membrane layer is an expanded fluoropolymer membrane layer; wherein an elastomer, elastomeric, non-elastomer, or a copolymer of TFE-PMVE material is contained within the expanded fluoropolymer membrane layer; wherein the elastomer or elastomeric material comprises perfluoromethyl vinyl ether and tetrafluoroethylene; wherein the expanded fluoropolymer membrane layer comprises ePTFE; wherein the leaflet construct comprises a composite material having at least one fluoropolymer membrane layer having a plurality of pores and an elastomer or elastomeric material present in the pores of at least one of the fluoropolymer membrane layers; wherein the composite material comprises fluoropolymer membrane by weight in a range of about 10% to 90%; wherein the elastomer comprises (per)fluoroalkylvinylethers (PAVE); wherein the elastomer or elastomeric material comprises a copolymer of tetrafluoroethylene and perfluoromethyl vinyl ether; wherein the elastomer is silicone; wherein the elastomer is a fluoroelastomer; wherein the elastomer is a urethane; and wherein the elastomer or elastomeric material is a TFE/PMVE copolymer; wherein the TFE/PMVE copolymer comprises essentially of between about 40 and 80 weight percent perfluoromethyl vinyl ether and complementally 60 and 20 weight percent tetrafluoroethylene; and wherein the leaflet construct comprises silicone.

The leaflet comprises a section of material, such as a sheet, that is attached to the frame. The leaflet can be formed of any suitable material, and need only be biocompatible or be able to be made biocompatible. The material can advantageously be formed of a flexible material. Examples of suitable materials for the valve leaflet include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used in the prosthetic valves of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the leaflet, at least because of their abilities to remodel and become incorporated into adjacent tissues. These materials can provide a scaffold onto which cellular in-growth can occur, eventually allowing the material to remodel into a structure of host cells.

In accordance with an embodiment, the first leaflet component and the second leaflet component comprise a porous polymer membrane and an elastomeric material present in pores of the porous polymer membrane such that the first leaflet component and the second leaflet components are impermeable. Further, in another embodiment, the porous polymer membrane is expanded polytetrafluoroethylene. Further, in another embodiment, the elastomeric material is an elastomer. Further, in another embodiment, the elastomeric material is TFE/PMVE copolymer. Further, in another embodiment, the elastomer is TFE/PMVE copolymer.

In accordance with an embodiment, the first leaflet component and the second leaflet component comprise a porous polymer membrane and an elastomer present in pores of the porous polymer membrane such that the first leaflet component and the second leaflet components are impermeable. Further, in another embodiment, the porous polymer membrane is expanded polytetrafluoroethylene. Further, in another embodiment, the elastomer is TFE/PMVE copolymer.

In accordance with an embodiment, the first leaflet component or the second leaflet component comprise a porous polymer membrane and an elastomeric material present in pores of the porous polymer membrane such that the first leaflet component or the second leaflet component, respectively, is impermeable.

In accordance with an embodiment, the first leaflet component and the second leaflet component comprise expanded polytetrafluoroethylene membrane and TFE/PMVE copolymer present in pores of the expanded polytetrafluoroethylene membrane such that the first leaflet component and the second leaflet component, respectively, are impermeable.

In accordance with an embodiment, at least one of the first leaflet component and the second leaflet component comprise a biological tissue.

In accordance with an embodiment, a prosthetic valve comprises a frame and a plurality of leaflets each including one or more first valve components that overlap a second valve component. The frame includes an inflow end and an outflow end and leaflet attachment portions. Each first leaflet component includes a first inflow end portion and a first outflow end portion wherein the first inflow end portion is coupled to a leaflet attachment portion adjacent the inflow end of the frame. The second leaflet portion has a second inflow end portion, a second outflow end portion, a plurality of side attachment portions, a lumen facing side and a frame facing side. At least two side attachment portions are coupled to the leaflet attachment portions of the frame. A portion of the first leaflet outflow end portion overlaps with a portion of the second leaflet inflow end portion of the leaflet on the lumen facing side defining an overlap region. The leaflet being movable between an open position to allow fluid flow in a forward direction through the lumen and a closed position in cooperative engagement with the valve component in sealing engagement at the overlap region that prevents fluid flow in a retrograde direction through the frame. A gap is formed between the overlap region to allow fluid flow therethrough during fluid flow in a forward direction through the frame.

In accordance with another embodiment, a prosthetic valve comprises a first leaflet component and a second leaflet component. The second leaflet component being disposed downstream of the first leaflet component. The first leaflet component and the second leaflet component are in operable engagement configured to allow forward fluid flow through the prosthetic valve in a first direction extending downstream and prevent retrograde fluid flow through the prosthetic valve in an opposite direction extending upstream, and in operable engagement configured to allow fluid flow between a gap defined by the first leaflet component and the second leaflet component during forward fluid flow through the prosthetic valve.

In accordance with another embodiment, a prosthetic valve comprises a frame and a leaflet component coupled to the frame being moveable between a first position that permits fluid to forward flow in a first direction through the prosthetic valve and a second position that hinders retrograde flow in a second direction opposite the first direction through the prosthetic valve. The leaflet component includes a means for opening an aperture during forward flow to enable fluid flow therethrough during forward flow and to close the aperture during retrograde flow.

In accordance with another embodiment, a prosthetic valve, comprises a frame and a leaflet coupled to the frame being moveable between a first position that permits antegrade flow through the prosthetic valve and a second position that prevents retrograde flow through the prosthetic valve. The leaflet component includes a recirculation aperture operable to open to enable recirculation flow therethrough during antegrade flow through the prosthetic valve and operable to close to prevent retrograde flow therethrough through the prosthetic valve.

In accordance with another embodiment, a prosthetic valve comprises a frame, a first leaflet component coupled to the frame, and a second leaflet component coupled to the frame and at least partially overlapping the first leaflet component defining an overlap region. The second leaflet component being moveable between a first position that brings the first leaflet component and the second leaflet component into sealing engagement at the overlap region that prevents retrograde flow through the prosthetic valve and moveable between a second position that allows antegrade flow through the prosthetic valve and separates the first leaflet component and the second leaflet component at the overlap region defining a recirculation aperture that allows recirculation flow through the recirculation aperture.

In accordance with another embodiment, a prosthetic valve comprises a frame and at least one leaflet. The frame has an inflow end and an outflow end opposite the inflow end and defining a lumen therebetween defining an axis, the frame having at least one leaflet attachment region having an inflow portion and an outflow portion. A leaflet is coupled to each of the at least one leaflet attachment regions. Each leaflet includes at least one first leaflet component and a second leaflet component. Each first leaflet component has a first inflow side and a first outflow side opposite the first inflow side, a first frame attachment edge and a first outflow free edge. The second leaflet component has a second inflow side and a second outflow side opposite the second inflow side. The second leaflet component has a plurality of second frame attachment edges, at least one second inflow free edge and a second outflow free edge opposite the at least one second inflow free edge. The second leaflet component being movable between an open position to allow fluid flow in a forward direction through the lumen and a closed position in cooperative engagement with the at least one first leaflet component that prevents fluid flow in a retrograde direction through the lumen. The first frame attachment edge of the at least one first leaflet component being coupled to the inflow portion of the leaflet attachment region with the first inflow side facing the axis. The frame attachment edges of the second leaflet component being coupled to at least the outflow portion of the leaflet attachment region with the second inflow side facing the axis. Wherein a second overlap region of the second inflow free edge overlaps a first overlap region of the first outflow free edge of the at least one first leaflet component when the leaflet is in the closed position defining a leaflet overlap region preventing fluid flow through the lumen in the retrograde direction. Wherein the first overlap region of the at least one first leaflet component and the second overlap region are not in contact therewith wherein the first outflow free edge of the at least one first leaflet component and the second inflow free edge define a gap therebetween when the leaflet is not in the closed position, wherein fluid adjacent the second outflow side can pass through the gap during fluid flow in the forward direction.

In accordance with another embodiment, a prosthetic valve comprises a frame and a plurality of leaflets. The frame has an inflow end and an outflow end opposite the inflow end and defines a lumen therebetween defining an axis. The frame has at least one leaflet attachment region having an inflow portion and an outflow portion. Each leaflet being coupled to each of the at least one leaflet attachment regions. The at least one leaflet includes at least one first leaflet component and a second leaflet component. The at least one first leaflet component has a first inflow side and a first outflow side opposite the first inflow side. The at least one first leaflet component has a first frame attachment edge and a first outflow free edge. The second leaflet component has a second inflow side and a second outflow side opposite the second inflow side. The second leaflet component has a plurality of second frame attachment edges, at least one second inflow free edge and a second outflow free edge opposite the at least one second inflow free edge. The second leaflet component being movable between an open position to allow fluid flow in a forward direction through the lumen and a closed position in cooperative engagement with the at least one first leaflet component that prevents fluid flow in a retrograde direction through the lumen. The first frame attachment edge of each first leaflet component being coupled to the inflow portion of the leaflet attachment region with the first inflow side facing the axis. The frame attachment edges of the second leaflet component being coupled to at least the outflow portion of the leaflet attachment region with the second inflow side facing the axis. Wherein a second overlap region of the second leaflet component adjacent the second inflow free edge overlaps a first overlap region of the first leaflet component adjacent the first outflow free edge such that they are in sealing engagement therewith when the leaflet is in the closed position defining a leaflet overlap region preventing fluid flow through the lumen in the retrograde direction. Wherein the first overlap region of each first leaflet component and the second overlap region are not in contact therewith wherein the first outflow free edge of the each of the first leaflet component and the second inflow free edge define a gap therebetween when the leaflet is not in the closed position, wherein fluid adjacent the second outflow side can pass through the gap during fluid flow in the forward direction.

In accordance with embodiments, the valve may comprise the following properties, singularly or in combination.

The leaflet may comprise a means for allowing a flow or exchange of fluid between the front and back of the leaflet when the leaflet is not in the closed position. Said flow or exchange of fluid may be through the leaflet via an aperture, gap or separation of portions of the leaflet. Said aperture, gap or separation may be operable to close to prevent flow of exchange of fluid between the back and the front of the leaflet, when the leaflet is in the closed position.

The valve may comprise a support structure, such as a frame or a conduit; wherein the leaflet is coupled to the support structure.

The leaflet may include a first leaflet component and a second leaflet component.

The first leaflet component and the second leaflet component may be coupled to the support structure.

The first leaflet component may be upstream of the second leaflet component.

The first leaflet component may be downstream of the second leaflet component.

Said flow or exchange of fluid may be via an aperture, gap or separation of the first and second components, when the leaflet is not in the closed position.

In some embodiments, the second leaflet component comprises an inflow free edge, and defines a gap between the second leaflet component and the support structure. In some embodiments, the first leaflet component or the second leaflet component defines an aperture therethrough, and wherein the other of the first leaflet component or the second leaflet component is operable to occlude the aperture.

The first leaflet component and the second leaflet component may be partially overlapping.

Respective first and second overlap regions of the first leaflet component and the second leaflet component may be in sealing engagement with one another, when the leaflet is in the closed position. The first leaflet component may comprise a first overlap region and the second leaflet component may comprise a second overlap region, wherein the first and second overlap regions together define a leaflet overlap region, when the first and second leaflet components are in sealing engagement with one another.

The first and second overlap regions may extend from a free edge of the respective leaflet component.

The first overlap region may extend from, and typically upstream from, an outflow free edge. The second overlap region may extend from, and typically downstream from, an inflow free edge.

The first and second leaflet components may be brought into sealing engagement with one another by fluid pressure, under the action of retrograde flow.

The first leaflet component may be stationary relative to the second leaflet component, or vice versa. The first leaflet component, or the second leaflet component may be relatively stationary relative to the support structure.

The first leaflet component may be configured to move more slowly than the second leaflet component, or vice versa. In some embodiments, the first leaflet component is downstream of the second leaflet component and the second leaflet component is configured to move more slowly than the first leaflet component. In some embodiments the first leaflet component is upstream of the second leaflet component and the first leaflet component is configured to move more slowly than the second leaflet component.

In some embodiments, the first leaflet component may have a higher, or a lower, bending stiffness than the second leaflet component.

The first leaflet component may comprise apertures in the first overlap region. In some embodiments, the second leaflet component may comprise apertures in the second overlap region. During forward flow (i.e. downstream flow) the apertures in the first or second overlap region may provide, at least in part, that the respective first or second leaflet component moves to the open position at a slower rate than the other said leaflet component, such that a gap is formed therebetween.

In some embodiments, apertures are provided in the first or second overlap regions to augment regurgitant blood flow. In some embodiments, the leaflet component configured to move more slowly is provided with apertures in its overlap region. In some embodiments, the leaflet component configured to move more quickly is provided with apertures in its overlap region.

The apertures in the first or second overlap region may be sealed by the other said overlap region, during retrograde blood flow when the leaflet is in the closed position.

The leaflet overlap region may be of any suitable shape or configuration. In some embodiments, the leaflet overlap region tapers in width towards the support structure. For example, in some embodiments there is no overlap at and optionally to a predetermined distance away from the support structure.

In some embodiments, when the leaflet is in the closed position, there is a regurgitant gap or gaps of a predetermined size between the first and second leaflet components, for example extending away from the support structure. The regurgitant gap or gaps allow a predetermined amount of retrograde flow to pass therethrough, when the valve is closed.

The relative sizes of the first and second leaflet components may determine the axial location of the leaflet overlap region.

The leaflet may provide for flow or exchange of fluid may be via multiple (e.g. two, or three or more) apertures, gaps or separations, when the leaflet is not in the closed position.

The leaflet may comprise multiple first leaflet components. The leaflet may comprise a first leaflet component comprising multiple outflow free edges.

In some embodiments, the second leaflet component may comprise multiple inflow free edges, defining multiple gaps between the second leaflet component and the support structure, corresponding to one of the said multiple first leaflet components or free edges.

In some embodiments, the second leaflet component defines multiple apertures therethrough. The first leaflet component may be operable to occlude the apertures, or one of the said multiple first leaflet components may be operable to occlude each said aperture.

Where there are multiple outflow free edges (either of multiple first leaflet components or of a first leaflet component having multiple outflow free edges), the leaflet may comprise a tether element, which couples said outflow free edges. The tether element may prevent prolapse.

The leaflet may comprise a porous polymer membrane and a material present in pores of the porous polymer membrane such that the or each leaflet is impermeable.

The porous polymer membrane may for example be a fluoropolymer such as expanded polytetrafluoroethylene, or may be a polymer such as polyethylene.

The material present in the pores may be an elastomer or an elastomeric material or may be a non-elastomeric material. The material present in the pores may be a TFE/PMVE copolymer.

The leaflet may alternatively or in addition comprise a biological tissue, such as native valve tissue, or porcine tissue.

Where the valve comprises one or more first leaflet components and a second leaflet component, the or each first leaflet component and/or the second leaflet component may comprise said porous polymer membrane and a material present in pores of the porous polymer membrane such that the or each first leaflet component and/or the second leaflet component is impermeable.

In some embodiments, wherein at least one of the first leaflet component (or components) and the second leaflet component comprises a biological tissue.

The leaflet may have any suitable shape or configuration. For example, the shape of the leaflet, and of a corresponding attachment region to a support structure, may be generally that of a parabola or of an isosceles trapezoid.

The valve may comprise a plurality of leaflets, for example two leaflets, three leaflets or four leaflets. The valve may comprise three leaflets.

Each leaflet may comprise a leaflet free edge. The leaflet free edges may coapt under the influence of outflow (i.e. retrograde) fluid pressure; thereby closing the valve.

The valve may be a prosthetic valve. The valve may be a prosthetic heart valve.

The valve may comprise a leaflet including a first leaflet component and a second leaflet component being disposed downstream of the first leaflet component, the first leaflet component and the second leaflet component are in operable engagement configured to allow forward fluid flow through the prosthetic valve in a first direction extending downstream and prevent regurgitant fluid flow through the prosthetic valve in an opposite direction extending upstream, and in operable engagement configured to allow fluid flow between a gap defined by the first leaflet component and the second leaflet component during forward fluid flow through the prosthetic valve.

The valve may comprise a frame; and a leaflet including a first leaflet component coupled to the frame and a second leaflet component coupled to the frame and at least partially overlapping the first leaflet component defining an overlap region, the second leaflet component being moveable between a first position that brings the first leaflet component and the second leaflet component into sealing engagement at the overlap region that prevents regurgitant flow through the prosthetic valve and moveable between a second position that allows antegrade flow through the prosthetic valve and separates the first leaflet component and the second leaflet component at the overlap region defining a recirculation aperture that allows recirculation flow through the recirculation aperture.

The valve may comprise a frame; and a leaflet including a leaflet component coupled to the frame being moveable between a first position that permits fluid to forward flow in a first direction through the prosthetic valve and a second position that hinders regurgitant flow in a second direction opposite the first direction through the prosthetic valve, the leaflet component including a means for opening an aperture during forward flow to enable fluid flow therethrough during forward flow and to close the aperture during retrograde flow.

The valve may comprise a frame; and a leaflet coupled to the frame being moveable between a first position that permits antegrade flow through the prosthetic valve and a second position that prevents regurgitant flow through the prosthetic valve, the leaflet including a recirculation aperture operable to open to enable recirculation flow therethrough during antegrade flow through the prosthetic valve and operable to close to prevent retrograde flow therethrough through the prosthetic valve.

A method for treating a human patient with a diagnosed condition or disease associated with valve insufficiency or valve failure of a native valve, the method comprising implanting a prosthetic valve at the location of the native valve. The prosthetic valve comprises a frame and a plurality of leaflets. The frame has an inflow end and an outflow end opposite the inflow end and defines a lumen therebetween defining an axis. The frame has at least one leaflet attachment region having an inflow portion and an outflow portion. Each leaflet being coupled to each of the at least one leaflet attachment regions. The at least one leaflet includes at least one first leaflet component and a second leaflet component. The at least one first leaflet component has a first inflow side and a first outflow side opposite the first inflow side. The at least one first leaflet component has a first frame attachment edge and a first outflow free edge. The second leaflet component has a second inflow side and a second outflow side opposite the second inflow side. The second leaflet component has a plurality of second frame attachment edges, at least one second inflow free edge and a second outflow free edge opposite the at least one second inflow free edge. The second leaflet component being movable between an open position to allow fluid flow in a forward direction through the lumen and a closed position in cooperative engagement with the at least one first leaflet component that prevents fluid flow in a retrograde direction through the lumen. The first frame attachment edge of each first leaflet component being coupled to the inflow portion of the leaflet attachment region with the first inflow side facing the axis. The frame attachment edges of the second leaflet component being coupled to at least the outflow portion of the leaflet attachment region with the second inflow side facing the axis. Wherein a second overlap region of the second leaflet component adjacent the second inflow free edge overlaps a first overlap region of the first leaflet component adjacent the first outflow free edge such that they are in sealing engagement therewith when the leaflet is in the closed position defining a leaflet overlap region preventing fluid flow through the lumen in the retrograde direction. Wherein the first overlap region of each first leaflet component and the second overlap region are not in contact therewith wherein the first outflow free edge of the each of the first leaflet component and the second inflow free edge define a gap therebetween when the leaflet is not in the closed position, wherein fluid adjacent the second outflow side can pass through the gap during fluid flow in the forward direction.

A method for reducing incidents of thrombus or reducing thrombus formation associated with treating a human patient with a diagnosed condition or disease associated with valve insufficiency or valve failure of a native valve, the method comprising implanting a prosthetic valve at the location of the native valve. The prosthetic valve comprises a frame and a plurality of leaflets. The frame has an inflow end and an outflow end opposite the inflow end and defines a lumen therebetween defining an axis. The frame has at least one leaflet attachment region having an inflow portion and an outflow portion. Each leaflet being coupled to each of the at least one leaflet attachment regions. The at least one leaflet includes at least one first leaflet component and a second leaflet component. The at least one first leaflet component has a first inflow side and a first outflow side opposite the first inflow side. The at least one first leaflet component has a first frame attachment edge and a first outflow free edge. The second leaflet component has a second inflow side and a second outflow side opposite the second inflow side. The second leaflet component has a plurality of second frame attachment edges, at least one second inflow free edge and a second outflow free edge opposite the at least one second inflow free edge. The second leaflet component being movable between an open position to allow fluid flow in a forward direction through the lumen and a closed position in cooperative engagement with the at least one first leaflet component that prevents fluid flow in a retrograde direction through the lumen. The first frame attachment edge of each first leaflet component being coupled to the inflow portion of the leaflet attachment region with the first inflow side facing the axis. The frame attachment edges of the second leaflet component being coupled to at least the outflow portion of the leaflet attachment region with the second inflow side facing the axis. Wherein a second overlap region of the second leaflet component adjacent the second inflow free edge overlaps a first overlap region of the first leaflet component adjacent the first outflow free edge such that they are in sealing engagement therewith when the leaflet is in the closed position defining a leaflet overlap region preventing fluid flow through the lumen in the retrograde direction. Wherein the first overlap region of each first leaflet component and the second overlap region are not in contact therewith wherein the first outflow free edge of the each of the first leaflet component and the second inflow free edge define a gap therebetween when the leaflet is not in the closed position, wherein fluid adjacent the second outflow side can pass through the gap during fluid flow in the forward direction.

Applications

The prosthetic valve of the embodiments provided herein can be used as a prosthetic heart valve. In this capacity, the prosthetic valve is placed in an orifice collocated with a native heart valve or in place of an excised heart valve to regulate the flow of blood through the heart. It is believed that the leaflet moves to the first position, for example, as illustrated in FIG. 2B, during systole in which the heart forces blood through the artery or vein in a forward flow direction 402. During diastole, the leaflet 300 moves to the closed position, illustrated in FIG. 2A, to substantially prevent fluid flow in the second, opposite direction referred to as retrograde flow. It is believed that a pressure change and reversal of flow direction occurs during the change from systole to diastole, and the leaflet 300 changes position in response to these changes.

The prosthetic valve of the embodiments provided herein can also be used as a prosthetic venous valve. In this capacity, the prosthetic valve is placed in a vein to regulate the flow of blood through the vein.

In accordance with an embodiment, a method of making a prosthetic valve comprises obtaining a leaflet frame, and a leaflet including a first leaflet component and a second leaflet component. Coupling the first leaflet component adjacent to an inlet portion of the leaflet frame. Coupling the second leaflet component adjacent to an outlet portion of the leaflet frame such that a second overlap region of a second inflow free edge of the second leaflet component overlaps a first overlap region of a first outflow free edge of the first leaflet component such that a portion of a second inflow side of the second leaflet component is in contact and in sealing engagement with a portion of a first outflow side of the first leaflet component when the leaflet is in a closed position defining a leaflet overlap region preventing fluid flow through the lumen in the retrograde direction. And wherein the first overlap region and the second overlap region are not in contact therewith wherein the first outflow free edge and the second inflow free edge define a gap therebetween when the leaflet is not in the closed position, wherein fluid adjacent the second outflow side can pass through the gap during fluid flow in the forward direction.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A method for treating a native valve of a human patient, the method comprising:
    implanting at or adjacent to a location of the native valve a prosthetic valve comprising a plurality of leaflets, each leaflet having a first outflow free edge, wherein each leaflet is moveable between an open position that permits antegrade flow through the prosthetic valve and a closed position wherein the first outflow free edges of adjacent leaflets coapt with each other to prevent regurgitant flow through the prosthetic valve, each leaflet having a gap to allow a flow or exchange of fluid between a front and a back of the respective leaflet when the respective leaflet is not in the closed position,
    the prosthetic valve further comprising a support structure, wherein each leaflet is coupled to the support structure,
    wherein each leaflet includes a first leaflet component and a second leaflet component, wherein the first leaflet component is upstream of the second leaflet component, wherein the-gap for the flow or exchange of fluid between the front and the back of the respective leaflet is disposed between the first and second leaflet components when the respective leaflet is not in the closed position, wherein the second leaflet component comprises the first outflow free edge of the respective leaflet and an inflow free edge unattached to the support structure, wherein the plurality of leaflets comprise three leaflets each having the first and second leaflet components, and wherein the first outflow free edges of the three leaflets coapt in a tricuspid arrangement.

2. The method of claim 1, wherein the first leaflet component and the second leaflet component partially overlap.

3. The method of claim 2, wherein the first leaflet component comprises a first overlap region and the second leaflet component comprises a second overlap region, wherein the first and second overlap regions are in sealing engagement with one another when the respective leaflet is in the closed position.

4. The method of claim 3, wherein the first overlap region extends from a second outflow free edge of the first leaflet component and the second overlap region extends from the inflow free edge of the second leaflet component.

5. The method of claim 1, wherein the first leaflet component has a higher bending stiffness than the second leaflet component.

6. The method of claim 1, wherein the first and second leaflet components overlap and define an overlap region which tapers in width towards the support structure.

7. The method of claim 1, wherein a shape of each leaflet and a corresponding attachment region to a support structure is parabolic.

8. The method of claim 1, wherein each leaflet comprises a porous polymer membrane and a material present in pores of the porous polymer membrane such that the respective leaflet is impermeable.

9. The method of claim 8, wherein the porous polymer membrane is expanded polytetrafluoroethylene.

10. The method of claim 9, wherein the material present in the pores is an elastomer or an elastomeric material or a non-elastomeric material.

11. The method of claim 9, wherein the material present in the pores is a TFE/PMVE copolymer.

12. The method of claim 1, wherein each leaflet comprises a biological tissue.

13. A method for reducing incidents of thrombus or reducing thrombus formation, the method comprising:
implanting at or adjacent to a location of the native valve a prosthetic valve comprising a plurality of leaflets,
the prosthetic valve further comprising a support structure, wherein each leaflet is coupled to the support structure,
wherein each leaflet includes a first leaflet component and a second leaflet component, wherein the first leaflet component is upstream of the second leaflet component, wherein the second leaflet component has an outflow edge and an inflow edge and the first leaflet component has an outflow edge and an inflow edge,
wherein the leaflets are moveable between an open position that permits antegrade flow through the prosthetic valve and a closed position in which the outflow edges of the second leaflet components coapt with each other to prevent regurgitant flow through the prosthetic valve, wherein when the leaflets are in the open position, antegrade blood can flow through a gap between the first and second leaflet components of each leaflet, wherein the plurality of leaflets comprise three leaflets each having the first and second leaflet components, and wherein the first outflow free edges of the three leaflets coapt in a tricuspid arrangement.

14. The method of claim 13, wherein the first leaflet component and the second leaflet component partially overlap.

15. The method of claim 14, wherein the first leaflet component comprises a first overlap region along the outflow edge of the first leaflet component and the second leaflet component comprises a second overlap region along the inflow edge of the second leaflet component, wherein the first and second overlap regions are in sealing engagement with one another when the respective leaflet is in the closed position.

16. The method of claim 15, wherein the first overlap region extends from the outflow edge of the first leaflet component and the second overlap region extends from the inflow edge of the second leaflet component.

17. The method of claim 13, wherein the first leaflet component has a higher bending stiffness than the second leaflet component.

18. The method of claim 13, wherein the first and second leaflet components overlap and define an overlap region which tapers in width towards the support structure.

19. The method of claim 13, wherein a shape of each leaflet and a corresponding attachment region to a support structure is parabolic.

20. The method of claim 13, wherein each leaflet comprises a porous polymer membrane and a material present in pores of the porous polymer membrane such that the respective leaflet is impermeable.

21. The method of claim 20, wherein the porous polymer membrane is expanded polytetrafluoroethylene.

22. The method of claim 21, wherein the material present in the pores is an elastomer or an elastomeric material or a non-elastomeric material.

23. The method of claim 21, wherein the material present in the pores is a TFE/PMVE copolymer.

24. The method of claim 13, wherein each leaflet comprises a biological tissue.

25. The method of claim 1, wherein, when each leaflet is in the closed position, the gap between the first and second leaflet components of the respective leaflet is closed to prevent the flow or exchange of fluid between the front and the back of the respective leaflet.

26. The method of claim 13, wherein, when each leaflet is in the closed position, the gap between the first and second leaflet components of the respective leaflet is closed to prevent the flow or exchange of fluid between the front and the back of the respective leaflet.

* * * * *